United States Patent [19]

Diana et al.

[11] Patent Number: 5,643,929

[45] Date of Patent: *Jul. 1, 1997

[54] 1,2,4-OXIDIAZOLYL-PHENOXYALKYLISOXAZOLES AND THEIR USE AS ANTIVIRAL AGENTS

[75] Inventors: Guy Dominic Diana, North Coventry Township, Chester County; Theodore John Nitz, East Coventry Township, Chester County, both of Pa.

[73] Assignee: Sanofi Winthrop, Inc., New York, N.Y.

[ * ] Notice: The term of this patent shall not extend beyond the expiration date of Pat. No. 5,464,848.

[21] Appl. No.: 444,795

[22] Filed: May 19, 1995

Related U.S. Application Data

[60] Division of Ser. No. 131,050, Oct. 1, 1993, Pat. No. 5,464,848, which is a continuation-in-part of Ser. No. 869,287, Apr. 15, 1992, Pat. No. 5,349,068.

[51] Int. Cl.$^6$ ............................ C07D 413/12; A01K 31/41
[52] U.S. Cl. ............................ 514/364; 548/131; 548/132; 548/133
[58] Field of Search ............................ 548/131, 132, 548/133; 514/364

[56] References Cited

U.S. PATENT DOCUMENTS

| | | | |
|---|---|---|---|
| 5,175,178 | 12/1992 | Diana et al. | 514/364 |
| 5,349,068 | 9/1994 | Diana et al. | 514/364 |
| 5,464,848 | 11/1995 | Diana et al. | 514/364 |

*Primary Examiner*—Robert Gerstl
*Attorney, Agent, or Firm*—Paul E. Dupont

[57] ABSTRACT

Compounds of the formula wherein:

$R_1$ is alkyl, alkoxy, hydroxy, cycloalkyl, hydroxyalkyl, alkoxyalkyl, hydroxyalkoxy, alkylthioalkyl, alkylsulfinylalkyl, alkylsulfonylalkyl, aminoalkyl, alkylaminoalkyl, dialkylaminoalkyl, alkoxycarbonyl, carboxy, or cyanomethyl;

Y is alkylene of 3 to 9 carbon atoms, $R_2$ and $R_3$ independently are hydrogen, alkyl, alkoxy, halo, cyano, trifluoromethyl and nitro;

$R_4$ is alkoxy, hydroxy, halomethyl, dihalomethyl, trihalomethyl, dihaloethyl, cycloalkyl, heterocyclyl, alkoxycarbonyl, hydroxyalkyl, alkoxyalkyl, alkanecarbonyloxyalkyl, cyano, halo, thioalkyl, alkylthioalkyl, alkylthio, thio, 2,2,2-trifluoro-ethyl, (4-methylphenyl)sulfonyloxymethyl, N=Q or CON=Q, where N=Q is amino, alkylamino or dialkylamino;

$R_5$ is hydrogen or halo or alkyl.

35 Claims, No Drawings

1,2,4-OXIDIAZOLYL-PHENOXYALKYLISOXAZOLES AND THEIR USE AS ANTIVIRAL AGENTS

REFERENCE TO RELATED APPLICATIONS

This application is a division of application Ser. No. 08/131,050, filed on Oct. 1, 1993, U.S. Pat. No. 5,464,848 which in turn is a continuation in part of application Ser. No. 07/869,287, filed Apr. 15, 1992, U.S. Pat. No. 5,349,068.

BACKGROUND OF THE INVENTION a) Field of the Invention

This invention relates to novel 1,2,4-oxadiazolyl-phenoxyalkylisoxazoles, to methods for the preparation thereof, and compositions and methods for the use thereof as antiviral agents.

b) Information Disclosure Statement

Diana U.S. Pat. No. 4,843,087, issued Jun. 27, 1989, discloses heteryl-phenoxyalkylisoxazoles, wherein the heteryl moiety is an oxazole or an oxazine, which exhibit antiviral activity.

Diana et al. U.S. Pat. No. 4,857,539, issued Aug. 15, 1989, discloses antivirally active compounds of the formula

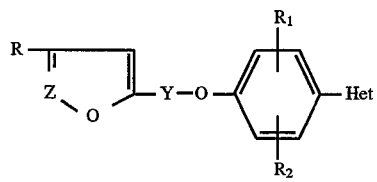

wherein:

Y is an alkylene bridge of 3–9 carbon atoms;
Z is N or HC:
R is hydrogen or lower-alkyl of 1–5 carbon atoms, with the proviso that when Z is N, R is lower-alkyl;
$R_1$ and $R_2$ are hydrogen, halogen, lower-alkyl, lower-alkoxy, nitro, lower-alkoxycarbonyl or trifluoromethyl; and
Het is selected from specified heterocyclic groups. Included in the definition of Het is unsubstituted 1,3,4-oxadiazol-2-yl and unsubstituted 1,2,4-oxadiazol-5-yl.

Diana et al. U.S. Pat. No. 4,861,791, issued Aug. 29, 1989, discloses antivirally active compounds of the formula, inter alia,

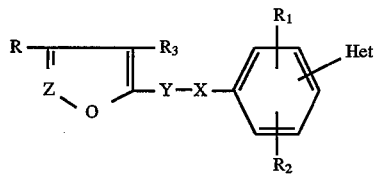

wherein:

Y is an alkylene bridge of 3 to 9 carbon atoms optionally interrupted by one or two oxygen atoms, by cyclohexyl or by an olefinic linkage;
X is O, S, SO or $SO_2$;
Z is N or $R_8$C, where $R_8$ is hydrogen or lower-alkanoyl;
$R_1$ and $R_2$ are selected from the group consisting of hydrogen, lower-alkyl, lower-alkenyl, halogen, nitro, lower-alkoxy, lower-alkylthio, difluoromethyl, trifluoromethyl, amino, lower-alkanoylamino, di-lower-alkylamino, hydroxy, lower-alkenoyl, lower-alkanoyl, hydroxymethyl and carboxy;

R and $R_3$ are each hydrogen or alkyl of 1 to 3 carbon atoms optionally substituted by a member of the group consisting of hydroxy, lower-alkanoyloxy, lower-alkoxy, halo or N=Z', wherein N=Z' is amino, lower-alkanoylamino, lower-alkylamino, di-lower-alkylamino, 1-pyrrolidyl, 1-piperidinyl or 4-morpholinyl; with the proviso that when Z is N, R is other than hydrogen; and Het is selected from specified heterocyclic groups including unsubstituted 1,3,4-oxadiazol-2-yl.

Diana et al. U.S. Pat. No. 4,942,241, issued Jul. 17, 1990, discloses antivirally active compounds of the formulas

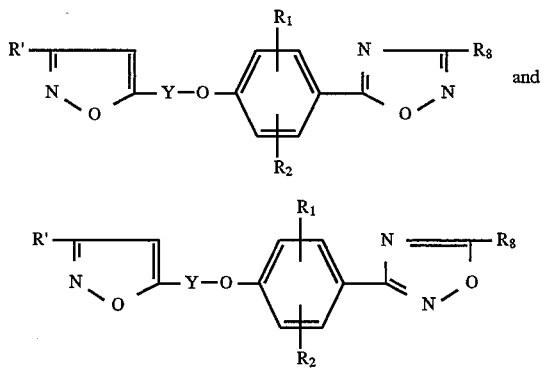

wherein:

Y is an alkylene bridge of 1–9 carbon atoms;
R' is lower-alkyl or hydroxy-lower-alkyl of 1–5 carbon atoms;
$R_1$ and $R_2$ are hydrogen, halogen, lower-alkyl, lower-alkoxy, nitro, lower-alkoxycarbonyl or trifluoromethyl; and
$R_8$ is hydrogen or lower-alkyl of 1–5 carbon atoms.

Diana U.S. Pat. No. 4,945,164, issued Jul. 31, 1990, discloses antivirally active compounds of the formula, inter alia,

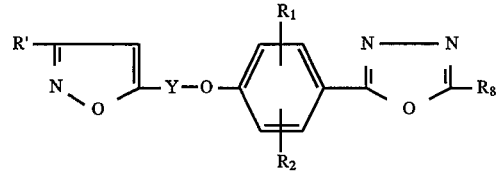

wherein:

Y is an alkylene bridge of 3–9 carbon atoms;
R' is lower-alkyl or hydroxy-lower-alkyl of 1–5 carbon atoms;
$R_1$ and $R_2$ are hydrogen, halogen, lower-alkyl, lower-alkoxy, nitro, lower-alkoxycarbonyl or trifluoromethyl; and
$R_8$ is hydrogen or lower-alkyl of 1–5 carbon atoms.

Commonly assigned G. D. Diana and T. R. Bailey U.S. patent application Ser. No. 07/731,569, filed Jul. 17, 1991, discloses compounds of the formula

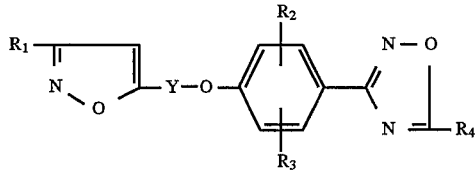

wherein:

Y is alkylene of 3 to 9 carbon atoms;
$R_1$ is lower-alkyl, lower-alkoxy-($C_{1-3}$-alkyl), lower-alkoxycarbonyl, cyclopropyl or trifluoromethyl;

$R_2$ and $R_3$ independently are hydrogen, lower-alkyl, halogen, lower-alkoxy, nitro, trifluoromethyl or hydroxy; and $R_4$ is hydrogen or lower-alkyl; where lower-alkyl and lower-alkoxy, each occurrence, have from 1-5 carbon atoms;

with the proviso that when $R_1$ is lower-alkyl, at least one of $R_2$ and $R_3$ is hydroxy.

SUMMARY OF THE INVENTION

In one aspect the invention provides a compound of the formula

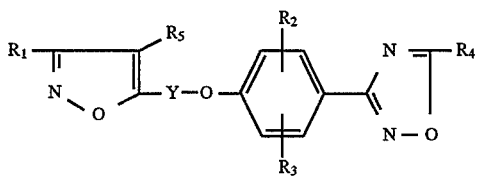

wherein:

$R_1$ is alkyl, alkoxy, hydroxy, cycloalkyl, hydroxyalkyl, alkoxyalkyl, hydroxyalkoxy, alkylthioalkyl, alkylsulfinylalkyl, alkylsulfonylalkyl, aminoalkyl, alkylaminoalkyl, dialkylaminoalkyl, alkoxycarbonyl, carboxy, cyanomethyl;

Y is alkylene of 3 to 9 carbon atoms, $R_2$ and $R_3$ independently are hydrogen, alkyl, alkoxy, halo, cyano, trifluoromethyl or nitro;

$R_4$ is alkoxy, hydroxy, halomethyl, dihalomethyl, trihalomethyl, dihaloethyl, cycloalkyl, heterocyclyl, alkoxycarbonyl, hydroxyalkyl, alkoxyalkyl, alkanecarbonyloxyalkyl, cyano, halo, thioalkyl, alkylthioalkyl, alkylthio, thio, 2,2,2-trifluoroethyl, 2,2,2-trihaloethyl, (4-methylphenyl)-sulfonyloxy-methyl, N=Q or CON=Q, where N=Q is amino, alkylamino or dialkylamino;

$R_5$ is halo, or hydrogen, or alkyl.

In another aspect the invention provides a compound of the formula

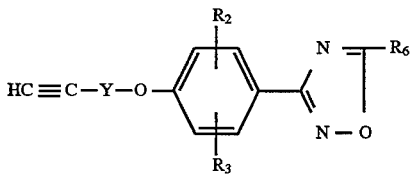

wherein Y, $R_2$ and $R_3$ are as defined above and $R_6$ is alkoxy, fluoromethyl, difluoromethyl, trihalomethyl, cycloalkyl or alkoxyalkyl.

In another aspect the invention provides a compound of the formula

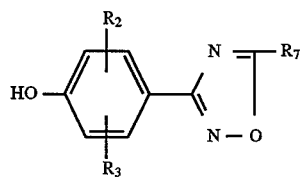

wherein $R_2$ and $R_3$ are as defined above and $R_7$ is alkoxy, fluoromethyl, difluoromethyl, trifluoromethyl, cycloalkyl, alkoxyalkyl or cyano.

In other aspects the invention provides compounds of formulas XVII and XXI hereinafter.

In other aspects the invention provides a composition for combatting picornaviruses which comprises an antivirally effective amount of a compound of formula I in admixture with a suitable carrier or diluent and to methods for combatting picornaviruses therewith including combatting a picornaviral infection in a mammalian host.

The compounds of formula I are useful as antipicornaviral agents.

The compounds of formulas III, IV, XVII and XXI are useful as intermediates for the preparation of the compounds of formula I.

DETAILED DESCRIPTION INCLUSIVE OF PREFERRED EMBODIMENTS

Preferred compounds of formula I are those wherein $R_1$ is $C_{1-5}$-alkyl, $C_{1-5}$-alkoxy, hydroxy, cyclopropyl, hydroxy-$C_{1-5}$-alkyl, $C_{1-3}$-alkoxy-$C_{1-5}$-alkyl, hydroxy-$C_{1-5}$-alkoxy, methylthiomethyl, methylsulfinylmethyl, methylsulfonylmethyl or cyanomethyl;

Y is alkylene of 3 to 9 carbon atoms, especially 3 to 5 carbon atoms;

$R_2$ and $R_3$ independently are hydrogen, $C_{1-3}$-alkyl, $C_{1-3}$-alkoxy or halo, cyano; and $R_4$ is $C_{1-3}$-alkoxy, hydroxy, halomethyl, dihalomethyl, trihalomethyl, cyclopropyl, $C_{1-3}$-alkoxycarbonyl, hydroxy-$C_{1-3}$-alkyl, $C_{1-3}$-alkoxy-$C_{1-3}$-alkyl, ($C_{1-3}$-alkane) carbonyloxy-$C_{1-3}$-alkyl, cyano, 2,2,2-trifluoroethyl, 4-(methylphenyl)sulfonyl-oxymethyl, N=Q or CON=Q, where N=Q is amino, $C_{1-3}$-alkylamino, $R_5$ is hydrogen or di-($C_{1-3}$-alkyl)amino.

$R_5$ is hydrogen, halo or alkyl.

More preferred compounds of formula I are compounds of the formula

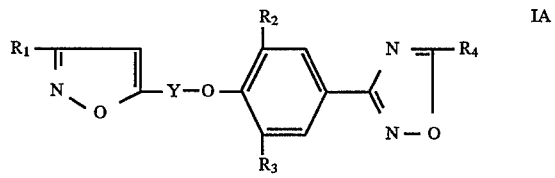

wherein $R_1$, Y, $R_2$, $R_3$, and $R_4$ are as defined above for formula I and $R_5$ is hydrogen and especially wherein $R_1$, Y, $R_2$, $R_3$ and $R_4$ are as defined in the previous paragraph for the preferred compounds of formula I.

Especially preferred are the compounds of formula I or IA wherein $R_4$ is $C_{1-3}$-alkoxy, fluoromethyl, dihalomethyl, trihalomethyl, cycloalkyl or $C_{1-3}$-alkoxy-$C_{1-3}$-alkyl, especially trifluoromethyl.

It should be understood that in the compounds of the invention, when the 1,2,4-oxadiazole ring is substituted by hydroxy, amino or alkylamino, they may exist in any of three possible tautomeric forms as follows:

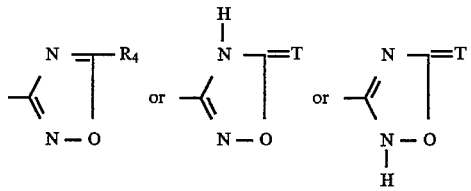

wherein $R_4$ is hydroxy, amino or alkylamino and T is O, NH or N-alkyl, and such tautomers are within the purview of the invention.

As used herein, unless otherwise specifically defined, alkyl, alkane, alkoxy, cycloalkyl and halo each has the following meaning:

alkyl and alkoxy mean aliphatic radicals, including branched radicals, of from one to five carbon atoms. Thus the alkyl moiety of such radicals include, for example methyl, ethyl, propyl, isopropyl, n-butyl, sec-butyl, t-butyl and pentyl;

alkane means a monovalent aliphatic alkyl radical, including branched radicals of from one to four carbon atoms. Thus the alkane moiety of such radical includes, for example, methyl, ethyl, propyl, isopropyl, n-butyl and sec-butyl;

cycloalkyl means an alicyclic radical having from three to six carbon atoms as illustrated by cyclopropyl, cyclobutyl, cyclopentyl and cyclohexyl; and heterocyclyl refers to a 5 or 6 membered carbon based heterocycle, having from one to about three nitrogen atoms and/or one oxygen or sulfur atom, provided that no two oxygen and/or sulfur atoms are adjacent in the heterocycle. Examples include furyl, thienyl, pyridyl, oxadiazolyl, thiadiazolyl, triazinyl, pyrimidinyl and the like; and halo means bromo, chloro, iodo or fluoro.

As used herein, in hydroxyalkyl and alkoxyalkyl, the hydroxy and alkoxy groups can occur at any available position of alkyl. Thus hydroxyalkyl and alkoxyalkyl include, for example, hydroxymethyl, 1-hydroxyethyl, 2-hydroxyethyl, 2-hydroxypropyl, 2-hydroxyisopropyl, 2, 3, 4 and 5-hydroxy-pentyl and the like and corresponding alkyl ethers thereof.

As used herein, in hydroxyalkoxy, the hydroxy group can occur at any available position of alkoxy other than the C-1 position. Thus hydroxyalkoxy includes, for example, 2-hydroxyethoxy, 2-hydroxypropoxy, 2-hydroxyisopropoxy, 2 and 5-hydroxypentoxy and the like.

The compounds of formula I wherein $R_1$ is alkyl, alkoxy, cycloalkyl or alkoxyalkyl, Y, $R_2$, $R_3$ and $R_5$ are as defined hereinbefore, and $R_4$ is hydroxy, halomethyl, dihalomethyl, trihalomethyl, cycloalkyl, alkoxycarbonyl, alkoxyalkyl, alkane-carbonyloxyalkyl or 2,2,2-trifluoroethyl, can be prepared by a process which comprises reacting an amidoxime (N-hydroxy-carboximidamide) of the formula

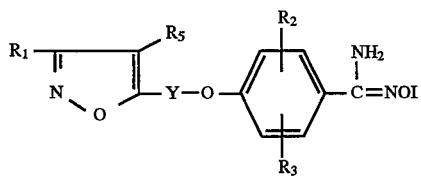

V with an acid halide, $R_4COX$, an alkyl haloformate, ROCOX (in the case where $R_4$ in formula I is hydroxy), where R is methyl or ethyl, or an acid anhydride, $(R_4CO)_2O$, where $R_1$, Y, $R_2$, $R_3$, $R_4$ and $R_5$ are as defined above in this paragraph and X is bromo, chloro, fluoro or iodo under anhydrous conditions to form the corresponding compound of formula I. The process involves the following methods. In one method, the amidoxime V is reacted with the acid halide or the acid anhydride in the presence of an organic or inorganic base, e.g., pyridine, triethylamine or potassium carbonate, in an inert solvent, e.g., acetone, methylene chloride, chloroform, toluene or tetrahydrofuran, or in a base which also functions as the solvent, e.g., pyridine, at an elevated temperature (about 40°–130° C.) or at a reduced temperature (about 0°–15° C.). In the latter case an intermediate O-acyl derivative [C(NH$_2$)=NOC(=O)—(R$_4$ or OR)] is isolated and heated at a temperature in the range of about 100°–130° C. for a time sufficient for cyclization to the oxadiazole of formula I to occur, generally about 5 minutes to 4 hours. In another method, the amidoxime V is reacted with the acid halide or acid anhydride in an acid which corresponds to the acid halide or acid anhydride at an elevated temperature (about 70°–100° C.).

The compounds of formula I where $R_1$ is alkyl, alkoxy, cycloalkyl or alkoxyalkyl, Y, $R_2$, $R_3$ and $R_5$ are as defined hereinbefore, and $R_4$ is dihalomethyl, trihalomethyl, cycloalkyl, alkoxyalkyl, alkanecarbonyloxyalkyl or 2,2,2-trifluoroethyl can be prepared by a process which comprises reacting amidoxime V with the product obtained by reaction of a carboxylic acid, $R_4CO_2H$, where $R_1$, Y, $R_2$, $R_3$ and $R_4$ are as defined above in this paragraph, with the coupling agent N,N'-carbonyldiimidazole, prepared as described in the examples, in an inert solvent, e.g., tetrahydrofuran, chloroform, methylene chloride or toluene, at an elevated temperature (about 40°–80° C.) to form the corresponding compound of formula I.

The compounds of formula I wherein $R_1$ is alkyl, alkoxy, cycloalkyl or alkoxyalkyl, Y, $R_2$ and $R_3$ are as defined hereinbefore, and $R_4$ is amino can be prepared by a process which comprises reacting amidoxime V, where $R_1$, Y, $R_2$, $R_3$ and $R_5$ are as defined above in this paragraph, with cyanogen halide, $CNX_1$, where $X_1$ is bromo, chloro or iodo, in the presence of a base, e.g., potassium or sodium bicarbonate, in an alcoholic solvent, e.g., ethyl alcohol, at about room temperature to give the compound of formula I where $R_4$ is amino.

The compounds of formula I where $R_1$ is alkyl, alkoxy, cycloalkyl or alkoxyalkyl, Y, $R_2$ and $R_3$ are as defined hereinbefore and $R_4$ is $CH_2CF_3$ and $R_5$ is hydrogen or alkyl can be prepared by reacting amidoxime V where $R_1$ is as defined above in this paragraph and Y, $R_2$, $R_3$ are as defined hereinbefore, with a ketene 1,3-propanedithiol acetal of the formula

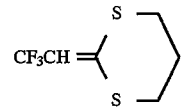

to give the corresponding compound of formula I.

The amidoxime V and ketene 1,3-propanedithiol acetal are reacted in the presence of silver trifluoroacetate in an inert solvent, e.g., tetrahydrofuran, dioxane, dimethylformamide or N-methylpyrrolidinone, at a temperature in the range of from about 60° to about 100° C. Preferably the reaction is carried out in the dark.

The intermediate amidoxime V is prepared according to the following flow sheet:

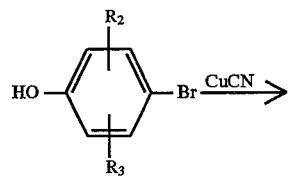

VI

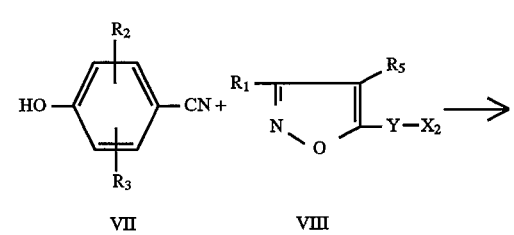

VII          VIII

-continued

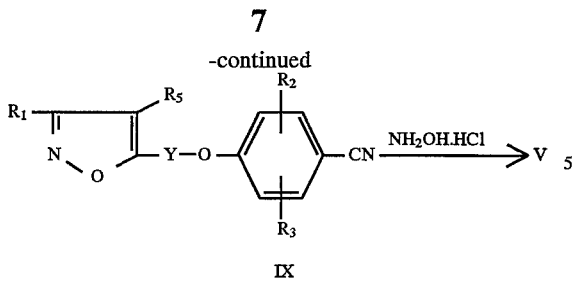

IX

The bromophenol VI reacts with the cuprous cyanide in an inert solvent at an elevated temperature, e.g., in dimethylformamide at reflux temperature to give the cyanophenol VII. The latter is reacted with haloisoxazole VIII, where $X_2$ is chloro, bromo or iodo, in a dry inert solvent, e.g., acetonitrile or N-methylpyrrolidinone, in the presence of a base, e.g., potassium carbonate or sodium hydroxide, optionally in the presence of a catalytic amount of potassium or sodium iodide, at an elevated temperature (50°–120° C.) to give cyano compound IX. The cyano compound IX reacts with the hydroxylamine hydrochloride in the presence of a base, e.g., potassium or sodium carbonate, sodium acetate or sodium hydroxide, in an alcoholic solvent, e.g., ethyl alcohol, at an elevated temperature (50°–150° C.) to give the amidoxime V.

Certain intermediate compounds of formula IX wherein $R_1$ is alkyl, cycloalkyl or alkoxyalkyl and Y, $R_2$ and $R_3$ are as defined hereinbefore can be prepared by reacting the ethinyl compound XII described hereinafter with a nitrile oxide, $R_1C\equiv N\rightarrow O$, where $R_1$ is as defined above in this paragraph, using a procedure similar to that described hereinafter for the preparation of compound I from the ethinyl compound III.

The intermediate bromophenols of formula VI and cyanophenols of formula VII belong to generically known classes of compounds and are readily prepared by known procedures.

The intermediate haloisoxazoles of formula VIII can be prepared by the procedure described in U.S. Pat. No. 4,843,087, i.e., by reacting an alkali metal derivative of an isoxazole of the formula

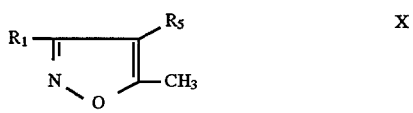

wherein $R_1$ is alkyl, alkoxy, trifluoromethyl, cycloalkyl or alkoxyalkyl, with a dihalide, $X_2$-Y'-$X_2$, where Y' is alkylene of 2 to 8 carbon atoms and $X_2$ is as defined above The alkali metal derivative is prepared in situ by treating isoxazole X with an organo-alkali metal base such as butyllithium or lithium diisopropylamide under anhydrous conditions.

The compounds of formula I wherein $R_1$ is alkyl, cycloalkyl or alkoxyalkyl, Y, $R_2$, $R_3$ and $R_5$ are as defined hereinbefore, and $R_4$ is alkoxy, trihalomethyl, cycloalkyl, alkoxycarbonyl, alkoxyalkyl or 2,2,2-trifluoroethyl, can be prepared by a process which comprises reacting an ethinyl compound of formula III hereinabove, wherein $R_6$ has the meaning defined above in this paragraph for $R_4$, with a nitrile oxide of the formula $R_1C\equiv N\rightarrow O$ which is prepared in situ from a hydroxyimino halide of the formula $R_1C(X_3)=$NOH, where $X_3$ is chlorine or bromine, in the presence of an amine base, e.g., triethylamine, pyridine or N-methylpyrrolidine. The hydroxyimino halides, which may also be prepared in situ, belong to a generically known class of compounds and are readily prepared by conventional procedures, e.g., by reacting the corresponding aldehyde oxime ($R_1C$=NOH) with a halogenating agent, e.g., N-chlorosuccinimide or bromine. The process for preparing the compounds of formula I by reacting the ethinyl compound of formula III takes place by heating the reactants in an inert polar solvent, e.g., dimethylformamide or N-methylpyrrolidone, at a temperature in the range of about 20° to about 120° C.

The intermediate ethinyl compounds of formula III are prepared according to the following flow sheet:

$$VII + HC\equiv C-Y-X_2 \longrightarrow HC\equiv C-Y-O-\underset{XI}{\overset{R_2}{\underset{R_3}{\bigcirc}}}-CN \xrightarrow{NH_2OH.HCl}$$

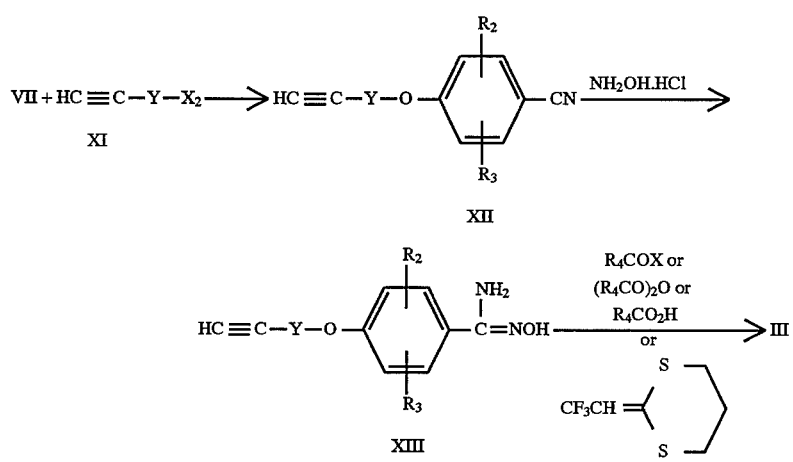

The cyanophenol VII is reacted with haloalkyne XI, where $X_2$ is as defined hereinbefore, using a procedure similar to that described above for the preparation of the cyano compound IX from compounds VII and VIII, to give the ethinyl compound of formula XII. Ethinyl compound XII is reacted with the hydroxylamine hydrochloride, using a procedure similar to that described above for the preparation of amidoxime V from cyano compound IX, to give the amidoxime of formula XIII. The amidoxime XIII is reacted with the acid halide $R_4COX$, acid anhydride $(R_4CO)_2O$, carboxylic acid $R_4CO_2H$ or

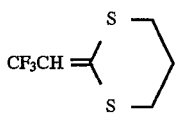

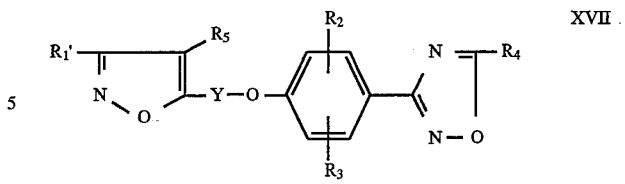

using procedures similar to those described hereinbefore for the preparation of compounds of formula I from amidoxime V.

The haloalkynes of formula XI belong to a generically known class of compounds.

The ethynyl compound XII can be acetylated using for example acetic anhydride, trifluoroacetylchloride, etc, giving the methyl or halomethyl ketone. This ketone is then reacted with a 2 moles of hydroxylamine to give the corresponding compound of formula V.

The compounds of formula I where $R_1$ is alkyl, alkoxy, cycloalkyl or alkoxyalkyl, Y, $R_2$ and $R_3$ are as defined hereinbefore, and $R_4$ is alkoxy, trihalomethyl, cycloalkyl, alkoxycarbonyl, alkoxyalkyl or 2,2,2-trifluoroethyl, can be prepared by a process which comprises reacting a phenol of the formula IV above wherein $R_2$ and $R_3$ are as defined hereinbefore and $R_7$ is as defined above in this paragraph for $R_4$, with a haloisoxazole of formula VIII above where $R_1$ is as defined above in this paragraph and Y and $X_2$ are as defined hereinbefore, to give the corresponding compound of formula I. The procedure used is similar to that described above for the preparation of cyano compound IX by reaction of cyanophenol VII and haloisoxazole VIII.

The intermediate haloisoxazole VIII can be prepared as described hereinbefore.

The intermediate phenols of formula IV can be prepared by reacting cyanophenol VII with hydroxylamine hydrochloride, using a procedure similar to that described hereinbefore for the preparation of amidoxime V from cyano compound IX, to give an amidoxime of the formula

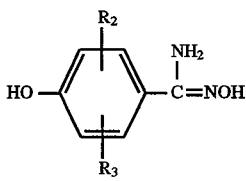

XIV

Amidoxime XIV is reacted with $R_4COX$, $(R_4CO)_2O$, $R_4CO_2H$ or

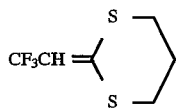

using procedures similar to those described hereinbefore for the preparation of compounds of formula I from amidoxime V, to give the corresponding phenol of formula IV.

The compounds of formula I wherein $R_1$ is hydroxyalkyl, Y, $R_2$, and $R_3$ are as defined hereinbefore, and $R_4$ is dihalomethyl, trihalomethyl, cycloalkyl, alkoxyalkyl, 2,2,2-trifluoroethyl or amino and $R_5$ is hydrogen or lower alkyl can be prepared from a compound of the formula wherein $R_1'$ is tert-butyldimethylsilyloxyalkyl [$(CH_3)_3CSi(Me)_2$—O—alkyl] and Y, $R_2$, $R_3$, $R_4$ and $R_5$ are as defined above in this paragraph, by cleaving the tert-butyldimethylsilyl ether.

Cleavage of the tert-butyldimethylsilyl ether is carried out by treating compound XVII as defined above, with strong organic acid, e.g., acetic acid or trifluoroacetic acid, or inorganic acid, e.g., hydrochloric acid or sulfuric acid, in an inert solvent, e.g., tetrahydrofuran or dioxane in the presence of water at a temperature in the range of from about 20° to about 60° C.

The compound of formula XVII where $R_4$ is dihalomethyl, trihalomethyl, cycloalkyl, alkoxyalkyl or 2,2,2-trifluoroethyl, can be prepared by a process which comprises reacting phenol IV wherein $R_2$ and $R_3$ are as defined hereinbefore, $R_5$ is hydrogen or lower alkyl and $R_7$ is as defined above in this paragraph for $R_4$, with an isoxazole of the formula

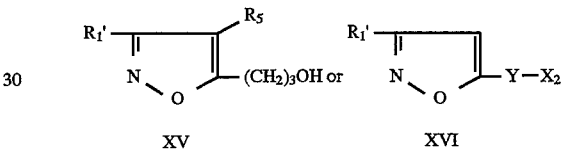

wherein $R_1'$, Y and $X_2$ are as defined hereinbefore.

The phenol IV is reacted with haloisoxazole XVI using a procedure similar to that described hereinbefore for the preparation of cyano compound IX from cyanophenol VII and haloisoxaozle VIII.

The phenol IV is reacted with isoxazole XV in the presence of diethyl azodicarboxylate (DEAD) and triphenylphosphine in an inert solvent, e.g., tetrahydrofuran, chloroform, dimethylformamide or N-methylpyrrolidinone, at a temperature in the range of from about −20° to about 20° C.

The intermediate phenol IV can be prepared by the procedure described hereinbefore.

The intermediate isoxazoles XV and XVI can be prepared by reacting isoxazole X, wherein $R_1$ is hydroxyalkyl, with tert-butyldimethylsilyl chloride to give the corresponding tert-butyldimethylsilyl ether of formula

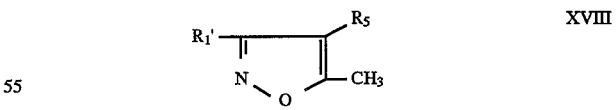

XVIII where $R_1'$ is as defined above, and $R_5$ is hydrogen or lower alkyl and reaction of an alkali metal derivative of compound XVIII with ethylene oxide or $X_2$-Y'-$X_2$ respectively.

Isoxazole X, wherein $R_1$ is hydroxyalkyl, is reacted with tert-butyl(dimethyl)silyl chloride in the presence of 4 (dimethylamino)pyridine and a base, e.g., triethylamine, pyridine or imidazole, in a dry inert solvent., e.g., methylene chloride, chloroform or tetrahydrofuran, at room temperature to give compound XVIII. Isoxazole XV is prepared by reacting an alkali metal derivative of compound XVIII with ethylene oxide, preferably in the presence of a chelating agent, e.g., N,N,N',N'-tetramethylethylenediamine or hexamethyl phosphoric triamide, in a dry inert solvent, e.g., tetrahydrofuran, at a temperature in the range of from about −78° to about 20° C. The alkali metal derivative is prepared in situ by reacting compound XVIII with an organo-alkali metal base, e.g., butyllithium or lithium diisopropylamide, under anhydrous conditions.

The compound of formula XVII, where $R_4$ is dihalomethyl, trihalomethyl, cycloalkyl, alkoxyalkyl or 2,2,2-trifluoroethyl, can also be prepared, as can the compound of that formula where $R_4$ is amino, according to the following flow sheet:

an alkyl haloformate, $R_8OCOX$, where X is as defined hereinbefore. The reaction takes place in a dry inert solvent, e.g., tetrahydrofuran or dioxane, at an initial temperature of about −78° to about −20° C. with subsequent warming to about 20° to about 25° C. The alkali metal derivative can be prepared in situ by reacting compound III with an organo-alkali metal, e.g., butyllithium or lithium diisopropylamide, under anhydrous conditions.

Certain compounds of formula I are intermediates for other compounds of formula I as described hereinafter.

The acid halides, alkyl haloformates and acid anhydrides used in the hereinbefore described processes for preparing

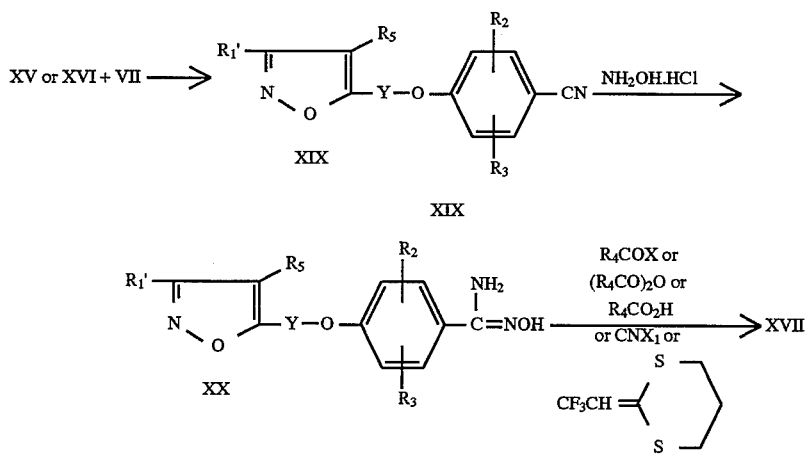

The reaction of compound XV or XVI with cyanophenol VII to give compound XIX is carried out by procedures similar to those described hereinbefore for preparing compound XVII by reacting phenol IV with isoxazole XV or haloisoxazole XVI respectively. The reaction of cyano compound XIX with hydroxylamine hydrochloride to give amidoxime XX, and the latter with the acid halide, acid anhydride, carboxylic acid, cyanogen halide or ketene 1,3-propanedithiol acetal to give compound XVII can be carried out by procedures similar to those described hereinbefore for preparing amidoxime V from cyano compound IX and for preparing the compound of formula I from amidoxime V.

The compounds of formula I wherein $R_1$ is hydroxy, Y, $R_2$ and $R_3$ are as defined hereinbefore, and $R_4$ is cycloalkyl or alkoxyalkyl can be prepared by reacting a compound of the formula

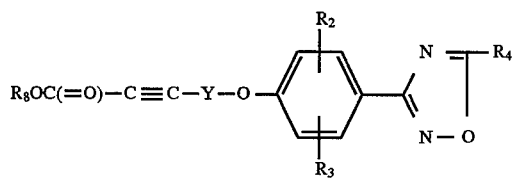

where $R_8$ is alkyl and Y, $R_2$, $R_3$ and $R_4$ are as defined above in this paragraph, with hydroxylamine hydrochloride to give the compound of formula I where $R_1$ is hydroxy.

Compound XXI is reacted with hydroxylamine hydrochloride in the presence of a base, e.g., sodium hydroxide, and water in an alcoholic solvent, e.g., methyl or ethyl alcohol, at a temperature in the range of from about 0° to about 25° C.

The intermediate compounds of formula XXI can be prepared by reacting an alkali metal derivative of compound III, wherein $R_6$ is as defined for $R_4$ of compound XXI, with the compounds of formula I and intermediates therefor, belong to well known classes of compounds and can be readily prepared by known procedures.

The compound of formula I wherein $R_1$ is alkyl, trifluoromethyl, cycloalkyl or alkoxyalkyl, Y, $R_2$, $R_3$ are as defined hereinabove, and $R_4$ is alkoxy or N=Q, where N=Q is alkylamino or dialkylamino, can be prepared from the corresponding compound of formula I wherein $R_4$ is trichloromethyl. In the case where $R_4$ is alkoxy, the trichloromethyl compound is reacted with an alkali metal alkoxide, e.g., sodium methoxide or sodium ethoxide, and in the case where $R_4$ is N=Q, with an amine(N=Q), in a suitable solvent, e.g., dimethylformamide or N-methylpyrrolidinone, at room temperature to give the corresponding compound of formula I where $R_4$ is alkoxy, alkylamino or dialkylamino.

The compounds of formula I wherein $R_1$ is hydroxyalkyl, Y, $R_2$ and $R_3$ are as defined hereinbefore, and $R_4$ is hydroxy, dihalomethyl, trihalomethyl, cycloalkyl, hydroxyalkyl, 2,2,2-trifluoroethyl or amino, can be prepared from the corresponding compound wherein $R_1$ is alkoxyalkyl by ether cleavage of the alkoxyalkyl moiety. The alkoxyalkyl compound is treated with trimethylsilyl iodide in a dry inert solvent, e.g., 1,2-dichloroethane, chloroform or acetonitrile, at a temperature in the range of from about 60° to about 80° C. to give the corresponding hydroxyalkyl compound.

The compounds of formula I wherein $R_1$ is alkyl, alkoxy, trifluoromethyl, cycloalkyl or alkoxyalkyl, Y, $R_2$ and $R_3$ are as defined hereinbefore, and $R_4$ is CON=Q, where N=Q is amino, alkylamino or dialkylamino, can be prepared by reacting the corresponding compound of formula I wherein $R_4$ is alkoxycarbonyl with amine N=Q in a polar solvent, e.g., ethyl alcohol or N-methylpyrrolidinone, at room temperature to give the corresponding compound where $R_4$ is CON=Q.

The compound of formula I where $R_1$ is alkyl, alkoxy, trifluoromethyl, cycloalkyl or alkoxyalkyl, Y, $R_2$ and $R_3$ are as defined hereinbefore, and $R_4$ is cyano, can be prepared from the corresponding compound wherein $R_4$ is CON=Q, where N=Q is amino, by treating the latter with trifluoroacetic anhydride in the presence of a base, e.g., pyridine or triethylamine, in a dry inert solvent, e.g., tetrahydrofuran, chloroform or 1,2-dichloroethane, at a temperature in the range of from about 0° to about 20° C.

The compounds of formula I wherein $R_1$ is alkoxy or hydroxyalkoxy, Y, $R_2$ and $R_3$ are as defined above, and $R_4$ is alkoxy, trihalomethyl, cycloalkyl, alkoxyalkyl, 2,2,2-trifluoro-ethyl or dialkylamino, can be prepared by etherification of the corresponding compound of formula I wherein $R_1$ is hydroxy. The etherification takes place by reacting the hydroxy compound with an alkyl halide or hydroxyalkyl halide, where halide is bromide, chloride or iodide, in the presence of a base, e.g., potassium carbonate or sodium carbonate, in an inert dry solvent, e.g., acetone, butanone or acetonitrile, at a temperature in the range of from about 50° to about 90° C.

The compounds of formula I wherein $R_1$ is alkyl, cycloalkyl, hydroxyalkyl, alkoxyalkyl or hydroxyalkoxy, Y, $R_2$ and $R_3$ are as defined hereinbefore, and $R_4$ is hydroxyalkyl can be prepared by transesterification of the corresponding compound of formula I wherein $R_4$ is alkanecarbonyloxyalkyl. The transesterification is carried out by treating the alkanecarbonyloxyalkyl compound with an inorganic or organic base, e.g., potassium carbonate, sodium bicarbonate or triethylamine, in an alcoholic solvent, e.g., methyl or ethyl alcohol, at room temperature.

The compounds of formula I wherein $R_1$ is alkyl, cycloalkyl or hydroxyalkyl, Y, $R_2$ and $R_3$ are as defined hereinbefore, and $R_4$ is hydroxyalkyl, can also be prepared by ether cleavage of the corresponding compound of formula I wherein $R_4$ is alkoxyalkyl. The ether cleavage can be carried out by treating the alkoxy compound with trimethylsilyl iodide using a procedure similar to that described hereinbefore for preparing the compound of formula I wherein $R_4$ is hydroxyalkyl.

The compound of formula I wherein $R_1$ is alkyl, alkoxy, cycloalkyl, hydroxyalkyl, alkoxyalkyl or hydroxyalkoxy, Y, $R_2$ and $R_3$ are as defined hereinbefore, and $R_4$ is iodomethyl, can be prepared from the corresponding compound of formula I wherein $R_4$ is chloromethyl by reaction with alkali metal iodide, e.g., sodium iodide. The reaction takes place by treating the chloromethyl compound with the alkali metal iodide, e.g., sodium or potassium iodide, in an inert solvent, e.g., acetone or butanone, at about 20° C.

The compounds of formula I wherein $R_1$ is alkyl, alkoxy, cycloalkyl or alkoxyalkyl, Y, $R_2$ and $R_3$ are as defined hereinbefore, and $R_4$ is (4-methylphenyl)sulfonyloxymethyl, are prepared from the corresponding compound of formula I wherein $R_4$ is hydroxymethyl by reaction with (4-methylphenyl)sulfonyl halide, where halide is bromide, chloride or iodide, in the presence of an inorganic base, e.g., potassium carbonate or sodium bicarbonate. The reaction takes place by reacting the reactants in an inert solvent, e.g., methylene chloride, chloroform or 1,2-dichloroethane, at about 20° C.

Compounds of formula I wherein $R_5$ is halo may be prepared from compounds of formula I wherein $R_5$ is hydrogen by standard halogenation methods known in the art; for example, addition of a halide, such as bromine in a suitable acid; glacial acetic acid for example, or other known methods.

Compounds of formula I wherein $R_5$ is alkyl may be prepared by alkylation of compounds of formula I where $R_5$ is hydrogen by known alkylation methods, such as, for example, addition of strong base, and then addition of suitable alkyl halide giving a compound of formula I or other well known methods.

It may be desirable to block or mask functionality of other groups present in the molecule, known to be susceptible to undesired halogenation or alkylation side reactions such as, for example hydroxy lower alkyl groups, carboxy groups, acetamido groups and the like, using conventional means known in the art, but this is well within the scope of practice of the skilled practitioner.

In the various processes described hereinabove for the preparation of the compounds of the invention, it will be appreciated that the reactions should be carried out for a time sufficient to provide the desired product and that for any specific reaction type, the time of the reaction will depend upon one or more factors such as, e.g., the nature of the reactants, the solvent employed and/or the temperature at which the reaction is carried out.

Once prepared, the antiviral compounds of the invention are formulated for use by preparing a dilute solution or suspension in a pharmaceutically acceptable aqueous, organic or aqueous-organic medium for topical or parenteral administration by intravenous or intramuscular injection, or for intranasal or ophthalmic application; or are prepared in tablet, capsule, or aqueous suspension form with conventional excipients for oral administration. As such, the compositions are useful in treating or preventing viral infection, especially picornaviral infection.

The structures of the compounds of the invention were established by modes of synthesis and elementary analysis, and by infrared, nuclear magnetic resonance and/or mass spectra.

The invention is further illustrated but not limited by the following examples.

EXAMPLE 1 a) 3-(3-Methylisoxazol-5-yl)propyl alcohol.

3,5-Dimethylisoxazole (220 g, 2.27 moles) in 2.2 L tetrahydrofuran under nitrogen was cooled with stirring to −75° C. and 908 mL of 2.5M n-butyllithium (2.27 moles) in hexanes were added over 1 hour keeping the temperature at or less than 65° C. The chilled solution was stirred for thirty minutes after addition was complete and was then treated at about −70° C. with a solution of 112 g (2.54 moles) of ethylene oxide in 390 ml tetrahydrofuran over a period of 1.5 hours, keeping the temperature at about −65° C. and stirred overnight. The mixture at 8° C. was quenched with continued cooling in an 8° C. bath by adding 1.2 L of 2.5M hydrochloric acid over a period of 20 minutes, during which time the temperature rose to 23° C., and was stirred for 10 minutes. The organic phase was separated, washed with 500 ml of water and concentrated to give 147 g of title compound as a brown oil. The combined aqueous phases (original+wash phase) were extracted with methyl tert-butyl ether (3×200 ml) and the combined organic extracts were concentrated to give an additional 125 g of title compound as a brown oil.

b) 3-(3-Methylisoxazol-5-yl)propyl chloride.

To the product from part (a) (125 g, 0.885 mole) in 1225 ml methylene chloride was added 192 ml (2.63 moles) of thionyl chloride over a period of 1 hour during which time the temperature rose to 40° C. to a gentle reflux. Heating at reflux was continued for 3 hours, the reaction mixture was allowed to stand overnight, and then heating at reflux was continued for 1 hour. The reaction mixture was added as a steady stream to 3 kg of ice water with vigorous stirring, stirring was continued for 1 hour and the aqueous phase was separated. Water (1 L) was added to the organic phase followed by 161 g of solid sodium bicarbonate in portions with vigorous stirring. The organic phase was separated and concentrated in vacuo to give a black oil which was purified by wipe-film distillation to give 94 g of the title compound as a yellow oil, bp 65° C./0.09 mm.

c) 3,5-Dimethyl-4-[3-(3-methylisoxazol-5-yl)propyloxy]benzo-nitrile.

A mixture of 3,5-dimethyl-4-hydroxybenzonitrile (7.36 g, 50.0 mmol), dry N-methylpyrrolidinone (100 mL), milled potassium carbonate (13.8 g, 100 mmol), potassium iodide (0.84 g, 5.0 mmol), and the product from part (b) (12.0 g, 75.0 mmol) was stirred at 60° C. for 18 hours. After cooling to room temperature, the mixture was partitioned between 200 mL water and 100 mL ethyl acetate. The aqueous layer was extracted twice with 50 mL portions of ethyl acetate. The combined organic extracts were washed with water, brine, dried ($MgSO_4$), and concentrated in vacuo to provide 18.3 g of a yellow oil. MPLC (Silica Gel 60 50×460 mm, 25% ethyl acetate in hexanes) provided 12.7 g (94.1%) of pure title compound as a white solid, m.p. 46°–48° C. (methanol).

d) 3,5-Dimethyl-4-[3-(3-methylisoxazol-5-yl)propyloxy]-N-hydroxybenzenecarboximidamide.

A mixture of the product prepared according to part (c) (18.4 g, 68.1 mmol), absolute ethanol (200 mL), milled potassium carbonate (46.9 g, 0.340 mol), and hydroxylamine hydrochloride (23.6 g, 0.340 mol) was refluxed for 18 hours. The hot mixture was filtered and the solids remaining washed with hot ethanol. The combined filtrates were concentrated in vacuo to provide 19.4 g (93.9%) of the title compound as a white powder which was of sufficient purity to be used in subsequent steps. A sample was recrystallized from ethanol to give a white solid, m.p. 129°–130.5° C.

e) 5-{3-[2,6-Dimethyl-4-(5-trifluoromethyl-1,2,4-oxadiazol-3-yl)phenoxy]propyl}-3-methylisoxazole [I; $R_1=CH_3$, $Y=(CH_2)_3$, $R_2$ and $R_3=2,6-(CH_3)_2$, $R_4=CF_3$, $R_5=$hydrogen].

To a solution of the product from part (d) (4.38 g, 14.4 mmol) in 8.0 mL dry pyridine was added 4.07 mL (28.8 mmol) of trifluoroacetic anhydride at a rate to maintain a gentle reflux. After addition was complete, the mixture was allowed to cool to room temperature, and diluted with water. The solids obtained were washed with water, dried in vacuo, and purified by chromatography (Silica Gel 60, 15–40% ethyl acetate in hexanes), to give 4.76 g of pure title compound as a white solid, m.p. 61°–62° C.

EXAMPLE 2 a) 3,5-Difluoro-4-hydroxybenzonitrile.

A mixture of 4-bromo-2,6-difluorophenol (4.00 g, 19.0 mmol), copper (I) cyanide (1.72 g, 19.0 mmol), and dimethylformamide (40 mL) was refluxed for 6 hours, cooled to room temperature, diluted with water (150 mL), and filtered. The tan solids obtained were washed with water and retained. The combined filtrates were acidified (1N HCl) and extracted with ethyl acetate. The combined organic extracts were dried ($MgSO_4$), concentrated in vacuo, and purified by flash chromatography (Silica Gel 60, 20% ethyl acetate in hexanes) to give 1.03 g of pure title compound as an off-white solid, mp 195°–197° C.

The tan solid was suspended in ethyl acetate with a small amount of acetone, filtered, and concentrated in vacuo. The residue obtained was partitioned between ethyl acetate and 1N HCl. The aqueous phase was extracted with ethyl acetate and the combined organic phases purified as above to provide an additional 0.43 g (49% combined yield) of pure title compound.

The following compounds were prepared by a procedure similar to that of Example 1(c):

| Example | Compound |
| --- | --- |
| 2b | 3,5-Difluoro-4-[3-(3-methylisoxazol-5-yl)propyl-oxy]benzonitrile, mp 23–24.5° C. (ether/hexanes) - prepared from 3,5-difluoro-4-hydroxybenzonitrile and the product of Example 1b; yield 49.1%. |
| 3a | 3,5-Dichloro-4-[3-(3-methylisoxazol-5-yl)propyl-oxy]benzonitrile, mp 69.5–70.5° C. (methanol) (white solid) - prepared from 3,5-dichloro-4-hydroxy-benzonitrile and the product of Example 1b; yield 80.7%. |

The following compounds were prepared by a procedure similar to that of Example 1d:

| Example | Compound |
| --- | --- |
| 2c | 3,5-Difluoro-4-[3-(3-methylisoxazol-5-yl)propyl-oxy]-N-hydroxybenzenecarboximidamide, mp 122–124° C. - prepared from the product of Example 2b; yield 86%. The crude product was purified by suspension in 10% ethanol in chloroform, filtration, concentration in vacuo and trituration of the resulting white solid in cold chloroform. |
| 3b | 3,5-Dichloro-4-[3-(3-methylisoxazol-5-yl)propyl-oxy]-N-hydroxybenzenecarboximidamide - prepared from the product of Example 3a (0.5 g). The product (0.78 g), obtained on concentration of the filtrates as an oily solid, was used in the next step. |

The following compounds were prepared by a procedure similar to that of Example 1e:

| Example | Compound |
| --- | --- |
| 2d | 5-{3-[2,6-Difluoro-4-(5-trifluoromethyl-1,2,4-oxadiazol-3-yl)phenoxy]propyl}-3-methylisoxazole [I; $R_1 = CH_3$, $Y = (CH_2)_3$, $R_2$ and $R_3 = 2,6$-$(F)_2$, $R_4 = CF_3$, $R_5 = $ hydrogen], mp 36–37° C. (hexanes) (white solid) - from the product of Example 2c and trifluoroacetic anhydride; yield 44.5%. |
| 3c | 5-{3-[2,6-Dichloro-4-(5-trifluoromethyl-1,2,4-oxadiazol-3-yl)phenoxy]propyl}-3-methylisoxazole [I; $R_1 = CH_3$, $Y = (CH_2)_3$, $R_2$ and $R_3 = 2,6$-$(Cl)_2$, $R_4 = CF_3$, $R_5 = $ hydrogen], mp 65–67° C. (hexanes) (white solid) - from the product of Example 3b and trifluoroacetic anhydride; yield 80.5%. |
| 4 | 5-{3-[4-(5-Cyclopropyl-1,2,4-oxadiazol-3-yl)-2,6-dimethylphenoxy]propyl}-3-methylisoxazole [I; $R_1 = CH_3$, $Y = (CH_2)_3$, $R_2$ and $R_3 = 2,6$-$(CH_3)_2$, $R_4 = $ cyclo-propyl, $R_5 = $ hydrogen), mp 85–88° C. (methanol) (white solid) - from the product of Example 1d and cyclopropane-carbonyl chloride; yield 71.0%. |
| 5 | 5-{3-[2,6-Dimethyl-4-(5-methoxymethyl-1,2,4-oxadiazol-3-yl)phenoxy]propyl}-3-methylisoxazole [I; $R_1 = CH_3$, $Y = (CH_2)_3$, $R_2$ and $R_3 = 2,6$-$(CH_3)_2$, $R_4 = CH_2OCH_3$, $R_5 = $ hydrogen], mp 63–64° C. (ether/hexane) (white solid) - from the product of Example 1d and methoxy-acetyl chloride; yield 76.1%. |
| 6 | 5-{3-[2,6-Dimethyl-4-(5-fluoromethyl-1,2,4-oxadiazol-3-yl)phenoxy]propyl}-3-methylisoxazole [I; $R_1 = CH_3$, $Y = (CH_2)_3$, $R_2$ and $R_3 = 2,6$-$(CH_3)_2$, $R_4 = CH_2F$, $R_5 = $ hydrogen], mp 80–80.5° C. (methanol) (white solid) - from the product of Example 1d and fluoroacetyl chloride; yield 45.6%. |
| 7 | 5-{3-[2,6-Dimethyl-4-(5-ethoxycarbonyl-1,2,4-oxadiazol-3-yl)phenoxy]propyl}-3-methylisoxazole [I; $R_1 = CH_3$, |

| Example | Compound |
|---|---|
| | Y = (CH$_2$)$_3$, R$_2$ and R$_3$ = 2,6-(CH$_3$)$_2$, R$_4$ = CO$_2$CH$_2$CH$_3$, R$_5$ = hydrogen], mp 105–106° C. (ethyl acetate/hexane) (white solid) - from the product of Example 1d and ethyl oxalyl chloride; yield 67.8%. |

EXAMPLE 8

5-{3-[2,6-Dimethyl-4-(5-oxo-4,5-dihydro-1,2,4-oxadiazol-3-yl)phenoxy]propyl}-3-methylisoxazole [tautomer of I where R$_1$=CH$_3$, Y=(CH$_2$)$_3$, R$_2$ and R$_3$=2,6-(CH$_3$)$_2$, R$_4$=OH, R$_5$=hydrogen].

To a chilled (0° C.) suspension of the product from Example 1d (3.03 g, 10.0 mmol), dry acetone (30 mL) and finely divided potassium carbonate (1.52 g, 11 mmol) was added dropwise a solution of ethyl chloroformate (1.05 mL, 11.0 mmol) in acetone (5.5 mL). After stirring at 0° C. for 1 hour, the reaction mixture was diluted with water (100 mL) and extracted with methylene chloride (3×25 mL). The combined organic extracts were washed with brine, dried (MgSO$_4$), filtered through a short column of Florisil, and concentrated in vacuo to give the crude intermediate O-acyl derivative as an off-white solid which was then heated at 120°–130° C. for 45 minutes to give the title compound (2.38 g, 75.4%), mp −194°–195° C. (methanol) (white needles).

The following compounds were prepared by a procedure similar to that of Example 8:

| Example | Compound |
|---|---|
| 9 | 5-{3-[2,6-Dimethyl-4-(5-methylcarbonyloxy-methyl-1,2,4-oxadiazol-3-yl)phenoxy]propyl}-3-methylisoxazole [I; R$_1$ = CH$_3$, Y = (CH$_2$)$_3$, R$_2$ and R$_3$ = 2,6-(CH$_3$)$_2$, R$_4$ = CH$_2$OCOCH$_3$, R$_5$ = hydrogen], mp 71–73° C. (ether/hexanes) (white solid) - from the product of Example 1d and acetoxyacetyl chloride; yield 71.3%. The crude product was purified by chromatography (Silica Gel 60, 35% ethyl acetate in hexanes). |
| 10 | 5-{3-[4-(5-Chloromethyl-1,2,4-oxadiazol-3-yl)-2,6-dimethylphenoxy]propyl}-3-methylisoxazole [I; R$_1$ = CH$_3$, Y = (CH$_2$)$_3$, R$_2$ and R$_3$ = 2,6-(CH$_3$)$_2$, R$_4$ = CH$_2$Cl, R$_5$ = hydrogen], mp 75–76° C. (methanol) (white solid) - from the product of Example 1d and chloroacetyl chloride. The crude product was purified by chromatography (Silica Gel 60, 20% ethyl acetate in hexanes); yield 76.2%. |
| 11 | 5-{3-[2,6-Dimethyl-4-(5-(1-methylcarbonyloxy-ethyl)-1,2,4-oxadiazol-3-yl)phenoxy]propyl}-3-methylisoxazole [I; R$_1$ = CH$_3$, Y = (CH$_2$)$_3$, R$_2$ and R$_3$ = 2,6-(CH$_3$)$_2$, R$_4$ = CH(CH$_3$)OCOCH$_3$, R$_5$ = hydrogen], mp 77–77.5° C. (white solid) - from the product of Example 1d and 2-acetoxypropionyl chloride; yield 64.6%. |

EXAMPLE 12

5-{3-[2,6-Dimethyl-4-(5-trichloromethyl-1,2,4-oxadiazol-3-yl)-phenoxy]propyl}-3-methylisoxazole [I; R$_1$=CH$_3$, Y=(CH$_2$)$_3$, R$_2$ and R$_3$=2,6-(CH$_3$)$_2$, R$_4$=CCl$_3$, R$_5$=hydrogen].

Trichloroacetic acid (22.8 g, 140 mmol) was added to the product of Example 1d (10.6 g, 34.8 mmol) and heated at 85° C. until a thick solution was obtained. Trichloroacetyl chloride (14.5 mL, 69.6 mmol) was added in three equal portions. A vigorous reaction ensued after addition of the first portion. The mixture was heated an additional hour at 94° C. The cooled mixture was diluted with water and extracted with ethyl acetate (3×25 mL). The combined organic phases were washed with saturated sodium bicarbonate, brine, dried (MgSO$_4$) and concentrated in vacuo to give 10.1 g of orange oil. Chromatography (Silica Gel 60, methylene chloride) provided 6.94 g of yellow oil which was crystallized from methanol to give 5.03 g of pure title compound as white needles, mp 77°–77.5° C.

EXAMPLE 13

5-{3-[4-(5-Dichloromethyl-1,2,4-oxadiazol-3-yl)-2,6-dimethyl-phenoxy]propyl}-3-methylisoxazole [I; R$_1$=CH$_3$, Y=(CH$_2$)$_3$, R$_2$ and R$_3$=2,6-(CH$_3$)$_2$, R$_4$=CHCl$_2$, R$_5$=hydrogen].

Dichloroacetic acid (1.24 mL, 15.0 mmol) was added to the product of Example 1d (1.14 g, 3.76 mmol) and heated at 85° C. until a solution was obtained. Dichloroacetic anhydride (1.14 mL, 7.52 mmol) was added dropwise rapidly and stirred at 85° C. for an additional hour. Work-up as described for Example 12 provided 1.51 g of yellow-brown oil which was purified by chromatography (Silica Gel 60, 25% ethyl acetate in hexanes) to give 1.37 g (91.3%) of pure title compound as a pale yellow oil which solidified upon standing, mp 52°–3° C. (ethanol).

EXAMPLE 14

5-{3-[4-(5-Difluoromethyl-1,2,4-oxadiazol-3-yl)-2,6-dimethyl-phenoxy]propyl}-3-methylisoxazole [I; R$_1$=CH$_3$, Y=(CH$_2$)$_3$, R$_2$ and R$_3$=2,6-dimethyl, R$_4$=CHF$_2$, R$_5$=hydrogen).

Difluoroacetic acid (0.31 mL, 5.0 mmol) was added to a cold (−25° C.) solution of 1,1'-carbonyldiimidazole (0.80 g, 5.0 mmol) in dry tetrahydrofuran (5.0 mL). After 5 minutes, the resulting suspension was added dropwise rapidly to a solution of the product of Example 1d in dry tetrahydrofuran (20 mL). The mixture was refluxed for 2 hours, cooled, diluted with water, and extracted with ethyl acetate (3×). The combined organic phases were washed with water, brine, dried (MgSO$_4$), and concentrated in vacuo to give 0.78 g of a pale yellow solid. Chromatography (Silica Gel 60, 30% ethyl acetate in hexanes) provided 0.55 g of pure title compound as a pale yellow oil which solidified upon standing, mp 70.5°–71° C. (methanol).

EXAMPLE 15

5-{3-[4-(5-Imino-4,5-dihydro-1,2,4-oxadiazol-3-yl)-2,6-dimethylphenoxy]propyl}-3-methylisoxazole [tautomer of I where R$_1$=CH$_3$, Y=(CH$_2$)$_3$, R$_2$ and R$_3$=2,6-(CH$_3$)$_2$, R$_4$=NH$_2$, R$_5$=hydrogen].

Cyanogen bromide (1.17 g, 11.0 mmol) was added in portions to a mixture of the product of Example 1d (3.03 g, 10.0 mmol) and potassium bicarbonate (1.10 g, 11.0 mmol) in 50% aqueous ethanol (8.0 mL). After 15 minutes, the thick yellow suspension was diluted with water and filtered. The yellow solid obtained was washed with water and ether to give 1.48 g (45.1%) of pure title compound as a yellow powder, mp 175°–183° C.

EXAMPLE 16

5-{3-[2,6-Dimethyl-4-(5-methoxy-1,2,4-oxadiazol-3-yl)phen-oxy]propyl}-3-methylisoxazole [I; R$_1$=CH$_3$, Y=(CH$_2$)$_3$R$_2$ and R$_3$=2,6-(CH$_3$)$_2$, R$_4$=OCH$_3$R$_5$=hydrogen].

The product of Example 12 (627 mg, 1.46 mmol) was added to a freshly prepared solution of sodium methoxide in methanol (1.5 equivalents sodium in 5 mL methanol) in dry dimethylformamide (3–5 mL) and the mixture was stirred at room temperature for 15–30 minutes. The reaction mixture was diluted with water and extracted with ethyl acetate (3×). The combined organic extracts were washed with water, brine, dried (MgSO$_4$) and concentrated in vacuo. The crude residue (0.64 g) was purified by chromatography (Silica Gel 60, first with 2% methanol in methylene chloride followed by 5% ethyl acetate in methylene chloride) to give pure title compound (308 mg) as a colorless oil which crystallized from methanol, mp 64.5°–65.5° C. (white solid).

EXAMPLE 17

5-{3-[2,6-Dimethyl-4-(5-ethoxy-1,2,4-oxadiazol-3-yl]phenoxy]propyl}-3-methylisoxazole [I; R$_1$=CH$_3$, Y=(CH$_2$)$_3$R$_2$ and R$_3$=2,6-(CH$_3$)$_2$, R$_4$=OCH$_2$CH$_3$R$_5$=hydrogen].

Following the procedure of Example 16 but using sodium ethoxide in ethanol in place of sodium methoxide in methanol there was obtained from the product of Example 12 (905 mg, 2.10 mmol) a crude residue (0.82 g) which was purified by chromatography (Silica Gel 60, 2% ethyl acetate in methylene chloride) to give 0.52 g (69%) of pure title compound as a yellow solid, mp 70°–72.5° C. (ethanol).

EXAMPLE 18

5-{3-[2,6-Dimethyl-4-(5-methylimino-4,5-dihydro-1,2,4-oxadiazol-3-yl)phenoxy]propyl}-3-methylisoxazole [tautomer of I where R$_1$=CH$_3$, Y=(CH$_2$)$_3$, R$_2$ and R$_3$=2,6-(CH$_3$)$_2$, R$_4$=NHCH$_3$, R$_5$=hydrogen].

The product of Example 12 (1.00 g, 2.32 mmol) was added to 5 ml of 40% aqueous methylamine in dimethylformamide (3–5 mL) and the mixture was stirred at room temperature for 18 hours. The reaction mixture was diluted with water and extracted with ethyl acetate (3×). The combined organic extracts were washed with water, brine, dried (MgSO$_4$) and concentrated in vacuo. The crude residue (0.54 g) was purified by chromatography (Silica Gel 60, first with 2% methanol in methylene chloride and then with 50% ethyl acetate in hexanes) to give 300 mg (37.5%) of pure title compound as a yellow solid, mp 126.5°–127° C. (ethanol).

EXAMPLE 19

5-{3-[2,6-Dimethyl-4-(5-dimethylamino-1,2,4-oxadiazol-3-yl)-phenoxy]propyl)-3-methylisoxazole [I; R$_1$=CH$_3$, Y=(CH$_2$)$_3$, R$_2$ and R$_3$=2,6-(CH$_3$)$_2$, R$_4$=N(CH$_3$)$_2$, R$_5$=hydrogen].

Following the procedure of Example 18 but using 40% aqueous dimethylamine in place of 40% aqueous methylamine and reducing the reaction time to 15–30 minutes, there was obtained from the product of Example 12 (0.97 g, 2.2 mmol) a crude residue (0.75 g) which was purified by chromatography (Silica Gel 60, 50% ethyl acetate/hexanes) to give 0.70 g (84%) of pure title compound as a pale yellow solid, mp 123°–124° C. (ethanol).

EXAMPLE 20 a) 3,5-Dimethyl-4-(3-ethinylpropoxy)benzonitrile.

Following the procedure of Example 1c and using 14.7 g (100 mmol) of 3,5-dimethyl-4-hydroxybenzonitrile and substituting 5-chloro-1-pentyne (12.7 mL, 120 mmol) for the product of Example 1b, there was obtained a red-brown oil which was purified by chromatography (Silica Gel 60, 15% ethyl acetate in hexanes) to give pure title compound (21.2 g, 99.4%) as a pale yellow oil.

b) 3,5-Dimethyl-4-(3-ethinylpropoxy)-N-hydroxybenzene-carboximidamide.

Following the procedure of Example 1d and using 13.0 g (61.0 mmol) of the product from part (a), there was obtained the title compound (14.9 g, 99.3%) as a white solid which was sufficiently pure for use in the next step.

c) 3-[3,5-Dimethyl-4-(3-ethinylpropoxy)phenyl]-5-trifluoromethyl-1,2,4-oxadiazole.

Following the procedure of Example 1e and using 7.40 g (30.0 mmol) of the product of part (b), 9.0 mL of dry pyridine and 8.50 mL of trifluoroacetic anhydride there was obtained pure title compound (6.42 g, 65.9%) as a pale yellow oil which crystallized from methanol to give the title compound as a white solid, mp 45.5°–48° C.

Procedure 1—general procedure for preparing the compounds of Examples 21, 22, 23, 28a and 29a below To a solution of N-chlorosuccinimide (NCS, 1.8–2.5 equivalents) in dry N,N-dimethylformamide or N-methylpyrrolidinone (1.6–3.0 mL per mmol NCS) and 1–2 drops of pyridine was added dropwise a solution of oxime (1.8–2.5 equivalents) in the same solvent (0.40–0.80 mL per mmol oxime). The internal temperature was maintained at 25°–30° C. with a 25° C. water bath. After 1 hour at room temperature, a solution of the appropriate ethinyl compound (formula III or XII) (1 equivalent) in the same solvent (0.80 mL per mmol the ethinyl compound) was added. The reaction mixture was heated to 85°–90° C. and a solution of triethylamine (TEA, 1.8–2.5 equivalents) in the same solvent (0.80–1.6 mL per mmol TEA) was added dropwise over 45–90 minutes. After an additional hour at 85°–90° C., the mixture was cooled to room temperature, diluted with water, and extracted with ethyl acetate (3×). The combined organic phases were washed with 10% KHSO$_4$, water, brine, dried (MgSO$_4$ or Na$_2$SO$_4$) and concentrated in vacuo. The crude product was purified by chromatography (Silica Gel 60, 15–40% ethyl acetate in hexanes).

The following compounds were prepared by Procedure 1:

| Example | Compound |
|---|---|
| 21 | 5-{3-[2,6-Dimethyl-4-(5-trifluoromethyl-1,2,4-oxadiazol-3-yl)phenoxy]propyl}-3-(methoxymethyl)-isoxazole [I; R$_1$ = CH$_2$OCH$_3$, Y = (CH$_2$)$_3$, R$_2$ and R$_3$ = 2,6-(CH$_3$)$_2$, R$_4$ = CF$_3$, R$_5$ = hydrogen], colorless oil (yield 70.1%) - from the product of Example 20c (2.00 g, 6.17 mmol) and methoxyacetaldehyde oxime (1.10 g, 12.3 mmol). |
| 22 | 5-{3-[2,6-Dimethyl-4-(5-trifluoromethyl-1,2,4-oxadiazol-3-yl)phenoxy]propyl}-3-(ethoxymethyl)-isoxazole [I; R$_1$ = CH$_2$OCH$_2$CH$_3$, Y = (CH$_2$)$_3$, R$_2$ and R$_3$ = 2,6-(CH$_3$)$_2$, R$_4$ = CF$_3$, R$_5$ = hydrogen], mp 24–25° C. (methanol) (white powder) (yield 35.3%) - from the product of Example 20c (2.00 g, 6.17 mmol) and 2-ethoxyacetaldehyde oxime (1.27 g, 12.3 mmol). |
| 23 | 3-Cyclopropyl-5-{3-[2,6-dimethyl-4-(5-trifluoromethyl-1,2,4-oxadiazol-3-yl)phenoxy]propyl}-isoxazole [I; R$_1$ = cyclopropyl, Y = (CH$_2$)$_3$, R$_2$ and R$_3$ = 2,6-(CH$_3$)$_2$, R$_4$ = CF$_3$, R$_5$ = hydrogen), mp 63.5–65° C. (ethanol) (white needles) (yield 82%) - from the product of Example 20c (0.92 g, 2.8 mmol) and cyclopropylcarboxaldehyde oxime (0.48 g, 5.6 mmol). |

2=Ethoxyacetaldehyde oxime (used in Example 22 above)

A solution of hydroxylamine hydrochloride (18.8 g, 0.270 mol), ethanol (25 mL), water (40 mL) and 1,1,2-triethoxyethane was warmed at 45° C. for 30 minutes, cooled to room temperature, and extracted with ether (3×).

The combined organic phases were dried (MgSO$_4$), concentrated in vacuo, and filtered through a small plug of cotton to give 10.1 g of title compound as a pale yellow oil which was used as is.

EXAMPLE 24

5-Cyclopropyl-3-[3,5-dimethyl-4-(3-ethinylpropoxy)phenyl]-1,2,4-oxadiazole.

Following the procedure of Example 1e and using 5.00 g (20.3 mmol) of the product of Example 20b, 75 mL of dry pyridine and 2.77 mL (30.5 mmol) of cyclopropylcarbonyl chloride there was obtained pure title compound (3.98 g, 66.2%) as a nearly colorless oil which solidified on standing, mp 45°–46° C. (methanol).

Procedure 2—general procedure for preparing the compounds of Examples 25, 26 and 27 below To a chilled (0° C.) solution of the appropriate aldehyde oxime (2.5 equivalents) in dry dimethylformamide (DMF) (15 mL) was added in 1 portion N-chlorosuccinimide (NCS) (2.5 equivalents). After 1–2 hours, the product from Example 24 (1 equivalent) was added and the whole heated to 80° C. A solution of triethylamine (2.5 equivalents) in dry DMF (5 mL) was added dropwise over 90 minutes. The mixture was heated an additional 18 hours. Work up and purification as described for Example 21 provided the pure product.

The following compounds were prepared by Procedure 2:

| Example | Compound |
|---|---|
| 25 | 5-{3-[4-(5-Cyclopropyl-1,2,4-oxadiazol-3-yl)-2,6-dimethylphenoxy]propyl}-3-ethylisoxazole [I; R$_1$ = CH$_2$CH$_3$, Y = (CH$_2$)$_3$, R$_2$ and R$_3$ = 2,6-(CH$_3$)$_2$, R$_4$ = cyclopropyl, R$_5$ = hydrogen], colorless oil - from the product of Example 24 and propionaldehyde oxime; yield 67%. |
| 26 | 5-{3-[5-(Cyclopropyl-1,2,4-oxadiazol-3-yl)-2,6-dimethylphenoxy]propyl}-3-methoxymethyl)-isoxazole [I; R$_1$ = CH$_2$OCH$_3$, Y = (CH$_2$)$_3$, R$_2$ and R$_3$ = 2,6-(CH$_3$)$_2$, R$_4$ = cyclopropyl, R$_5$ = hydrogen], mp 44–45° C. (methanol) (white solid) - from the product of Example 24 and methoxyacetaldehyde oxime; yield 26.1% (from combination of two runs). |
| 27 | 3-Cyclopropyl-5-{3-[5-(cyclopropyl-1,2,4-oxadiazol-3-yl)-2,6-dimethylphenoxy]propyl}isoxazole [I; R$_1$ = R$_4$ = cyclopropyl, Y = (CH$_2$)$_3$, R$_2$ and R$_3$ = 2,6-(CH$_3$)$_2$], mp 59–60° C. (methanol) (white solid) - from the product of Example 24 and cyclopropylcarboxaldehyde oxime; yield 60.4%. |

EXAMPLE 28 a) 3,5-Dimethyl-4-[3-(3-ethylisoxazol-5-yl)propyloxy]benzo-nitrile.

Following Procedure 1 above but omitting the pyridine and using propionaldehyde oxime (8.6 g, 118 mmol) and the product of Example 20a (10.1 g, 47.0 mmol) there was obtained 4.90 g (36.7%) of pure title compound, mp 53.5°–54.5° C. (ethanol).

b) 3,5-Dimethyl-4-[3-(3-ethylisoxazol-5-yl)propyloxy]-N-hydroxybenzenecarboximidamide.

A mixture of the product from part (a) (2.01 g, 7.50 mmol), ethanol (20 mL), hydroxylamine hydrochloride (2.61 g, 37.5 mmol), and finely divided potassium carbonate (5.20 g, 37.5 mmol) was refluxed for 18 hours. The mixture was filtered hot, the filter cake washed with ethanol, and the combined filtrates concentrated in vacuo to give 2.57 g of crude title compound as a pasty yellow solid, which was used as such in the next step.

c) 5-{3-[2,6-Dimethyl-4-(5-trifluoromethyl-1,2,4-oxadiazol-3-yl)phenoxy]propyl}-3-ethylisoxazole [I; R$_1$=CH$_2$CH$_3$, Y=(CH$_2$)$_3$, R$_2$ and R$_3$=2,6-(CH$_3$)$_2$, R$_4$=CF$_3$, R$_5$=hydrogen].

All the product from part (b) was dissolved in pyridine (2.3 mL) and trifluoroacetic anhydride (2.1 mL, 15 mmol) was added dropwise. The mixture was refluxed for 1 hour, cooled to room temperature, diluted with water, and extracted with methylene chloride (3×). The combined organic phases were washed with 1N HCl, water, brine, dried (MgSO$_4$), and concentrated in vacuo. The pale yellow oil obtained (2.15 g) was chromatographed (Silica Gel 60, methylene chloride) to give 2.10 g (70.7%) of pure title compound as a white solid, mp 157°–158° C. (methanol).

EXAMPLE 29 a) 3,5-Dimethyl-4-{3-[3-(2-methoxyethyl)isoxazol-5-yl]propyloxy}benzonitrile.

Following Procedure 1 above and using 3-methoxypropionaldehyde oxime (1.94 g, 18.8 mmol) and the product of Example 20a (2.20 g, 10.3 mmol) there was obtained 1.51 g (46.5%) pure title compound as a colorless oil which crystallized from ethanol as fine white needles, mp 64°–64.5° C. There was recovered 0.89 g (40.4%) of starting product of Example 20a.

b) 5-{3-[2,6-Dimethyl-4-(5-trifluoromethyl-1,2,4-oxadiazol-3-yl)phenoxy]propyl}-3-(methoxyethyl)isoxazole [I; R$_1$=CH$_2$CH$_2$OCH$_3$, Y=(CH$_2$)$_3$, R$_4$=CF$_3$, R$_5$=hydrogen].

Sodium (442 mg, 19.2 mmol) was dissolved in dry methanol (20 mL) contained in an addition funnel. This solution was added dropwise to a solution of hydroxylamine hydrochloride (1.34 g, 19.2 mmol) in dry methanol (10 mL). A fine white precipitate formed. After 1 hour, a solution of the product from part (a) (1.21 g, 3.85 mmol) in dry methanol (5 mL) was added and the mixture heated at reflux for 2.5 hours. The hot reaction mixture was filtered, the filter cake washed with methanol, and the combined filtrates concentrated in vacuo. The white oily solid obtained was dissolved in pyridine (4 mL) and trifluoroacetic anhydride (1.63 mL, 11.6 mmol) was added at a rate to maintain a gentle reflux. The mixture was heated at reflux for an additional 30 minutes, cooled to room temperature, diluted with water, and extracted with ethyl acetate (3×). The combined organic phases were washed with 10% KHSO$_4$, water, brine, dried (MgSO$_4$), and concentrated in vacuo to give 2.27 g of yellow oil. Chromatography (Silica Gel 60, 30% ethyl acetate in hexanes) provided 1.28 g (78.0%) of pure title compound as a colorless oil. Crystallization from methanol gave a white solid, mp 36.5°–37° C.

3-Methoxypropionaldehyde oxime (used in Example 29a above)

To a solution of hydroxylamine hydrochloride (2.80 g, 40.2 mmol), 10% aqueous sodium acetate (4.0 mL) and water (6 mL) was added 1,1,3-trimethoxypropane (2.12 mL, 14.9 mmol) and heated at 40°–50° C. for 30 minutes. After cooling to room temperature, the solution was saturated with sodium chloride and extracted with ether (3×) and methylene chloride (3×). The combined organic phases were dried (MgSO$_4$), filtered through a pad of Florisil, and concentrated in vacuo to provide 1.6 g of title compound as a colorless oil which was used as is.

Procedure 3—general procedure for the preparation of the compounds of Examples 30a and b, 31a and b, and 32a and b A mixture of the appropriate 4-hydroxybenzonitrile (1 equivalent), dry ethanol (3.7–8.9 mL per mmol of the 4-hydroxybenzonitrile), hydroxylamine hydrochloride (5 equivalents), and finely divided potassium carbonate (5 equivalents) was refluxed with efficient stirring for 18 hours. The hot reaction mixture was filtered and the filter cake washed with ethanol. The combined filtrates were concentrated in vacuo to give the crude amidoximes which were dissolved into pyridine (1–2 mL per mmol of the 4-hydroxybenzonitrile). Trifluoroacetic anhydride (5 equivalents) was added at a rate to maintain a gentle reflux. After heating an additional 0.5–3 hours, the cooled reaction mixture was diluted with ethyl acetate and water (4:1) until homogeneous. The organic phase was extracted with cold 1N KOH (3×). The basic extracts were acidified with concentrated HCl and extracted with ethyl acetate (3×). The combined organic phases were washed with brine, dried ($MgSO_4$), concentrated in vacuo. Chromatography (Silica Gel 60, ethyl acetate in hexanes or Florisil, methylene chloride) provided the pure 4-hydroxyphenyl-5-trifluoromethyl-1,2,4-oxadiazole.

Following Procedure 3 there were prepared the following crude intermediate amidoximes and corresponding 4-hydroxy-5-trifluoromethyl-1,2,4-oxadiazoles:

| Example | Compound |
| --- | --- |
| 30a | 3,5-Dimethyl-4,N-dihydroxybenzenecarboximidamide - from 3,5-dimethyl-4-hydroxybenzonitrile. |
| 30b | 3-(3,5-Dimethyl-4-hydroxyphenyl)-5-trifluoromethyl-1,2,4-oxadiazole, mp 114–115° C. (hexane) (white needles) - from the product of Example 30a; yield 75.2%. |
| 31a | 3,5-Dichloro-4,N-dihydroxybenzenecarboximidamide - from 3,5-dichloro-4-hydroxybenzonitrile. |
| 31b | 3-(3,5-Dichloro-4-hydroxyphenyl)-5-trifluoromethyl-1,2,4-oxadiazole, mp 96–98° C. (hexane) (white needles) - from the product of Example 31a; yield 52.0%. |
| 32a | 4,N-Dihydroxybenzenecarboximidamide - from 4-hydroxybenzonitrile. |
| 32b | 3-(4-Hydroxyphenyl)-5-trifluoromethyl-1,2,4-oxadiazole, mp 74–75° C. (hexanes) (white needles) - from the product of Example 32a; yield 56.4%. |

EXAMPLE 30c

5-{5-[2,6-Dimethyl-4-(5-trifluoromethyl-1,2,4-oxadiazol-3-yl)-phenoxy]pentyl}-3-methylisoxazole [I; $R_1=CH_3$, $Y=(CH_2)_5$, $R_2$ and $R_3=2,6-(CH_3)_2$, $R_4=CF_3$, $R_5$=hydrogen].

Following a procedure similar to that of Example 1c but substituting the product from Example 30b (1.0 g, 3.9 mmol) for 3,5-dimethyl-4-hydroxybenzonitrile and 5-(3-methylisoxazol-5-yl)pentyl bromide (1.0 g, 4.3 mmol) for 3-(3-methylisoxazol-5-yl)propyl chloride and using 0.72 g (4.3 mmol) of potassium iodide there was obtained 0.25 g (16%) of pure title compound as a white solid, mp 41°–42° C. (methanol).

EXAMPLE 31c

5-{5-[2,6-Dichloro-4-(5-trifluoromethyl-1,2,4-oxadiazol-3-yl)-phenoxy]pentyl}-3-methylisoxazole [I; $R_1=CH_3$, $Y=(CH_2)_5$, $R_2$ and $R_3=2,6-(Cl)_2$, $R_4=CF_3$, $R_5$=hydrogen].

Following a procedure similar to that of Example 1c but substituting the product from Example 31b (0.93 g, 3.1 mmol) for 3,5-dimethyl-4-hydroxybenzonitrile and 5-(3-methylisoxazol-5-yl)pentyl bromide (1.0 g, 4.3 mmol) for 3-(3-methylisoxazol-5-yl)propyl chloride and using 0.72 g (4.3 mmol) of potassium iodide there was obtained 0.83 g (60%) of pure title compound as a white solid, mp 42°–43° C. (hexanes).

EXAMPLE 32c

3-Methyl-5-{3-[4-(5-trifluoromethyl-1,2,4-oxadiazol-3-yl)-phenoxy]propyl}isoxazole [I; $R_1=CH_3$, $Y=(CH_2)_3$, $R_2=R_3$ =H, $R_4=CF_3$, $R_5$=hydrogen].

Following a procedure similar to that of Example 1c but substituting the product of Example 32b (0.42 g, 1.8 mmol) for 3,5-dimethyl-4-hydroxybenzonitrile and using 0.63 g (4.0 mmol) of the product of Example 1b and 0.67 g (4.0 mmol) of potassium iodide there was obtained, after trituration in cold methanol, 0.48 g (76%) of pure title compound as a white powder, mp 68°–69° C. (methylene chloride-hexanes).

EXAMPLE 33

5-{3-[2,6-Dimethyl-4-(5-trifluoromethyl-1,2,4-oxadiazo-3-yl)-phenoxy]propyl}-3-(2-hydroxyethyl)isoxazole [I; $R_1=CH_2CH_2OH$, $Y=(CH_2)_3$, $R_2$ and $R_3=2,6-(CH_3)_2$, $R_4=CF_3$, $R_5$=hydrogen].

A solution of the product of Example 29b (1.28 g, 3.00 mmol), dry 1,2-dichloroethane (9 ml), and trimethylsilyl iodide (1.71 mL, 12.0 mmol) was refluxed for 4 hours. To the cooled reaction mixture was added methanol (8 mL). The mixture was diluted with water and extracted with ethyl acetate (3×). The combined organic phases were washed with 10% $NaHSO_3$, saturated $NaHCO_3$, brine, dried ($MgSO_4$), and concentrated in vacuo. Chromatography (Silica Gel 60, 50% ethyl acetate in hexanes) provided 1.11 g (90.2%) of pure title compound as a colorless oil which solidified upon standing, mp 74.5°–75° C. (methanol)(white solid).

EXAMPLE 34 a) 3-(tert-butyldimethylsilyloxymethyl)-5-methylisoxazole.

To a chilled (5° C.) solution of 3-hydroxymethyl-5-methylisoxazole (16.8 g, 148 mmol) and tert-butyldimethylsilyl chloride (24.6 g, 163 mmol) in dry methylene chloride (100 mL) was added over 15 minutes a solution of triethylamine (22.7 mL, 163 mmol) in methylene chloride (25 mL). 4-Dimethylaminopyridine (1.81 g, 14.8 mmol) was added and the thick reaction mixture was stirred at room temperature for 48 hours. Water (100 mL) was added and the aqueous layer extracted with methylene chloride (3×). The combined organic phases were washed with brine, dried ($MgSO_4$), filtered through a pad composed of a layer of Florisil and a layer of Silica Gel 60, and concentrated in vacuo. The yellow oil obtained (36.6 g) was purified by chromatography (Silica Gel 60, 2% ethyl acetate in hexanes) to give 27.7 g (81.9%) of pure title compound as a pale yellow oil.

b) 3-[3-(tert-Butyldimethylsilyloxymethyl)isoxazol-5-yl] propyl alcohol.

To a cold (−78° C.) solution of the product from part (a) (13.0 g, 57.0 mmol) and N,N,N',N'-tetramethylethylenediamine (1.2 mL, 7.9 mmol) in dry tetrahydrofuran (THF) (150 mL) was added over 5 minutes n-butyllithium (31.3 mL, 2.0M in hexane). The bright orange-yellow anion solution was stirred for 25 minutes. Ethylene oxide (50.0 mL of 7.6M solution in dry THF) was added over 10 minutes. After 1.5 hours, saturated $NH_4Cl$ (30 mL) was added. The mixture was allowed to warm to room temperature and diluted with water. The aqueous layer was extracted with ethyl acetate (3×). The combined organic phases were washed with brine, dried ($MgSO_4$), filtered through a pad of Silica Gel 60, and concentrated in vacuo.

Chromatography (Silica Gel 60, 20% ethyl acetate in hexanes) gave 3.44 g of recovered product from part (a) and 8.18 g (52.7%) of pure title compound as a colorless oil.

c) 3-(tert-Butyldimethylsilyloxymethyl)-5-{3-[2,6-dimethyl-4-(5-trifluoromethyl-1,2,4-oxadiazol-3-yl) phenoxy]propyl}-isoxazole.

A solution of the product from part (b) (1.00 g, 3.67 mmol), the product of Example 30b (1.04 g, 4.04 mmol), and triphenylphosphine (1.06 g, 4.04 mmol) in dry tetrahydrofuran (THF) (10 mL) was chilled to 0° C. A solution of diethyl azodicarboxylate (DEAD) (0.61 mL, 1.04 mmol) in dry THF (15 mL) was added dropwise over 20 minutes. The solution was stirred for 30 minutes at 0° C. and 18 hours at room temperature, diluted with water, and extracted with ethyl acetate (2×). The combined organic phases were washed with 10% NaOH, brine, dried (MgSO$_4$), filtered through a pad of Silica Gel 60, and concentrated in vacuo to give 3.44 g of yellow oil. Chromatography (Silica Gel 60, 10% ethyl acetate in hexanes) provided 1.73 g (83.6%) of pure title compound as a colorless oil.

d) 5-{3-[2,6-Dimethyl-4-(5-trifluoromethyl-1,2,4-oxadiazol-3-yl)phenoxy]propyl}-3-(hydroxymethyl)isoxazole [I; $R_1$=CH$_2$OH, Y=(CH$_2$)$_3$, $R_2$ and $R_3$=2,6-(CH$_3$)$_2$, $R_4$=CF$_3$, $R_5$=hydrogen].

A solution of the product from part (c) (0.75 g, 1.5 mmol), tetrahydrofuran (60 mL), and 1N HCl (7.5 mL) was stirred at room temperature for 18 hours and diluted with water (100 mL). The pH was adjusted to pH 7 (pH paper) with solid NaHCO$_3$ and extracted with ethyl acetate (3×). The combined organic phases were washed with brine, dried (MgSO$_4$), and concentrated in vacuo to give 0.73 g of yellow oil which was purified by chromatography (Silica Gel 60, 50% ethyl acetate in hexanes) to provide 0.58 g (100%) of pure title compound as a white solid, mp 92°–3° C. (white needles from ethanol).

EXAMPLE 35 a) 3,5-Dimethyl-4-{3-[3-(tert-butyldimethylsilyloxymethyl)-isoxazol-5-yl]propyloxy}benzonitrile.

To a chilled (0° C.) methylene chloride (25 mL) solution of 3,5-dimethyl-4-hydroxybenzonitrile (773 mg, 5.26 mmol), the product from Example 34b (1.43 g, 5.26 mmol), and triphenylphosphine (1.38 g, 5.26 mmol) was added dropwise over 30 minutes a solution of diethyl azodicarboxylate (DEAD) (915 mg, 5.26 mmol) in methylene chloride (5 mL). The solution was stirred at 0° C. for 30 minutes and at room temperature for 18 hours, after which it was washed with water, 2.5M NaOH, brine, dried (Na$_2$SO$_4$) and concentrated in vacuo. The residue was triturated in ether to remove the bulk of the triphenylphosphine oxide, the filtrate concentrated in vacuo, and the residue purified by chromatography (Silica Gel 60, 15% ethyl acetate in hexanes) to give 1.73 g (82.2%) of pure title compound as a colorless oil.

b) 3,5-Dimethyl-4-{3-[3-(tert-butyldimethylsilyloxymethyl)-isoxazol-5-yl]propyloxy}-N-hydroxybenzenecarboximidamide.

A mixture of the product from part (a) (1.22 g, 3.05 mmol), ethanol (30 mL), hydroxylamine hydrochloride (1.06 g, 15.2 mmol), and finely divided potassium carbonate (2.10 g, 15.2 mmol) was refluxed for 5 hours and filtered. The filter cake was washed with ethanol and the combined filtrates concentrated in vacuo to give 1.30 g of white solid. A portion of this material (0.78 g) was purified by chromatography (reverse phase silica gel, 17% water in methanol) to give 0.47 g of title compound which contained approximately 5% (NMR analysis) of desilylated material.

c) 5-{3-[4-(5-Cyclopropyl-1,2,4-oxadiazol-3-yl)-2,6-dimethylphenoxy]propyl}-3-(hydroxymethyl)isoxazole [I; $R_1$=CH$_2$OH, Y=(CH$_2$)$_3$, $R_2$ and $R_3$=2,6-(CH$_3$)$_2$, $R_4$=cyclopropyl, $R_5$=hydrogen].

To a solution of the purified product from part (b) (0.47 g, 1.1 mmol) in pyridine (20 mL) was added cyclopropylcarbonyl chloride (0.15 mL, 1.6 mmol). The mixture was heated at 90° C. for 26 hours. The pyridine was removed in vacuo and the residue partitioned between water and ethyl acetate. The aqueous phase was extracted with ethyl acetate (3×). The combined organic phases were washed with 3N HCl (2×), brine, dried (Na$_2$SO$_4$), and concentrated in vacuo to yield 0.61 g of a yellow oil. Chromatography (Silica Gel 60, 35% ethyl acetate in hexanes) provided 0.25 g (62%) of pure title compound as a colorless oil. Cyrstallization from methylene chloride and hexanes provided the title compound as a white solid, mp 80°–1° C.

EXAMPLE 36 a) 5-Cyclopropyl-3-[4-(5-ethoxycarbonyl-4-pentynyloxy)-3,5-dimethylphenyl]-1,2,4-oxadiazole.

To a cold (−78° C.) dry tetrahydrofuran solution (20 mL) of the product from Example 24 (1.30 g, 4.41 mmol) was added dropwise n-butyllithium (2.30 mL, 2.3M in hexane) over 15 minutes. After an additional 30 minutes at −78° C., ethyl chloroformate (0.63 mL, 6.6 mmol) was added and the mixture warmed gradually to 0° C. over 2 hours. The reaction was quenched with saturated NH$_4$Cl and extracted with ethyl acetate (3×). The combined organic phases were washed with brine, dried (Na$_2$SO$_4$), and concentrated in vacuo to give a colorless oil (2.05 g). Chromatography (Silica Gel 60, 10–20% ethyl acetate in hexanes) provided 1.38 g (85.0%) of pure title compound as a colorless oil.

b) 5-{3-[4-(5-Cyclopropyl-1,2,4-oxadiazol-3-yl)-2,6-dimethylphenoxy]propyl}-3-hydroxyisoxazole [I; $R_1$=OH, Y=(CH$_2$)$_3$, $R_2$ and $R_3$=2,6-(CH$_3$)$_2$, $R_4$=cyclopropyl, $R_5$=hydrogen].

A mixture of the product from part (a) (810 mg, 2.20 mmol), ethanol (15 mL), hydroxylamine hydrochloride (400 mg, 5.76 mmol), and 10% NaOH (5 mL) was stirred at room temperature for 24 hours (after 8 hours, a solution was obtained). Water (6 mL) was added, the mixture acidified with concentrated HCl to pH 2 (pH paper), and extracted with ether (4×). The combined organic phases were washed with brine, dried (Na$_2$SO$_4$), and concentrated in vacuo to a white solid. Chromatography (Silica Gel 60, 50% ethyl acetate in hexanes) provided 0.55 g (70%) of pure title compound as a white solid, mp 155°–6° C. (ethyl acetate and hexanes).

EXAMPLE 37

5-{3-[4-(5-Cyclopropyl-1,2,4-oxadiazol-3-yl)-2,6-dimethyl-phenoxy]propyl}-3-ethoxyisoxazole [I; $R_1$=CH$_2$CH$_3$, Y=(CH$_2$)$_3$, $R_2$ and $R_3$=2,6-(CH$_3$)$_2$, $R_4$=cyclopropyl, $R_5$=hydrogen].

A mixture of the product of Example 36b (0.30 g, 0.85 mmol), dry acetone (25 mL), finely divided potassium carbonate (0.24 g, 1.7 mmol), and ethyl iodide (0.18 mL, 2.2 mmol) was heated at 50° C. for 18 hours, filtered, and concentrated in vacuo to give a pinkish solid. Chromatography (Silica Gel, 50% ethyl acetate in hexanes) provided 0.19 g of slightly impure title compound and 0.12 g (37%) of a pure side product (the corresponding 2,3-dihydro-2-ethyl-3-oxoisoxazole compound) as a colorless oil. Pure title compound was obtained by chromatography (reverse silica gel, 20% water in methanol); yield 0.14 g (43%), mp 70°–1° C. (methanol).

EXAMPLE 38

5-{3-[4-(5-Aminocarbonyl-1,2,4-oxadiazol-3-yl)-2,6-dimethyl-phenoxy]propyl}-3-methylisoxazole [I; $R_1=CH_3$, $Y=CH_2)_3$, $R_2$ and $R_3=2,6-(CH_3)_2$, $R_4=CONH_2$, $R_5=$hydrogen].

Finely divided product of Example 7 (3.08 g, 8.00 mmol) was added to 10% ethanolic ammonia (80 mL). After 15 minutes, a solution was obtained and a fine precipitate started to form. After 4 hours, the mixture was filtered and the solids obtained washed with cold ethanol to give 2.35 g (82.5%) of pure title compound as a fine white powder, mp 177°–8° C. (iso-propyl acetate).

EXAMPLE 39

5-{3-[4-(5-Cyano-1,2,4-oxadiazol-3-yl)-2,6-dimethylphenoxy]-propyl}-3-methylisoxazole [I; $R_1=CH_3$, $Y=(CH_2)_3$, $R_2$ and $R_3=2,6-(CH_3)_2$, $R_4=CN$, $R_5=$hydrogen].

To a chilled (0° C.) suspension of the product of Example 38 (1.60 g, 4.50 mmol) and dry pyridine (11.2 mL) in dry tetrahydrofuran (27 mL) was added trifluoroacetic anhydride (1.90 mL, 13.5 mmol). The mixture was stirred at 0° C. for 4 hours and at room temperature for 18 hours, diluted with water (100 mL), and extracted with ethyl acetate (2×25 mL). The combined organic phases were washed with 1N HCl (3×), brine, dried (MgSO_4), and concentrated in vacuo. The red solid obtained (1.67 g) was chromatographed (Silica Gel 60, 20% ethyl acetate in hexanes) to give 1.38 g (90.8%) of pure title compound as a white solid, mp 93°–4° C. (ethyl acetate and hexanes).

EXAMPLE 40

5-{3-[2,6-Dimethyl-4-(5-(hydroxymethyl)-1,3,4-oxadiazol-3-yl)phenoxy]propyl}-3-methylisoxazole [I; $R_1=CH_3$, $Y=(CH_2)_3$, $R_2$ and $R_3=2,6-(CH_3)_2$, $R_4=CH_2OH$, $R_5=$hydrogen].

A mixture of the product of Example 9 (4.12 g, 10.7 mmol) and finely divided potassium carbonate (1.48 g, 10.7 mmol) in dry methanol (40 mL) was stirred at room temperature for 15 minutes and partitioned between water (50 mL) and ethyl acetate (50 mL). The aqueous phase was extracted with ethyl acetate (1×25 mL) and the combined organic phases washed with brine, dried (MgSO_4), and concentrated in vacuo. Chromatography (Silica Gel 60, 50% ethyl acetate in hexanes) provided 3.35 g (91.2%) of pure title compound as a white solid, mp 116.5°–117° C. (ether).

EXAMPLE 41

5-{3-[2,6-Dimethyl-4-(5-(iodomethyl)-1,2,4-oxadiazol-3-yl)-phenoxy]propyl}-3-methylisoxazole [I; $R_1=CH_3$, $Y=(CH_2)_3$, $R_2$ and $R_3=2,6-(CH_3)_2$, $R_4=CH_2I$, $R_5=$hydrogen].

A solution of sodium iodide (0.45 g, 3.0 mmol) in dry acetone (5 mL) was added dropwise to a solution of the product of Example 10 (905 mg, 2.50 mmol) in dry acetone (5 mL). After 4 hours, the yellow suspension was poured into water (50 mL) and extracted with methylene chloride (3×25 mL). The combined organic phases were washed with brine, dried (MgSO_4), and concentrated in vacuo to give a brown oil (1.56 g). Filtration through Florisil (methylene chloride) provided a green-yellow oil (1.43 g) which solidified upon standing at 0° C. Chromatography (Silica Gel 60, 25% ethyl acetate in hexanes) provided 1.06 g (93.8%) of pure title compound as a pale yellow solid, mp 89°–90° C. (white needles from ether-pentane).

EXAMPLE 42

5-{3-[2,6-Dimethyl-4-(5-(4-methylphenylsulfonyloxymethyl)-1,2,4-oxadiazol-3-yl)phenoxy]propyl}-3-methylisoxazole [I; $R_1=CH_3$, $Y=(CH_2)_3R_2$ and $R_3=2,6-(CH_3)_2$, $R_4=4-CH_3C_6H_4SO_2OCH_2$, $R_5=$hydrogen).

To a chilled (0° C.) mixture of the product of Example 40 (343 mg, 1.00 mmol) and finely divided potassium carbonate (0.28 g, 2.0 mmol) in dry methylene chloride (5 mL) was added dropwise a filtered solution of p-toluenesulfonyl chloride (0.23 g, 1.2 mmol) in methylene chloride (2 mL). The mixture was stirred at room temperature for 72 hours, after which an additional 0.40 mmol of potassium carbonate and p-toluenesulfonyl chloride was added. After 24 hours, the mixture was partitioned between water (10 mL) and ethyl acetate (10 mL). The organic phase was washed with 1N NaOH (1×5 mL), brine, dried (MgSO_4), and concentrated in vacuo. Chromatography (Silica Gel 60, 40% ethyl acetate in hexanes) provided 478 mg (96.1%) of pure title compound as a white solid, mp 97°–8° C. (ether).

EXAMPLE 43

5-(3-[2,6-Dimethyl-4-(5-(2,2,2-trifluoroethyl)-1,2,4-oxadiazol-3-yl)phenoxy]propyl}-3-methylisoxazole [I; $R_1=CH_3$, $Y=(CH_2)_3$, $R_2$ and $R_3=2,6-(CH_3)_2$, $R_4=CH_2CF_3$, s $R_5=$hydrogen].

A mixture of the product of Example 1d (4.55 g, 15.0 mmol), dry tetrahydrofuran (45 mL), 2-trifluoro-ethylidene-1,3-dithiane (3.60 g, 18.0 mmol), and silver trifluoroacetate (7.3 g, 33 mmol) was refluxed in the dark for 22 hours, cooled to room temperature, and filtered. The green filter cake was washed with ethyl acetate (4×20 mL). The combined filtrates were concentrated in vacuo. The residue obtained was dissolved in methylene chloride (50 mL) and washed with water (3×25 mL), 0.1M NaHCO_3 (freshly prepared, 25 mL), brine, dried (MgSO_4), filtered through a pad of Florisil, and concentrated in vacuo to give 5.39 g of a yellow paste. Purification by chromatography (Silica Gel 60, 15% ethyl acetate in hexanes) provided 2.22 g (37.5%) of pure title compound as a white solid, mp 84°–85° C. (methanol) (white plates).

EXAMPLE 44

5-{3-[4-(5-Cyclopropyl-1,2,4-oxadiazol-3-yl)-2,6-dimethylphenoxy]propyl}-3-(2-hydroxyethoxy)isoxazole [I; $R_1=HOCH_2CH_2O$, $Y=(CH_2)_3$, $R_2$ and $R_3=2,6-(CH_3)_2$, $R_4=$cyclopropyl, $R_5=$hydrogen).

A mixture of the product of Example 36b (0.75 g, 2.1 mmol), dry acetone (25 mL), finely divided potassium carbonate (0.32 g, 2.3 mmol), and 2-bromoethanol (0.19 mL, 2.7 mmol) was refluxed for 5 hours, filtered, and concentrated in vacuo to give a pinkish oil. Chromatography (Silica Gel 60, 50% ethyl acetate in hexanes) provided 0.51 g of impure title compound and 0.48 g (57%) of a pure side product (the corresponding 2,3-dihydro-2-(2-hydroxyethyl)-3-oxo-isoxazole compound) as a white solid. Pure title compound (0.31 g, 37%) was obtained by gradiant chromatography (Silica Gel 60, hexanes to 50% ethyl acetate in hexanes), mp 64°–65° C. (methylene chloride and hexanes).

Following a procedure similar to that of Example 1c but substituting for 3,5-dimethyl-4-hydroxybenzonitrile an equivalent amount of the following:

4-hydroxy-3-nitrobenzonitrile
4-hydroxy-3,5-dimethoxybenzonitrile
4-hydroxy-3-trifluoromethylbenzonitrile there can be obtained respectively the following compounds of formula IX:

4-[3-(3-methylisoxazol-5-yl)propyloxy]-3-nitrobenzonitrile
3,5-dimethoxy-4-[3-(3-methylisoxazol-5-yl)propyloxy]-benzonitrile 4-[3-(3-methylisoxazol-5-yl)propyloxy]-3-(trifluoromethyl)benzonitrile.

EXAMPLE 45 a) Methyl (3,5-dimethyl-4-hydroxy)benzoate.

A mixture of 9.97 g (60 mmol) of 3,5-dimethyl-4-hydroxybenzoic acid, 20 ml of methanol, 100 ml of dichloroethane, and 2 ml of conc. sulfuric acid was refluxed for 20 h. The reaction mixture was cooled to room temperature, washed with water (2×25 ml), saturated sodium bicarbonate solution (2×25 ml), and brine, and dried over magnesium sulfate. The organic layer was filtered through a short plug of florisil with methylene chloride and the filtrate was concentrated in vacuo to afford 10.2 g (94.4%) of the title ester, m.p. 124°–128° C.

b) N-Hydroxy-cyclopropylcarboximidamide.

Sodium metal 575 mg (25 mmol) was dissolved in 15 ml of dry methanol (dried over 4 A Molecular sieves) and the resulting solution was added dropwise to a suspension of 1.74 g (25 mmol) of hydroxylamine hydrochloride in 5 ml of dry methanol. The mixture was stirred for 1 h and filtered. To the above filtrate was added 1.84 g (25 mmol) of cyclopropylcyanide and the reaction mixture was refluxed overnight. After cooling, the mixture was filtered and the filtrate was concentrated in vacuo yielding 2.32 g of a thick oil. The thick oil was dissolved in 2ml of methanol, filtered, and concentrated in vacuo affording 1.74 g (69.6%) of the title compound as a colorless thick oil.

c) 3-(3-Methylisoxazol-5-yl)propyl alcohol.

3,5-Dimethylisoxazole (220g, 2.27 mol) in 2.2 L of tetrahydrofuran under nitrogen was cooled with stirring to −75° C. and 908 ml of 2.5M n-butyllithium 92.27 mol) in hexane were added over 1 h, keeping the temperature at or less than −65° C. The chilled solution was stirred for thirty minutes after addition was complete and was then treated at about −70° C. with a solution of 112 g (2.54 mol) of ethylene oxide in 390 ml tetrahydrofuran over a period of 1.5 h, keeping the temperature at about −65° C. and stirred overnight. The mixture was quenched at 8° C. by adding 1.2 L of 2.5M hydrochloric acid over a period of 20 min, during which time the temperature rose to 23° C., and was stirred for 10 min. The organic phase was separated, washed with 500 ml of water, and concentrated to give 147 g (46%) of title compound as a brown oil. The combined aqueous phases (original+water wash) were extracted with methyl tert-butyl ether (3×200 ml) and the combined organic extracts were concentrated to give an additional 125 g (39%) of title compound as a brown oil.

d) 3-(3-Methylisoxazol-5yl)propyl chloride.

To the product from part (a) (125 g, 0.885 mol) in 1225 ml methylene chloride was added 192 ml (2.62 mol) of thionyl chloride over a period of 1 h during which time the temperature rose to 40° C. to a gentle reflux. Heating at reflux was continued for 3 h, the reaction mixture was allowed to stand overnight, and then heating at reflux was continued for 1 h. The reaction mixture was added as a steady stream to 3 kg of ice water with vigorous stirring, and stirring was continued for 1 h and the aqueous phase was separated. Water (1 L) was added to the organic phase followed by 161 g of solid sodium bicarbonate in portions with vigorous stirring. The organic phase was separated and concentrated in vacuo to give a black oil which was purified by wiped-film distillation to give 94 g of the title compound as a yellow oil, b.p. 65° C./0.09 mm.

e) Methyl 3,5-dimethyl-4-[3-(3-methylisoxazol 5yl]propyloxy]benzoate.

A mixture of 10.1 g (56 mmol) of methyl 3,5-dimethyl-4-hydroxybenzoate, 100 ml of dry N-methyl-2-pyrrolidinone, 15.5 g (112 mmol) of milled potassium carbonate, 0.93 g (5.6 mmol) of potassium iodide, and 11.2 ml (84 mmol) of the product from part (d) was stirred at 65° C. for 18 h. To the above mixture additional chloride from part (d) (1.9 ml) and milled potassium carbonate (1.9 g) were added and the resulting mixture was stirred at 65° C. for 6 h. The mixture was poured into 200 ml of water and the aqueous layer was extracted with ether (3×50 ml). The combined organic layer was washed with water (2×25ml), brine, dried over magnesium sulfate, and concentrated in vacuo to provide 22.2 g of a crude product. MPLC (Silica Gel 60 50×460 mm, 25% ethyl acetate in hexane, 60 ml/min) provided 16.6 g (92.6%) of pure title compound.

f) 3.5-Dimethyl-4-[3-(3-methylisoxazol5yl)propyloxy]benzoic acid.

A mixture of the product prepared according to part (e) (7.58 g, 25 mmol), 80 ml ethanol/water (1:1), and 1.2 g (30 mmol) of sodium hydroxide was refluxed for 1 h. The mixture was cooled to room temperature, ethanol was removed in vacuo, and the aqueous layer was washed with 20 ml of ether. To the above aqueous layer was added 1.72 ml (30 mmol) of glacial acetic acid, the resulting mixture was chilled and filtered. The residue was washed with water and dried in vacuo (65° C./0.1 mm, 18 h with $P_2O_5$) to provide 6.9 g (95.4%) of the title compound as a white solid, m.p. 160°–162° C.

g) 3.5-Dimethyl-4[3-(3-methylisoxazol5yl)propyloxl benzoyl chloride.

To 2.8 g (10 mmol) of 3,5-dimethyl-4[3-(3-methylisoxazol-3-yl)propyloxy]-benzoic acid (the product prepared according to part (e)) was added 1.72 ml (20 mmol) of oxalyl chloride and the mixture was stirred at room temperature for 1 h and then refluxed for 2 h. The mixture was concentrated in vacuo affording 3.1 g of the title compound as a dark red oil.

h) 1.2895 g. 4-cyano, 2–6-dimethylphenol (8.76 mmols), was taken up in 25 mls. of absolute ethanol to which was added 3.04 g. (43.8 mmol) of hydroxylamine hydrochloride ($H_2NOH.HCl$) followed by potassium carbonate (6.05 g) and stirred for 72 hours. Reaction mixture was filtered, rinsed with ethanol, and concentrated under vacuum giving 1.77 g. of an off white material as the amideimide product.

i) 1.77 g. of the amideimide product from above (8.8 mmol) was taken up in 10 mls. of pyridine. To this mixture was added 3.7 g. (35 mmols) cyclopropyl carbonylchloride via syringe, dropwise. Upon addition a precipitate formed, the reaction mixture was diluted with ether and poured into a separatory funnel. The ether layer was extracted with 1 mmol of HCl, water and aqueous potassium bicarbonate. Dried over sodium sulfate filtered and concentrated in vacuo to give a solid which was crystalized in ether. The m.p. 134° C. to 135° C.

j) Product from above (0.56 g.) was suspended in toluene and heated to reflux for 36 hours until the solution became clear. The reaction mixture was concentrated in vacuo a quantitative yield of 1,2,4-oxadiazole product. 162.5 mg (0.51 mmols) of this product was suspended in sodium methoxide (26.8 mg, 0.05 mmol/methanol) and stirred for room temperature for three days. The product was then diluted with water and neutralized with 1M of HCl and extracted with ether. Ether fractions were combined and were washed with aqueous 1.5M potassium carbonate and k) 5-{3-[2,6-Dimethyl-4-(5-cyclopropyl-1,2,4-oxadiazol-3-yl)phenoxy]propyl}-3-methylisoxazole. [$R_1$=$CH_3$, Y=$(CH_2)_3$, $R_2$ and $R_3$=2,6-dimethyl, $R_4$=cyclo-propyl, $R_5$=hydrogen].

To a solution of the product from part (b) (1.05 g, 10.5 mmol) in 10 ml of dry pyridine heated to 45° C. was added dropwise a solution of the product from part (g) (3.1 g, 10 mmol) in 10 ml of dry THF and the mixture was heated to reflux for 1 h and concentrated in vacuo. The residue was partitioned between 50 ml of ethyl acetate and 25 ml of water, the organic layer was washed with water (2×25 ml), brine, and dried over magnesium sulfate. The organic layer was concentrated in vacuo to provide 3.4 g of a product which was heated at 145° C. in vacuo for 10 min and cooled. MPLC (Silica Gel 60 26×460 mm, 15% ethyl acetate in hexane, 20 ml/min) provided 1.48 g (41.9%) of pure title compound. The product was recrystallized from methanol and dried in vacuo to afford 1.28 g of the title compound.

EXAMPLE 46 a) N-hydroxy-trifluoroacetoximidamide.

Sodium metal (575 mg, 25.0 mg-atom) was dissolved in 15 ml of dry methanol (dried over 4 A Molecular sieves) and the resulting solution was added dropwise to a suspension of 1.74 g (25 mmol) of hydroxylamine hydrochloride in 5 ml of dry methanol. The mixture was stirred at room temperature for 1.5 h and filtered. The above filtrate was cooled to 0° C., 2.7 g (28 mmol) of trifluoroacetonitrile was slowly bubbled in and the resulting mixture was stirred at room temperature for 18 h. The mixture was filtered, concentrated in vacuo, and the residue (thin oil with white solid) was dissolved in chloroform and filtered through super-cel. The filtrate was concentrated in vacuo to provide 2.84 g (89.4%) of the title compound.

b) Methylamidino-3,5-dimethyl-4-[[3-(3-methyl-5-isoxazolyl)propyl]oxy]benzoate.

A solution of 3.08 g (10 mmol) 3,5-dimethyl-4-[[3-(3-methyl-5-isoxazolyl)propyl]oxy]benzoyl chloride (the product prepared according to part (1 g)) in 10 ml of dry THF was added dropwise to a solution of 1.41 g (11 mmol) of the product from part (2a) in 10 ml of dry pyridine (over 4A sieves) and the mixture was stirred at room temperature for 1 h. An additional N-hydroxy-trifluoroacetoximidamide (0.2 g, 2a) was added and the mixture was stirred at room temperature for 1 h. The reaction mixture was concentrated in vacuo, the residue partitioned between 25 ml of water and 25 ml of ethyl acetate, and the aqueous layer was extracted with ethyl acetate (2×15 ml). The combined organic layer was washed with water (3×15 ml), brine, and the organic layer was dried over magnesium sulfate and concentrated in vacuo. The residue (partial solid) was dissolved in 10 ml of ethyl acetate and concentrated (this procedure repeated 2×) to provide 4.31 g of the title compound.

c) A compound of formula I wherein $R_1$=$CH_3$, Y=$(CH_2)_3$, $R_2$ and $R_3$=2,6-dimethyl, $R_4$=trifluoromethyl. The product from part 46b, 4.31g was heated at 145° C. for 1 h and at 155° C. for 4.5 h. A dark solid product, after cooling, was purified by flash chromatography (silica gel 60, 2.8×35 cm) eluting with methylene chloride to afford 1.28 g (33.6%) of the title compound which was recrystallized from methanol. MPLC (Silica Gel 60 26×460 mm, 5% ethyl acetate in methylene chloride, 20 ml/min) provided 931 mg (18.9%) of pure title compound. The product was recrystallized from ethyl acetate and dried in vacuo to afford 527 mg of the title compound, m.p. 175°–176.5° C.

EXAMPLE 47

A compound of formula I wherein $R_1$=$CH_3$, Y=$(CH_2)_3$, $R_2$ and $R_3$=2,6-dimethyl, $R_4$=amino. To a suspension of 30 g of powdered 4A sieves in 180 ml of absolute ethanol was added 4.14 g (180 mg-atom) of sodium metal. After all Na dissolved, 12 g of hydroxyguanidine sulfate hydrate was added and the mixture was stirred for 1 h at room temperature. To the above mixture a solution of 4.55 g (15 mmol) of methyl 3,5-dimethyl-4-[[3-(3-methyl-5-isoxazolyl) propyl]oxy]-benzoate (the product prepared according to (1e)) in 5 ml of absolute ethanol was added and the resulting mixture was refluxed for 2 h, concentrated in vacuo, and the residue was partitioned between 100 ml of water and 50 ml of ethyl acetate. The aqueous layer was extracted with ethyl acetate (2×25ml), the combined organic layer was washed with brine, dried over magnesium sulfate, and concentrated in vacuo to provide 1.65 g of a yellow solid.

EXAMPLE 48 a) A compound of formula I wherein $R_1$=$CH_3$, Y=$(CH_2)_3$, $R_2$ and $R_3$=2,6-dimethyl, $R_4$=2-furyl.

Hydroxy 3,5-dimethyl-4-[[3-(3-methyl-5-isoxazolyl) propyl]oxy]-benzenecarboximidamide (1.52 g, 5 mmol) was dissolved in 30 ml of acetone and 0.83 g (6 mmol) of potassium carbonate was added to the solution. The mixture was stirred and cooled to 0° C., 0.6 ml (6 mmol) of furoyl chloride was added dropwise via syringe over 2 min, and the resulting reaction mixture was stirred 15 min in ice bath and stirring of a solid mixture continued for 2.5 h at room temperature. The resulting mixture was filtered, the residue washed with acetone, and the combined filtrates were concentrated in vacuo to provide 1.939 g of a nearly white solid. The solid product was heated (mp 130° C.) neat in an oil bath under nitrogen, and the liquid product was heated at 150° C. for 20 min and cooled to provide 1.8 g of a brown cake. The solid which dissolved in 35 ml of methylene chloride was purified by passing through a wet-packed silica gel column (196 g; 40×330 mm) with methylene chloride/ ethyl acetate (96:4) to provide 1.278 g (67%) of the title compound, as a white solid, m.p. 123.5°–125° C.

b) A compound of formula I wherein $R_1$=$CH_3$, Y=$(CH_2)_3$, $R_2$ and $R_3$=2,6-dimethyl, $R_4$=2-thienyl. Hydroxy 3,5-dimethyl-4-[[3-(3-methyl-5-isoxazolyl)propyl]oxy] benzenecarboximidamide (0.5 g, 1.65 mmol) was suspended with stirring in 10 ml of acetone and 0.25 g ( 1.81 mmol) of potassium carbonate. The mixture was stirred and cooled to 0° C., 0.2 ml (1.81 mmol) of 2-thiophenecarbonyl chloride was added dropwise in 30 sec, and the resulting reaction mixture was stirred 20 min in ice bath and the stirring continued for 20 min at 0° C. The reaction mixture was filtered, the filtrate was concentrated in vacuo to provide 804 mg of viscous colorless liquid. The liquid was heated neat in an oil bath under nitrogen at 125° C. for 15 min and cooled to provide 727 mg of a solid cake. The solid was dissolved in 20 ml of methylene chloride/ethyl acetate (95:5) and purified by passing through a wet-packed silica gel 60 (41 g; 22×255 mm) with methylene chloride/ethyl acetate (95:5) to provide 363 mg (56%) of the title compound, as a white solid. The product was recrystallized from ethyl acetate and dried at 60° C. in vacuo to provide 207 mg (32%) of a white solid, m.p. 115°–116° C.

c) A compound of formula I wherein $R_1$=$CH_3$, Y=$(CH_2)_3$, $R_2$ and $R_3$=2,6-dimethyl, $R_4$=1-acetoxyethyl.

Hydroxy 3,5-dimethyl-4-[[3-(3-methyl-5-isoxazolyl) propyl]oxy]benzenecarboximidamide (4.45 g, 15 mmol) was suspended at 0° C. with stirring in 45 ml of dry acetone and 2.28 g (16.5 mmol) of potassium carbonate. The mixture was stirred and cooled to 0° C., a solution of 2.48 g (16.5 mmol) of 2-acetoxypropionyl chloride in 8 ml of dry acetone was added dropwise, and the resulting reaction mixture was stirred 15 min at 0° C. The mixture was poured into 100 ml of water and the aqueous layer was extracted with methylene chloride (3×25 ml). The combined organic layer was washed with brine, dried over magnesium sulfate, and concentrated in vacuo to provide 8.05 g of a light yellow solid which was heated neat at 120° C. for 15 min and cooled. The product was dissolved in methylene chloride, dried over magnesium sulfate, filtered through Florisil with methylene chloride, and concentrated in vacuo to provide 7.52 g of a yellow oil. Repeated MPLC (Silica Gel 60 50×460 mm, 3% ethyl acetate in hexane) provided 1.06 g of pure title compound, m.p. 77°–77.5° C.

d) A compound of formula I wherein $R_1=CH_3$, $Y=(CH_2)_3$, $R_2$ and $R_3=2,6$-dimethyl, $R_4=1$-hydroxyethyl. 3.6 g, 9 mmol of the product prepared in 48c was dissolved in 36 ml of dry methanol. To the above solution was added 1.24 g (9 mmol) of milled potassium carbonate and the mixture was stirred at room temperature for 0.5 h. The mixture was partitioned between 25 ml of water and 50 ml of methylene chloride. The aqueous layer was extracted with methylene chloride (2×25 ml), the combined organic layers washed with brine, dried over magnesium sulfate, and concentrated to provide 3.65 g of a pale yellow oil. MPLC (Silica Gel 60 26×460 mm, 40% ethyl acetate in hexane) provided 3.15 g (97.8%) of pure title compound as a white solid which was recrystallized from ethyl acetate, m.p. 83°–87° C.

EXAMPLE 49 a) 1.0 g. (1.5 mmol) of 4-bromo-6-chloro-o-cresol, 0.6 g. (6.7 mmol) of CuCN was combined in 5 mls DMF and heated to reflux, forming an amber solution. Solution was refluxed for 5 hours and was cooled and poured into a separatory funnel with aqueous 2N HCl and ethyl acetate and was extracted three times with ethyl acetate. Combined organic layers were dried over magnesium sulfate, filtered, and concentrated in vacuo to a brown oil. The brown oil was taken up in a minimal amount of methylene chloride and put through a column of silica gel and eluted with 10% ethyl acetate/hexane. Appropriate fractions were concentrated in vacuo to give (210 mg) 28% of a white solid m.p.101° C.

b) 100 mgs. of the compound of Example 49 and 143 mgs. of 3-methyl-5-(3-chloropropyl)-isoxazole, 207 mg. of $K_2CO_3$, 100 mgs. of KI was combined in 2 mls of NMP and heated to 60° C. for 72 hours. The reaction mixture was cooled, and water and ethyl acetate were added, the layers were separated and extracted three times with ethyl acetate. Combined organic layers were dried over magnesium sulfate, filtered and concentrated in vacuo to a yellow oil. The oil was taken up in a minimal amount of methylene chloride and applied to a silica column which was eluted with 10% ethyl acetate/hexane and the appropriate fractions were concentrated in vacuo giving 126 mg (72%) of a white solid m.p. 41.0 ° C. to 42.0° C.

c) 4.20 g. (14 mmol) of the compound of Example 49b 13.80 g. (26 mmol) of hydroxylamine HCl, 9.66 g. (70 mmol) of potassium carbonate $K_2CO_3$ were combined in 100 ml of ethanol and heated to reflux for 9 hours and then cooled. Reaction mixture was hot filtered with ethanol and concentrated in vacuo to a solid. The solid was taken up in a minimal amount of methylene chloride, filtered and then concentrated in vacuo to a white solid which was triturated in ether, filtered and dried to a solid under high vacuum giving 4.06 g. (90%) of the amidoxime.

d) 5-{3-[2,-Methyl-6-chloro-4-(5-difluoromethyl-1,2,4-oxadiazol-3-yl)phenoxy]-propyl}-3-methylisoxazole.

[$R_1=CH_3$, $Y=(CH_2)_3$, $R_2=CH_3$, $R_3=Cl$, $R_4$=difluoromethyl, $R_5$=hydrogen].

A mixture of 3-methyl-5-chloro-4-[3-(3-methylisoxazol-5-yl)propyloxy]-N-hydroxybenzenecarboximidamide (400 mg, 1.2 mmol) and 2 ml of ethyl difluoroacetate was heated at 100° C. under nitrogen for 7 h and cooled. The mixture was concentrated in vacuo, the white solid residue was dissolved in methylene chloride and purified by silica gel chromatography eluting with 10% ethyl acetate/hexane to provide a white solid which was recrystallized from ether/hexane, yielding 142 mg (31%) of the title compound, m.p. 75°–76° C.

e) 5-{3-[2,6-Dimethyl-4-(5-difluorobromomethyl-1,2,4-oxadiazol-3-yl)phenoxy]-propyl}-3-methylisoxazole.

[$R_1=CH_3$, $Y=(CH_2)_3$, $R_2$ and $R_3=2,6$-dimethyl, $R_4$=difluorobromomethyl, $R_5$=hydrogen].

A mixture of 3,5-dimethyl-4-[3-(3-methylisoxazol-5yl)propyloxy]-N-hydroxybenzenecarboximidamide (758 mg, 2.5 mmol) and 0.96 ml (7.5 mmol) of ethyl difluorobromoacetate was heated at 105° C. for 18 h and cooled. The mixture was partitioned between 20 ml of ethyl acetate and 10 ml of water, the organic layer was washed with 1 N HCl, brine, dried over magnesium sulfate, and concentrated to provide 1.12 g of a red oil. The red oil was filtered through Florisil with methylene chloride to yield 400 mg of the product. MPLC (Silica Gel 60 26×460 mm, 15% ethyl acetate in hexane, 20 ml/min) and recrystallization from methanol and drying provided 292 mg of pure title compound as a white solid, m.p. 76°–77° C.

f) Ethyl 2,2-difluoropropionate

Diethylaminosulfur trifluoride (3.63 ml, 27.5 mmol) was added dropwise to 2.9 g (25 mmol) of freshly distilled ethyl pyruvate at 0° C., and the mixture was slowly warmed to room temperature and stirred overnight. The reaction mixture was chilled in an ice bath, 2.5 ml of water was added dropwise, and stirred for 15 min. The mixture was partitioned between 25 ml of water and 15 ml of ether, the organic layer was washed with water, brine, and dried over magnesium sulfate. The organic solution was concentrated in vacuo to provide 2.1 g (60.9%) of the title compound as a yellow oil.

g) 5-{3-[2,6-Dimethyl-4-(5-difluoromethyl-1,2,4-oxadiazol-3-yl)phenoxy]-propyl}-3-methylisoxazole.

[$R_1=CH_3$, $Y=(CH_2)_3$, $R_2$ and $R_3=2,6$-dimethyl, $R_4$=difluoromethyl, $R_5$=hydrogen].

A mixture of 3,5-dimethyl-4-[3-(3-methylisoxazol-5yl)propyloxy]-N-hydroxybenzenecarboximidamide (1.52 g, 5 mmol) and 2.07 ml (15 mmol) of ethyl difluoropropionate, and 0.5 ml of dry N-methylpyrrolidinone was heated at 105° C. for 22 h and cooled. The mixture was diluted with 25 ml of water, extracted with ethyl acetate (2×25 ml), and the organic layer was washed with water (2×25ml), brine, and dried over magnesium sulfate. The organic layer was concentrated in vacuo to provide 1.62 g of a brown oil. MPLC (Silica Gel 60 26×460 mm, 15% ethyl acetate in hexane, 20 ml/min) and recrystallization from methanol and drying provided 618 mg of pure title compound as a white solid, m.p. 64°–65° C.

EXAMPLE 50 a) 5-(t-Butyldiphenylsilyloxy)-1-pentyne. Imidazole (9.29 g (136 mmol) was dissolved in 50 ml of DMF under nitrogen with stirring. To this solution was added 18.75 g (17.74 mmol) of t-butyldiphenylsilyl chloride and 5.27 g (5.55 mmol) of 4-pentyn-1-ol and the mixture was stirred at room temperature for 2 h. The mixture was carefully diluted with 300 ml of water, extracted with ethyl acetate, and the organic layer was washed with water, brine, and dried over magnesium sulfate. The organic solution was concentrated in vacuo to provide 22.66 g of a yellow oil which was purified by passing through 150 g pad of silica gel eluting with hexane and 3% ethyl acetate in hexane affording 17.56 g (86.8%) of the title compound as a clear oil.

b) 3-(ethoxycarbonyl)-5-[3-(t-butyldiphenylsilyloxy)propyl]isoxa-zole.

Ethyl chlorooximidoacetate (16.96 g, 0.112 mol) was dissolved in 50 ml of DMF with stirring under nitrogen and 12.03 g (37.3 mmol) of 5-(t-butyldiphenylsilyloxy)-1-pentyne in 20 ml of DMF was added over a 15 min period. The mixture was stirred at room temperature for 45 min, heated to between 80°–90° C., and 15.6 ml of triethylamine in 30 ml of DMF was added dropwise over a period of 2.25 h. The heating was continued for an additional hour and the mixture was cooled, diluted with 20 ml of water, and extracted with ethyl acetate(3×). The combined organic layer was washed with water, 10% $KHSO_4$ solution (2×), water, brine, and dried over magnesium sulfate. The organic solution was filtered through a pad of silica and the filtrate concentrated in vacuo to provide 21.97 g of a red-brown oil which was purified by passing through 150g of silica gel column, eluting with 2% ethyl acetate in hexane affording 17.9 g (86.8%) of a pale yellow oil. MPLC (Silica Gel 60 26×460 mm, 10% ethyl acetate in hexane, 20 ml/min) provided 12.5 g (76.6%) of pure title compound as a clear oil.

c) 3-(Hydroxymethyl)-5-[3-(t-butyldiphenylsilyloxy)-propyl]isoxazole.

A solution of 3-(ethoxycarbonyl)-5-[3-(t-butyldiphenylsilyloxy)propyl]isoxazole (4.13 g, 9.44 mmol) in 25 ml of THF was added dropwise to a stirred suspension of 0.72 g (18.87 mmol) of LAH in 20 ml of THF at a rate to cause gentle reflux. The mixture was stirred at room temperature for 5 min. The reaction mixture was chilled (0° C.) and treated dropwise sequencially with water (0.72 ml), 0.72 ml of 15% NaOH solution, and then 2.6 ml of water. The mixture was stirred until it became milky and white, and potasium carbonate and magnesium sulfate were added. The mixture was filtered, the filtrate was concentrated in vacuo to provide 3.57 g of a pale yellow oil. This oil was chromatographed twice by passing through (silica gel, 50% ethyl acetate in hexane to provide 3.11 g (83.4%) of the title compound as a clear colorless oil.

d) 3-(Ethylthiomethyl)-5-[3-t-butyldiphenylsilyloxy)-propyl]isoxazole.

A mixture of 3-(hydroxymethyl)-5-[3-(t-butyldiphenylsilyloxy)propyl]isoxazole (5.5 g, 13.9 mmol) and triethylphosphine (8.21 g, 69.5 mmol) in 55 ml of THF was stirred under nitrogen and ethyl disulfide (8.48 g ) was slowly added and the resulting mixture was stirred at room temperature for 0.5 h, refluxed for 1 h, and stirred at room temperature overnight. The mixture was concentrated in vacuo, the residue was diluted with water, and extracted with ethyl acetate. The combined organic layers were washed with water, brine, and dried over magnesium sulfate. The organic solution was concentrated in vacuo to provide 11.11 g of a yellow oil which was purified by two silica gel chromatography separations eluting with 5–20% ethyl acetate in hexane to afford 3.14 g of the title compound as a clear oil.

e) 3-(Ethylthiomethyl)-5-[3-(hydroxy)propyl]isoxazole.

A mixture of 3-(ethylthiomethyl)-5-[3-(t-butyldiphenylsilyloxy)propyl]isoxazole (6.55 g, 14.9 mmol) and 29.81 ml (29.81 mmol) of 1M TBAF in hexane and 300 ml of THF was allowed to stir under nitrogen overnight. An additional 1 eq TBAF (14.9 ml) was added to the mixture and stirring at room temperature was continued for 2 h. The reaction mixture was concentrated in vacuo, the residue was diluted with water and extracted with ethyl acetate. The organic layer was washed with brine, dried over magnesium sulfate, concentrated in vacuo to provide a pale yellow oil which was purified by silica gel (6.6×11 cm) chromatography eluting with 75% ethyl acetate in hexane to provide 2.82 g (94%) of the title compound as a clear oil.

f) 5-(3-[2,6-Dimethyl-4-f5-trifluoromethyl-1,2,4-oxadiazol-3-yl)phenoxy]-propyl)-3-(ethylthiomethyl)isoxazole. [$R_1$=$C_2H_5SCH_2$, Y=$(CH_2)_3$, $R_2$ and $R_3$=2,6-dimethyl, $R_4$=trifluoromethyl, $R_5$=hydrogen]. 3-(Ethylthiomethyl)-5-[3-(hydroxy)propyl]isoxazole (1.14 g, 5.66 mmol), 1.61 g (6.23 mmol) of 2,6-dimethyl-4-(5-trifluoromethyl-1,2,4-oxadiazol-3-yl)phenol, and 1.63 g of triphenylphosphine were combined in 15 ml of THF under nitrogen with stirring. The mixture was chilled to 0° C. and 0.89 ml of diethyl azodicarboxylate (DEAD) in 5 ml of THF was added dropwise over a 10 min period. The resulting orange-red reaction mixture was allowed to warm to room temperature and stirred for 48 h. The mixture was diluted with water, extracted with ethyl acetate, and the organic layer was washed with 5% NaOH solution, water, brine, and dried over magnesium sulfate. The organic solution was passed through a Florisil pad and silica gel (2.4×1.5 cm), concentrated in vacuo to provide 4.92 g of a pale yellow solid. The solid product was passed through silica gel (2.5×12 cm) eluting with 20% ethyl acetate in hexane to provide 2.34 g of an oil. MPLC (120 g Silica Gel 60, 5% ethyl acetate in hexane, 20 ml/min) provided 2.15 g (86%) of pure title compound as a clear oil. Recrystallization from methanol afforded 1.88 g of a white solid, m.p. 36.5°–380° C.

g) 5-{3-[2,6-Dimethyl-4-(5-trifluoromethyl-1,2,4-oxadiazol-3-yl)phenoxy]-propyl}-3-(ethylsulfinomethyl)isoxazole. [$R_1$=$C_2H_5S(O)CH_2$, Y=$(CH_2)_3$, $R_2$ and $R_3$=2,6-dimethyl, $R_4$=trifluoromethyl, $R_5$=hydrogen].

5-{3-[2,6-Dimethyl-4-(5-trifluoromethyl-1,2,4-oxadiazol-3-yl)phenoxy]-propyl}-3-(ethylthiomethyl)isoxazole (1.0 g), 1.39 g of $Al_2O_3$, 2.27 g of oxone, and 12 ml of dry methylene chloride were combined under nitrogen at room temperature and stirred for 0.5 h. The mixture was heated to gentle reflux for 5 h and cooled to room temperature. Magnesium sulfate was added to the mixture, the resulting reaction mixture was filtered and the filtrate concentrated in vacuo. The residue was treated with cold methanol (−78° C.) to provide 650 mg of the title compound as a white solid.

h) 5-{3-[2,6-Dimethyl-4-(5-trifluoromethyl-1,2,4-oxadiazol-3-yl)phenoxy]-propyl}-3-(ethylsulfonylmethyl)isoxazole. [$R_1$=$C_2H_5S(O_2)CH_2$, Y=$(CH_2)_3$, $R_2$ and $R_3$=2,6-dimethyl, $R_4$=trifluoromethyl, $R_5$=hydrogen].

5-{3-[2,6-Dimethyl-4-(5-trifluoromethyl-1,2,4-oxadiazol-3-yl)phenoxy]-propyl}-3-(ethylthiomethyl)isoxazole (0.88 g, 1.99 mmol), 1.99 g of $Al_2O_3$, 3.68 g of oxone, and chloroform were combined under nitrogen at room temperature and stirred for 3 h. The mixture was heated to gentle reflux for 20 h, cooled to room temperature, and dried over magnesium sulfate. The mixture was filtered and the filtrate concentrated in vacuo to provide 1.09 g of a pale yellow solid. The solid was passed through silica gel column (2.0×11 cm) eluting with 50% ethyl acetate in hexane to provide 870 mg (92.6%) of the title compound. The product was crystallized by dissolving in a minimum volume of methylene chloride and then diluting with ether/hexane; m.p. 94°–95° C.

EXAMPLE 51 a) 38.56 g. (0.555 mol.) of $NH_2OH \cdot HCl$ and 76.69 g. of $K_2CO_3$ in 400 ml. of ethanol with vigorous stirring and was combined with 16.33 g. (0.111 mol.) of 2-6-dimethyl-4-cyan6phenol. The mixture was heated to reflux for 43 hours and cooled in an ice bath. Precipitate formed and was filtered off, precipitate was then washed with methanol (300 ml.), filtrate was concentrated in vacuo giving 30.67 g. of a tan solid which was used unpurified in the next step. 0.111 mol. of the amidoxime from Part A was dissolved in 60 mls. of pyridine, 78.36 mls. (0.555 mol.) of trifluoroacedicanhydride was added dropwise over one hour. Reaction mixture was diluted with approximately 1 liter of ice cold water and tan solids filtered off via suction filtration. The filtrate was dried with $MgSO_4$, filtered through silica gel and concentrated in vacuo yielding 18.84 rams of a brown oil. This brown oil was placed on a silica gel column and diluted with 20% EtOAc/hexane and the appropriate fractions were combined, dried over $MgSO_4$ filtered and concentrated in vacuo yielding 7.34 g. of the desired oxadiazolylphenol.

b) 5-{3-[2,6-Dimethyl-4-(5-trifluoromethyl-1,2,4-oxadiazol-3-yl)phenoxy]-propyl}-3-(methylthiomethyl) isoxazole. [$R_1=CH_3SCH_2$, $Y=(CH_2)_3$, $R_2$ and $R_3=2,6$-dimethyl, $R_4=$trifluoromethyl, $R_5=$hydrogen]. This compound was prepared by a procedure similar to that of Example 6f employing 3-(methylthiomethyl)-5-[3-(hydroxy)-propyl]isoxazole, 2,6-dimethyl-4-(5-trifluoromethyl-1,2,4-oxadiazol-3-yl)phenol, triphenylphosphine, and DEAD.

c) 5-{3-[2,6-Dimethyl-4-(5-trifluoromethyl-1,2,4-oxadiazol-3-yl)phenoxy]-propyl}-3-(methylsulfinomethyl)isoxazole. [$R_1=CH_3S(O)CH_2$, $Y=(CH_2)_3$, $R_2$ and $R_3=2,6$-dimethyl, $R_4=$trifluoromethyl, $R_5=$hydrogen].

5-{3-[2,6-Dimethyl-4-(5-trifluoromethyl-1,2,4-oxadiazol-3-yl)phenoxy]-propyl}-3-(methylthiomethyl) isoxazole (1.87 g, 4.37 mmol), 4.37 g of $Al_2O_3$, 2.69 g of oxone, and 22 ml of dry methylene chloride were combined under nitrogen at room temperature and the mixture was heated to gentle reflux for 2 h and stirred at room temperature overnight. The resulting reaction mixture was filtered and the filtrate concentrated in vacuo to provide 2.35 g of a white solid. The solid was passed through silica gel column (100 g) eluting with 50% ethyl acetate in hexane followed by 10% methanol in methylene chloride to provide 1.83 g (94.3%) of the title compound (fraction 11) and 400 mg of the corresponding sulfone (fraction 4–6). The product was crystallized by dissolving in hot methanol and then chilling the solvent to –78° C.; m.p. 103°–103.5° C.

d) 5-{3-[2,6-Dimethyl-4-(5-trifluoromethyl-1,2,4-oxadiazol-3-yl)phenoxy]-propyl}-3-(methylsulfonylmethyl)isoxazole. [$R_1=CH_3S(O_2)CH_2$, $Y=(CH_2)_3$, $R_2$ and $R_3=2,6$-dimethyl, $R_4=$trifluoromethyl, $R_5=$hydrogen].

5-{3-[2,6-Dimethyl-4-(5-trifluoromethyl-1,2,4-oxadiazol-3-yl)phenoxy]-propyl}-3-(methylsulfinomethyl) isoxazole (0.65 g, 1.47 mmol), 1.47 g of $Al_2O_3$, 2.7 g of oxone, and 5 ml of chloroform were combined under nitrogen at room temperature. The mixture was heated to gentle reflux for 10 h, and allowed to stand at room temperature for 48 h. The mixture was filtered and the filtrate concentrated in vacuo to provide 680 mg of a white solid. The product was crystallized by dissolving in hot methanol and cooling the solvent, m.p. 122.5°–123° C.

EXAMPLE 52 a) 3-[Bromomethyl)-5-[3-(t-butyldiphenylsilyloxy)-propyl] isoxazole.

To a solution of triphenylphosphine in 10 ml of methylene chloride, chilled to –20° C., was added dropwise 1.52 g of bromine in 5 ml of methylene chloride till the reaction mixture just turned yellow. The mixture was titrated back to the endpoint with a few flakes of triphenylphosphine. To the above solution was added dropwise 3.11 g (7.86 mmol) of 3-(hydroxymethyl)-5-[3-(t-butyldiphenyl-silyloxy)propyl] isoxazole in 5 ml of methylene chloride over a 10 min period and the mixture was stirred for 15 min. The mixture was partitioned between 20 ml of water and 50 ml of ether, and the aqueous layer was extracted twice with ether. The combined organic layer was washed with brine, dried over magnesium sulfate, and filtered. The filtrate was diluted with an equal volume of hexane, passed through a pad of silica gel 60, and silica gel was washed with 50 ml of ether/hexane (1:1). The combined filtrate was concentrated in vacuo to provide 3.38 g (93.9%) of the title compound as a clear colorless oil.

b) 3-(Dimethylaminomethyl]-5-[3-(t-butyldiphenylsilyloxy) -propyl]isoxazole.

To a solution of 3-(bromomethyl)-5-[3-(t-butyldiphenylsilyloxy)propyl]isoxazole (4.69 g, 10.23 mmol) in 10 ml of N-methylpyrrolidinone was added under nitrogen 2.31 g of dimethylamine (40% aqueous solution, 20.46 mmol). The reaction was slightly exothermic. The mixture was diluted with water and extracted with ethyl acetate (3×). The organic layer was washed with water and brine, dried over magnesium sulfate, filtered, and concentrated in vacuo to provide 3.84 g (88.9%) of the title compound as a pale yellow oil.

c) 3-(Dimethylaminomethyl)-5-[3-(hydroxy)propyl] isoxazole.

3-(Dimethylaminomethyl)-5-[3-(t-butyldiphenylsilyloxy) propyl]isoxazole (3.84 g, 9.09 mmol) and 48 ml of THF were combined under nitrogen with stirring and 18.17 g (18.17 mmol) of TBAF (1M in THF) was added in one portion. The reaction mixture (yellow) was stirred at room temperature for 30 min, diluted with water, and extracted with ethyl acetate (3×). The organic layer was washed with water and brine, dried over magnesium sulfate, filtered, and concentrated to provide 3.31 g of a yellow oil. This oil was passed through a silica gel 60 column (2.5×13 cm) eluting with ethyl acetate, followed by 1% isopropylamine in ethyl acetate to afford 520 mg (31.1%) of the title compound.

d) 5-{3-[2,6-Dimethyl-4-(5-trifluoromethyl-1,2,4-oxadiazol-3-yl)phenoxy]-propyl}-3-(dimethylaminomethyl)isoxazole. [$R_1=$dimethylaminomethyl, $Y=(CH_2)_3$, $R_2$ and $R_3=2,6$-dimethyl, $R_4=$trifluoromethyl, $R_5=$hydrogen].

Diethyl azodicarboxylate (DEAD, 230 mg) in 5 ml of THF was added dropwise over a 5 min period to a chilled (0° C.) and stirring solution of 3-(dimethylamino-methyl)-5-[3-(hydroxy)propyl]isoxazole (230 mg, 1.23 mmol), 350 mg (6.23 mmol) of 2,6-dimethyl-4-(5-trifluoromethyl-1,2,4-oxadiazol-3-yl)phenol, and 350 mg of triphenylphosphine in 7 ml of THF. The mixture was stirred at 0° C. for 15 min and then at room temperature for 30 min. An additional triphenylphosphine (70 mg, 0.25 ml) and DEAD (40 mg) were added to the mixture and stirred at room temperature overnight. The mixture was diluted with water, extracted with ethyl acetate (3×), and the organic layer was washed with water, brine, and dried over magnesium sulfate. The organic solution was concentrated in vacuo, the residue (1.01 g, a pale green oil) was passed twice through a silica gel 60 column (1.5×15 cm), eluting with ethyl acetate, followed by 5% methanol in ethyl acetate to provide 560 mg of a yellow oil. MPLC (120 g Silica Gel 60, 3% methanol in ethyl acetate, 20 ml/min) provided 440 mg of pure title compound as a yellow oil. The oil was repurified by MPLC (120 g Silica Gel 60, 5% ethyl acetate in hexane, 20 ml/min), and the product in 0.5 ml of methylene chloride was filtered through a cotton plug, concentrated in vacuo (35° C./32 mm/4 h) to provide 284 mg of the title compound.

EXAMPLE 53 a) 5-Acetoxyl-1-pentyne.

Acetic anhydride (11.26 g, 110 mmol) was added dropwise with stirring at room temperature to a mixture of 4-pentyne-1-ol (8.24 mmol) and 8.26 g of pyridine (104 mmol), the reaction mixture was allowed to stand at room temperature for 18 h and then heated at 50°–60° C. for 15 min. The mixture was poured into water, extracted with chloroform, and the organic layer was washed with 1M HCl solution and 1.5M KHCO$_3$ solution, and the organic layer was dried over sodium sulfate. The chloroform solution was concentrated in vacuo to provide 13.9 g of the title compound.

b) 3-(ethoxycarbonyl)-5-[(3-acetoxylpropyl]isoxazole.

5-Acetoxy-1-pentyne (13.9 g, 100 mmol) , ethyl nitroacetate (11.8 g, 85.6 mmol) , and 0.5 ml of triethylamine were combined in 100 ml of toluene, and 20,4 g (171.2 mmol) of phenylisocyanate was added at room temperature over a 15 min period. The mixture was stirred at room temperature for 1 h, heated near reflux (105° C.) for 3.5 h, and cooled. The mixture was diluted with ether, washed with 1M HCl solution and 1.5M KHCO$_3$ solution, and the organic layer was dried over sodium sulfate. The organic solution was concentrated in vacuo to provide an amber oil (approx. 30 g) which was purified by silica gel column chromatography (2.5×10, 5–20% ethyl acetate in hexane) followed by Kugelrohr distillation ( 2×: 0.1 mm/heat gun) to provide 5.41 g of the title compound.

c) 3-(Hydroxymethyl)-5-[(3-acetoxy)propyl]isoxazole.

A solution of 3-(ethoxycarbonyl)-5-[(3-acetoxy)propyl] isoxazole (9b, 5.1965 g, 21.5 mmol) in 25 ml of absolute ethanol, chilled in an ice bath, was added 1.03 g (27.2 mmol) of sodium borohydride portionwise (gas evolution). The reaction mixture was quenched by pouring into ice/ methylene chloride, washed with 1M HCl solution (3×) and water, and dried over sodium sulfate. The mixture was filtered and the filtrate was concentrated in vacuo to provide 1.82 g of a yellow oil.

d) 3-(Mesyloxymethyl)-5-[(3-acetoxy)propyl]isoxazole.

Triethylamine (1.85 g, 18.28 mmol), 3-(hydroxymethyl) -5-[(3-acetoxy)propyl]-isoxazole (9c; 1.82 g, 9.14 mmol) were combined and chilled in a dry ice/iso-propanol. To this solution was added 1.57 g (13.7 mmol) of mesyl chloride in 10 ml of methylene chloride over a 30 min period, and the mixture was allowed to warm to room temperature overnight. The mixture was poured into water, the aqueous layer was extracted with methylene chloride (2×), and the combined organic layer was washed with 1.5M KHCO$_3$ solution and dried over sodium sulfate. The solvent was concentrated in vacuo to provide 2.33 g (92%) of the title compound.

e) 3-(Cyanomethyl)-5-[(3-acetoxy)propyl]isoxazole,

To a solution of 3-(mesyloxymethyl)-5-[(3-acetoxy) propyl]isoxazole (9d; 2.33 g, 8.4 mmol) in 50 ml of N-methylpyrrolidinone was added 2.05 g (42 mmol) of sodium cyanide and the mixture was stirred at room temperature overnight. The mixture was poured into water, extracted with ether, and the organic layer was concentrated in vacuo to provide 1. 52 g of the title compound which was purified by passing through a pad of silica gel (1×1.5) eluting with 10% ether/hexane followed by ether.

f) 3-(Cyanomethyl)-5-[(3-hydroxy)propyl]isoxazole.

To a solution of 3-(cyanomethyl)-5-[(3-acetoxy)propyl] isoxazole (9e; 810 mg) in 50 ml of methanol was added 24 mg of sodium methoxide and the mixture was stirred at room temperature overnight. The mixture was poured into ice/ water, extracted with methylene chloride, the organic layer was concentrated in vacuo to provide an amber oil. The oil was passed through a plug of silica gel eluting with ether to provide 10.2 mg of of the title compound, m.p. 51°–52° C.

g) [2,6-Dimethyl-1-(cyclopropylcarboxy)-4-[(5-cyclopropyl)-1,2,4-oxadiazol-3-yl]benzene.

To a solution of N-hydroxy-3,5-dimethyl-4-hydroxyphenylcarboximidamide (1.77 g, 8.8 mmol) in pyridine was added dropwise via syringe 3.7 g (35 mmol) of cyclopropylcarboxylic acid chloride and the mixture was allowed to stand overnight. The reaction mixture was diluted with ether, poured into ice/water, and the organic layer was filtered and washed with 1M HCl solution, water, and KHCO$_3$ solution. The organic solution was dried over sodium sulfate, concentrated in vacuo to provide a semisolid which was triturated in ether and filtered to remove insoluble solids. The filtrate was concentrated to provide 2.36 g of an oil which was dried at 40° C./0.1mm; m.p. 178°–184° C. The above amidine was suspended in toluene, the mixture was refluxed for 23 h, and the solvent was concentrated in vacuo to yield a solid which was recrystallized from methanol to provide 270.8 mg (54%) of the title compound, m.p. 89°–90° C.

h) [2,6-Dimethyl4- [(5-cyclopropyl) -1,2,4-oxadiazol-3-yl] phenol

To a solution of the product of 53(g) above (258 mg, 0.81 mmol) in 10 ml of methanol was added 52 mg of NaOH and the reaction mixture was stirred at room temperature overnight. The mixture was concentrated in vacuo, the residue was diluted with water/methylene chloride, the mixture was treated with aqueous ammonium chloride solution. The organic layer was filtered through a pad of silica gel eluting with methylene chloride to provide the title compound as a white solid, m.p. 94.5°–95.5° C.

i) 5-{3-[2,6-Dimethyl-4-(5-cyclopropyl-1,2,4-oxadiazol-3-yl)phenoxy]propyyl-3-(cyanomethyl)isoxazole.

[R$_1$=cyanomethyl, Y=(CH$_2$)$_3$, R$_2$ and R$_3$=2,6-dimethyl, R$_4$=cyclopropyl, R$_5$=hydrogen].

[2,6-Dimethyl-4-[(5-cyclopropyl)-1,2,4-oxadiazol-3-yl] phenol (172.3 mg, 0.748 mmol), 3-(cyanomethyl)-5-[(3-hydroxy)propyl]isoxazole (112.9 mg, 0.679 mmol), and 197.5 mg (0.735 mmol) of triphenylphosphine were combined under argon in 2 ml of THF. To the above mixture, chilled in ice/water bath, was added DEAD (128 mg, 0.735 mmol) in 2 ml of THF and the mixture was stirred for 24 h. The mixture was poured into water, extracted with ether (3×), and the organic layer was dried over magnesium sulfate and filtered. The organic solution was concentrated in vacuo and the residue was passed through a silica pad (1×1.75) eluting with 20–60% ether/hexane followed by ether to provide 120 mg of the title compound. The product was recrystallized from methanol; m.p. 78°–78.5° C.

j) According to the method of Example 53; using appropriate starting materials, 5-{3-[2,6-Dimethyl-4-(5-trifluoromethyl-1,2,4-oxadiazol-3-yl)phenoxy]-propyl}-3-(cyanomethyl)isoxazole, ($R_1$=cyanomethyl, $R_2$, $R_3$=2,6-dimethyl, $R_4$=trifluoromethyl, $R_5$=hydrogen, Y=1,3-propylene), m.p. 85°–85° C. was prepared.

EXAMPLE 54 a) 5-{3-[2,6-Dimethyl-4-(5-difluorochloromethyl-1,2,4-oxadiazol-3-yl)phenoxy]-propyl}-3-methylisoxazole.

[$R_1$=$CH_3$, Y=$(CH_2)_3$, $R_2$ and $R_3$=2,6-dimethyl, $R_4$=difluorochloromethyl, $R_5$=hydrogen].

3,5-Dimethyl-4-[3-(3-methylisoxazol-5yl)propyloxy]-N-hydroxybenzene-carboximidamide (1.14 g, 3.78 mmol) was dissolved in 3.8 ml of pyridine with stirring under nitrogen, and 1.31 ml (7.54 mmol) of ethyl difluorochloroacetic anhydride was added rapidly dropwise at a rate to cause the reaction temperature to reach just below reflux. The mixture was stirred till it is cooled. The mixture was refluxed for 30 min, chilled in ice bath, and was diluted with 50 ml of water. White solid product was collected by filtration, washed with water (3×50 ml), dissolved in ethyl acetate, and the solution was dried over magnesium sulfate. The solvent was passed through a pad of Florisil and concentrated in vacuo to provide 1.46 g of a yellow oil. This oil was purified by silica gel 60 column chromatography (1.5×10 cm, 20% ethyl acetate in hexane to provide 1.41 g (94 %) of a crystalline solid which was recrystallized from methanol to afford 1.29 g of the title compound, m.p. 58.5°–60° C.

b) 4-[3-(3-Methylisoxazol-5yl)propyloxy]phenylcyanide.

3-(3-Methylisoxazol-5yl)propyl chloride (9.58 g, 60 mmol) and 9 g (60 mmol) of sodium iodide were combined in 75 ml of 2-butanone and the mixture was refluxed with stirring for 30 min. To the above mixture 5.96 g (50 mmol) of 4-cyanophenol and 13.8 g (0.1 mol) of potassium carbonate were added, and the resulting mixture was refluxed overnight. The warm mixture was filtered. The residue was washed with acetone, the combined filtrate concentrated in vacuo, and the light oil residue was crystallized from methanol to provide 5.43 g of the title compound, m.p. 60°–61° C.

c) 4-[3-(3-methylisoxazol-5yl)propyloxy]-N-hydroxybenzenecarboximidamide.

4-[3-(3-Methylisoxazol-5yl)propyloxy]phenylcyanide (10b, 2.42 g, 10 mmol), 3.48 g (50 mmol) of hydroxylamine hydrochloride, and 6.9 g of potassium carbonate were combined in 25 ml of ethanol with stirring and the mixture was refluxed under nitrogen overnight. The mixture was filtered, the filtrate concentrated in vacuo, and the solid residue was triturated in water and recrystallized from isopropyl acetate to provide 2.17 g of the title compound, m.p. 124°–126° C.

d) 5-{3-[4-(5-cyclohexyl-1,2,4-oxadiazol-3-yl)phenoxy]-propyl}-3-methylisoxazole.

[$R_1$=$CH_3$, Y=$(CH_2)$ 3, $R_2$ and $R_3$=H, $R_4$=cyclohexyl, $R_5$=hydrogen].

Cyclohexylcarboxylic acid chloride (1.2 ml, 9.3 mmol) was added neat to a stirred solution of 4-[3-(3-methylisoxazol-5yl)propyloxy]-N-hydroxy-benzenecarboximidamide (1.28 g, 4.65 mmol) in 5 ml of pyridine (exothermic reaction) and the mixture was refluxed for 1 h and cooled. The mixture was diluted with water, solid product was washed with water and dissolved in methanol. The methanol solution was passed through a plug of silica gel, eluting with methylene chloride, and the desired title compound (840 mg, 49%) was obtained after recrystallization from methanol: m.p. 100°–101° C.

e) 5-{3-[4-(5-cyclobutyl-1,2,4-oxadiazol-3-yl)phenoxy]-propyl}-3-methylisoxazole.

[$R_1$=$CH_3$, Y=$(CH_2)_3$, $R_2$ and $R_3$=H, $R_4$=cyclobutyl, $R_5$=hydrogen].

Cyclobutylcarboxylic acid chloride (0.92 g, 7.77 mmol) was added neat to a stirred solution of 4-[3-(3-methylisoxazol-5yl)propyloxy]-N-hydroxy-benzenecarboximidamide (1.07 g, 3.89 mmol) in 5 ml of pyridine (exothermic reaction) and the mixture was refluxed for 1 h and cooled. The mixture was diluted with water, extracted with methylene chloride, and the organic layer was washed with dilute HCl solution, dilute NaOH solution and water, and dried over magnesium sulfate. The solution was passed through a plug of silica gel column, eluting with 10% ethyl acetate in methylene chloride, and the desired title compound (840 mg, 64%) was obtained after crystallization from methanol: m.p. 59°–60° C.

EXAMPLE 55 a) 4-Methoxy-3-methylbenzaldoxime.

3-Methyl-p-anisaldehyde (60 g, 0.33 mol), hydroxylamine hydrochloride (46.27 g, 0.666 mol), 50.02 g of pyridine, and 400 ml of absolute ethanol were combined with stirring under nitrogen, and the reaction mixture was refluxed for 2 h and cooled. The mixture was diluted with water, stirred for 1 h, and the pale yellow solid was filtered, washed with water and air dried. The solid product was dissolved in methylene chloride, the solution was dried over magnesium sulfate, and the solvent was concentrated in vacuo to provide 51.6 g (93.8%) of the title compound as a pale yellow solid.

b) 4-Methoxy-3-methylphenylcyanide.

4-Methoxy-3-methylbenzaldoxime (11a; 51.5 g, 0.3118 mol), 59.75 g (0.3685 mole) of 1,1'-carbonyldiimidazole, 250 ml of methylene chloride were combined with stirring under nitrogen, and the mixture was refluxed overnight. The mixture was cooled, washed with 3N HCl, water, and brine, and the organic layer was dried over magnesium sulfate. The methylene chloride solution was filtered through florisil and concentrated in vacuo to provide 44.9 g (97.8%) of the title compound as a pale yellow solid.

c) 4-Hydroxy-3-methylpheny]cyanide.

To a solution of 4-methoxy-3-methylphenylcyanide (11b, 44.8 g, 0.3044 mol) in 150 ml of methylene chloride, chilled to 0° C. with stirring under nitrogen, was added 575 ml (0.575 mol) of boron tribromide (1M in methylene chloride) in a steady stream, and the mixture was stirred at room temperature for 24 h. The reaction mixture was refluxed overnight, additional boron tribromide (44.7 ml) was added at 25° C. and the mixture was stirred at room temperature for 30 min, refluxed for 3 h, and then stirred at room temperature for 48 h. Tlc indicated the presence of the starting nitrile, and therefore, the third addition of boron tribromide (60.88 ml) was made and the mixture was refluxed overnight. The reaction mixture was chilled to 0° C. in an ice bath, 175 ml of methanol was added dropwise, and 600 ml of water was added. The resulting mixture was stirred overnight. The aqueous layer was extracted with methylene chloride (2×), the organic layer was washed with 10% NaOH solution (3×). The basic aqueous layer was acidified to pH=5 with 6N HCl solution (product oiled out), the mixture was extracted with methylene chloride(3×), and the organic layer was washed with brine and dried over magnesium sulfate. The methylene chloride solution was filtered through Florisil and concentrated in vacuo to provide 38.2 g of the title compound as a pale yellow solid, m.p. 95.5°–97° C.

d) 3-Methyl-4-[3-(3-methylisoxazol-5yl)propyloxy]-phenylcyanide.

3-(3-Methylisoxazol-5yl) propyl chloride (2.7 g, 16.9 mmol) and 0.2 g (60 mmol) of potassium iodide, 3.89 g (28.2 mmol) of potassium carbonate (milled, 80%), 2.7 g g (16.9 mmol) of 2-methyl-4-cyanophenol were combined in 15 ml of N-methyl-2-pyrrolidinone with stirring and the mixture was heated to 60° C. overnight. The mixture was diluted with water, extracted with ethyl acetate (3×), and the organic layer was washed with 10% NaOH solution, water, and brine, and dried over magnesium sulfate. The ethyl acetate solution was filtered through Florisil and concentrated in vacuo to provide 3.64 g of a pale yellow solid. The solid was repurified by MPLC (430 g Silica Gel 60, 20% ethyl acetate in hexane, 25 ml/min) to provide 2.88 g (99.3%) of the title compound as a crystalline solid; m.p. 65°–66° C.

e) 3-Methyl-4-[3-(3-methylisoxazol-5yl)propyloxy]-N-hydroxy-benzenecarboximidamide.

3-Methyl-4- [3-(3-methylisoxazol-5yl)propyloxy] phenylcyanide (11d, 2.35 g, 9.3 mmol), 3.19 g of hydroxylamine hydrochloride, and 6.33 g of potassium carbonate were combined in 45 ml of ethanol with stirring under nitrogen, and the mixture was refluxed under nitrogen for 24 h. The mixture was filtered while warm and the filtrate concentrated in vacuo to provide 2.74 g of the title compound as a pale yellow solid.

f) 5-(3-[2-methyl-4-(5-cyclopropyl-1,2,4-oxadiazol-3-yl) phenoxy]-propyl}-3-methylisoxazole [$R_1$=$CH_3$, y=$(CH_2)_3$, $R_2$ and $R_3$=H, $R_4$=cyclopropyl, $R_5$=hydrogen].

3-Methyl-4-[3-(3-methylisoxazol-5yl)propyloxy]-N-hydroxy-benzene-carboximidamide (2.7 g, 9.9 mmol) was added to 5 ml of pyridine with stirring under nitrogen and 1.95 g (18.7 mmol) of cyclopropylcarbonyl chloride was added dropwise, and the resulting mixture was stirred 15 min, heated at 65° C. overnight, and heated at 75° C. for 5 h. The reaction mixture was cooled, diluted with water, and stored in freezer. The aqueous layer was decanted and the gummy solid was washed with water. The solid was dissolved in methylene chloride, dried over magnesium sulfate, filtered through silica and Florisil, and concentrated in vacuo to provide 3.79 g of a yellow oil. The oil was purified by silica gel column chromatography eluting with 20% ethyl acetate in hexane to afford 1.24 g of the title compound, which upon drying at 49° C./0.001 mm. yielded 920 mg of white needles, m.p. 60°–62° C.

EXAMPLE 56 a) Tetrahydro-2-(4-pentynyloxy)pyran.

4-Pentyne-1-ol ( 8.41 g, 100 mmol), 13.7 ml (150 mmol) of 3,4-dihydro-2H-pyran, 2.5 g (10 mmol) of pyridinium p-tosylate, and 100 ml of methylene chloride were combined with stirring under nitrogen and the mixture was stirred at room temperature for 1 h. The mixture was partitioned between 100 ml of water and 150 ml of ether, the organic layer was washed with 100 ml of water and brine, and dried over magnesium sulfate. The ether solution was filtered through a plug of silica and concentrated in vacuo to provide 17.77 g of a pale yellow liquid. The oil was purified by flash silica gel (250 g) column chromatography, eluting with 10 % ethyl acetate in hexane to afford 14.75 g (87.8 %) of the title compound as a pale yellow oil.

b) Ethyl chloroximidoacetate (5.4 g, 35.6 mmol) was dissolved in 12 ml of N-methyl-2-pyrrolidinone (NMP) wth stirring under nitrogen, and the solution was chilled to 0° C. in an ice bath. To the above solution was added dropwise tetrahydro-2-(4-pentynyloxy)pyran (2 g, 11.9 mmol) in 10 ml of NMP over a 25 min period. The reaction mixture was heated to 85° C., 4.97 ml of triethylamine in 20 ml of NMP was added dropwise over an 1 h period, and the mixture was heated (85° C.) for an additional 15 min. The mixture was cooled, diluted with 100 ml of water, extracted with ethyl acetate (3×), and the organic layer was washed with water and brine, and dried over magnesium sulfate. The organic solution was passed through a pad of Florisil and concentrated in vacuo to provide an orange oil (4.95 g) which was purified by filtering through a pad of silica gel (50% ethyl acetate in hexane) followed by MPLC (120 g Silica Gel 60, 15% ethyl acetate in hexane, 25 ml/min) to provide 1.69 g (fraction 29–47) of the desired compound as a clear oil.

c) The compound of 56b, (1.4 g (0.508 mmol) and 10 ml of acetic acid/water (1:1) were combined with stirring, and the mixture was heated at 60° C. for 3 h, cooled, and diluted with water. The mixture was diluted with water, extracted with ethyl acetate (3×), and the organic layer was washed with brine and dried over magnesium sulfate. The ethyl acetate solution was concentrated in vacuo to provide 920 mg of a pale yellow oil which was purified by MPLC (120 g Silica Gel 60, 20% ethyl acetate in hexane, 25 ml/min) affording 0.5 g (50%) of a compound of formula I ($R_1$=phenoxycarbonyl, Y=$(CH_2)_3$, $R_2$ and $R_3$=2, 6-dimethyl, $R_4$=trifluoromethyl, $R_5$=hydrogen).

d) The compound of formula I ($R_1$=carboxy, Y=$(CH_2)_3$, $R_2$ and $R_3$=2,6-dimethyl, $R_4$=trifluoromethyl, $R_5$=hydrogen). 3-(phenoxycarbonyl)-5-[3-(hydroxy)propyl]isoxazole from example 56c (0.42 g, 2.1 mmol), 0.6 g (2.32 mmol) of 2,6-dimethyl-4-(5-trifluoromethyl-1,2,4-oxadiazol-3-yl)phenol, and 0.61 g of triphenylphosphine were combined in 10 ml of THF under nitrogen with stirring. The mixture was chilled to 0° C. and 0.4 g of diethyl azodicarboxylate (DEAD) in 15 ml of THF was added dropwise over a 30 min period. The mixture was diluted with water, extracted with ethyl acetate, and the organic layer was washed with water, 10% NaOH solution, water, brine, and dried over magnesium sulfate. The organic solution was concentrated in vacuo to provide 1.51 g of a yellow solid which was purified by flash chromatography (100 g silica gel 60, 20% ethyl acetate) to afford 520 mg of a white solid. The solid product was recrystallized from ethanol and dried (44° C./0.001 mm) to afford 170 mg of a white solid, m.p. 70°–71° C.

e) The compound of formula I ($R_1$=carboxy, Y=$(CH_2)_3$, $R_2$ and $R_3$=2,6-dimethyl, $R_4$=trifluoromethyl, $R_5$=hydrogen) 5-{3-[2,6-Dimethyl-4-(5-trifluoromethyl-1,2,4-oxadiazol-3-yl)phenoxy]propyl}-3-(ethoxycarbonyl) isoxazole (520 mg, 11.8 mmol) was suspended in 15 ml of ethanol/water(9:1) and 38 mg (15.74 mmol) of LiOH was added, and the resulting mixture was stirred at room temperature overnight. The mixture was diluted with water, extracted with ether (3×). The aqueous layer was acidified with glacial acetic acid, extracted with ether, and the organic layer was washed with brine and dried over magnesium sulfate. The solvent was concentrated in vacuo and the oil residue was thoroughly washed with cold water, dissolved in ethyl acetate/hexane, and dried over magnesium sulfate. The solvent was concentrated in vacuo to provide 407 mg of a white solid which was recrystallized from ethanol to afford 313 mg of the title compound, m.p. 138.5°–140.5° C.

EXAMPLE 57

5-{3-[2,6-Dimethyl-4-15-trifluoromethyl-1,2,4-oxadiazol-3-yl)phenoxy]-propyl}-3-(methyl)-4-(bromo)isoxazole.

[$R_1$=methyl, Y=$(CH_2)_3$, $R_2$ and $R_3$=2,6-dimethyl, $R_4$=trifluoromethyl, $R_5$-bromo].

5-{3-[2,6-Dimethyl-4-(5-trifluoromethyl-1,2,4-oxadisazol-3-yl)phenoxy]-propyl}-3-methylisoxazole (690 mg, 1.8 mmol), 0.1 ml (2.0 mmol) of bromine, and 2 ml of glacial acetic acid were combined with stirring, and the mixture was stirred at room temperature for 2 days. Additional bromine (0.1 ml) was added, the mixture was stirred at room temperature for three more days. The mixture was diluted with water, the solid product was filtered, washed with water, and recrystallized from methanol to provide 680 mg of the title compound, m.p.79°–80°

EXAMPLE 58 a) 5-{3-[2,6-Dimethyl-4-(5-oxo-4,5-dihydro-1,2,4-oxadiazol-3-yl)phenoxy]-propyl}-3-methylisoxazole.

[$R_1$=$CH_3$, Y=($CH_2$)$_3$, $R_2$ and $R_3$=2,6-dimethyl, $R_4$=OH, $R_5$=hydrogen].

To a mixture of 3,5-dimethyl-4-[3-(3-methylisoxazol-5yl)propyloxy]-N-hydroxy-benzenecarboximidamide(3.03 g, 10 mmol) and potassium carbonate (1.52 g, 11 mmol) in 30 ml of acetone, cooled to 0° C. under nitrogen, was added dropwise a solution of ethyl chloroformate (1.05 ml, 11 mmol) in 5.5 ml of acetone and the mixture was stirred at 0° C. for 1 h, and then at room temperature for overnight. The mixture was poured into water, the aqueous layer was extracted with methylene chloride, and the organic layer was washed with brine, and dried over magnesium sulfate. The organic solution was filtered through Florisil and concentrated in vacuo to provide a yellow solid. The solid product was heated slowly to 130° C. in vacuo for 70 min during which time the product melted and resolidified. The product was washed with ether and dried in vacuo overnight to afford 2.51 g (76.3%) of the title compound, as a light tan solid. The product was recrystallized from methanol, m.p. 194°–5° C.

b) 5-{3-[2,6-dimethyl-4-(5-chloro-1,2,4-oxadiazol-3-yl)phenoxy]-propyl}-3-methylisoxazole [$R_1$=$CH_3$, Y=($CH_2$)$_3$, $R_2$ and $R_3$=2,6-dimethyl, $R_4$=Cl, $R_5$=hydrogen].

Dry pyridine (0.59 ml ,7.5 ml) was added to 7 ml (75 mmol) of phosphorous oxychloride. To the mixture was added 5-{3-[2,6-dimethyl-4-(5-oxo-4,5-dihydro-1,2,4-oxadiazol-3-yl)phenoxy]propyl}-3-methylisoxazole (2.47 g, 7.5 mmol) and the resulting mixture was heated at 128° C. for 7 h. The mixture was cooled in an ice bath, poured onto 125 ml of crushed ice. After the excess $POCl_3$ is destroyed, the mixture was extracted with ethyl acetate (2×50 ml), and the organic layer was washed with saturated sodium bicarbonate solution and brine, and dried over magnesium sulfate. The solvent was concentrated in vacuo and the residue was dissolved in methylene chloride, filtered through Florisil, and concentrated in vacuo to provide 2.34 g of the title compound as a yellow oil. MPLC (silica gel 60, 26×460 mm, 12% ethyl acetate in hexane, 20 ml/min) provided 2.13 g (81.6%) of the title compound, m.p. 71°–71° C.

c) 5-{3-[2,6-Dimethyl-4-(5-sulfo-4,5-dihydro-1,2,4-oxadiazol-3-yl)phenoxy]-propyl}-3-methylisoxazole. [$R_1$=$CH_3$, Y=($CH_2$)$_3$, $R_2$ and $R_3$=2,6-dimethyl, $R_4$=SH, $R_5$=hydrogen].

To a suspension of sodium hydride (48 mg, 7.5 mmol) in dry, degassed N-methylpyrrolidione was condensed methanethiol. Gas evolution was observed. To this solution was added dropwise a solution of 5-{3-[2,6-dimethyl-4-(5-chloro-1,2,4-oxadiazol-3-yl)phenoxy]-propyl}-3-methylisoxazole (348 mg,1 mmol) in 2 ml of dry and degassed NMP. After 2 h, the mixture was poured into 25 ml of of saturated ammonium chloride solution and washed with ether (2×25 ml). The aqueous layer was acidified with conc. HCl solution and the solid product was filtered, washed with water and ether, and air dried to provide 251 mg of the title compound as a white powder, m.p. 162°–165° C. (d).

d) 5-{3-[2,6-dimethyl-4-(5-methylthio-1,2,4-oxadiazol-3-yl)phenoxy]-propyl}-3-methylisoxazole. [$R_1$=$CH_3$, Y=($CH_2$)$_3$, $R_2$ and $R_3$=2,6-dimethyl, $R_4$=methyl-thio, $R_5$=hydrogen].

5-{3-[2,6-Dimethyl-4-(5-thio-4,5-dihydro-1,2,4-oxadiazol-3-yl)phenoxy]-propyl}-3-methylisoxazole (0.35 g, 1 mmol) and 0.17 g (1.2 mmol) of potassium carbonate were combined in 3.5 ml of acetone with stirring under nitrogen. The mixture was chilled to 0° C. in an ice bath for 1 h and 0.156 g (1.1 mmol) of methyl iodide as added and the resulting mixture was stirred at 0° C. for 1 h. The mixture was diluted with 5 ml of water, extracted with ether (3×), and the organic layer was washed with brine and dried over magnesium sulfate. The ether solution was concentrated in vacuo to provide a pale yellow solid (310 mg) which was purified by flash silica gel column (1.6×11, 50% ethyl acetate in hexane) chromatography affording 300 mg (83.3%) of the title compound.

EXAMPLE 59

5-{3-[2,6-dimethyl-4-(5-methylthiomethyl-1,2,4-oxadiazol-3-yl)phenoxy]propyl}-3-methylisoxazole.

[$R_1$=$CH_3$, Y=($CH_2$)$_3$, $R_2$ and $R_3$=2,6-dimethyl, $R_4$=methylthiomethyl, $R_5$=hydrogen].

Methanesulfide (15 drops condensed via cold finger at −78° C.) was condensed into a stirred solution of 480 mg (0.96 mmol) of the compound of example 42 and DIPEA (250 mg) in 10 ml of methylene chloride under nitrogen, and the mixture was stirred at room temperature for 1 h. The mixture was partitioned between 20 ml of water and 10 ml of ether, and the aqueous layer was extracted with ether (3×). The combined organic layer was washed with, brine, dried ($MgSO_4$), and passed through flash chromatography (silica gel, 1.6×23, 20% ethyl acetate in hexane) to provide 360 mg (100%) of the title compound which was recrystallized from methanol, m.p. 79.5°–80° C.

EXAMPLE 60 a) 4-Cyano-2-fluorophenol,

4-Bromo-2-fluorophenol (10 ml, 91 mmol) and 9.85 g (0.11 mol) of CuCN were combined in 75 ml of NMP with stirring under nitrogen, and the mixture was heated at 150° C. for 5 h. The mixture was diluted with 200 ml of ether, stirred, and decanted. The residue was diluted again with 200 ml of ether, heated, and decanted. The combined decantates were washed with water, 1N HCl solution, water, and brine, and dried over magnesium sulfate. The organic solution was concentrated in vacuo to provide 12 g of a white solid which was triturated in carbon tetrachloride and filtered to afford 7.29 g (72.1%) of the title compound.

b) 4-Cyano-2-fluoro-6-iodophenol

Potassium iodide (7.97 g, 48 mmol) was dissolved in 125 ml of DMF with stirring, and 4-cyano-2-fluorophenol (16a; 5.56 g 48 mmol) and chloramine-T in 75 ml of DMF were added dropwise with stirring. The reaction mixture was poured into 650 ml of water, acidified with 6N HCl, and extracted with ethyl acetate. The organic layer was washed with 10% $NaHSO_3$, water and brine and dried over magnesium sulfate. The organic solution was concentrated in vacuo and the yellow solid residue was treated with 200 ml of 1N NaOH solution, filtered through supercel, and the filtrate was acidified with conc. HCl solution. The solid product was filtered, dried, dissolved in ether, and the organic layer was dried over magnesium sulfate. The organic solution was concentrated in vacuo and the residue was recrystallized from ethylene chloride to afford 5.93 g (55.6%) of the title compounds.

c) 3-Fluoro-5-iodo-4-[3-(3-methylisoxazol-5yl)propyloxy] phenylcyanide, 3-(3-Methylisoxazol-5yl)propyl chloride (4.65 g, 28 mmol), 6.35 g (46 mmol) of potassium carbonate, 4.65 g (28 mmol) of potassium iodide, and 5.93 g (30 mmol) of 2-fluoro-6-iodo-4-cyanophenol (16b) were combined in 50 ml of N-methyl-2-pyrrolidinone with stirring, and the mixture was heated at 110° C. for 2h and stirred at room temperature overnight. The mixture was diluted with 2N NaOH solution, stirred, filtered and dried to provide a tan solid. The product was filtered through a plug of silica gel with methylene chloride and the solvent was concentrated in vacuo to provide 7.91 g of a yellow oil. The product was crystallized from methanol and purified by MPLC (silica gel 60, hexane/ethyl acetate (8:2) to afford 7.04 g of the title compound as a white solid, m.p.69°–70° C.

d) 3-Fluoro-5-iodo-4-[3-(3-methylisoxazol-5yl)propyloxy]-N-hydroxy-benzenecarboximidamide.

3-Fluoro-5-iodo-4-[3-(3-methylisoxazol-5yl)propyloxy] phenylcyanide (16c, 1.16 g, 3 mmol), 1.04 g (15 mmol) of hydroxylamine hydrochloride, and 2.07 g of potassium carbonate were combined in 50 ml of absolute ethanol with stirring , and the mixture was refluxed for 12 h. The mixture was filtered and the filtrate concentrated in vacuo to provide 1.95 g of the title compound as a white solid. The product was triturated in 75 ml of ether, filtered through Florisil and concentrated to afford 1.17 g (93%) of the title compound as viscous oil.

e) 5-{3-[2-Fluoro-6-iodo-4-(5-trifluoromethyl-1,2,4-oxadiazol-3-yl)phenoxy]propyl}-3-methylisoxazole.

[$R_1$=$CH_3$, Y=$(CH_2)_3$, $R_2$ and $R_3$=2-fluoro-6-iodo, $R_4$=trifluoromethyl, $R_5$=hydrogen].

3-Fluoro-5-iodo-4-[3-(3-methylisoxazol-5yl)propyloxy]-N-hydroxy-benzene-carboximidamide(16d; 613 mg, 1.46 mmol) was dissolved in 2 ml of pyridine with stirring under nitrogen and heated to 85° C. in an oil bath. To the above solution 0.6 ml (4.25 mmol) of trifluoroacetic anhydride was added dropwise and the mixture was stirred for 1 min at 85° C. and cooled. The mixture was diluted with water, the white solid product was collected by filtration and recrystallized from methanol to afford 280 mg of the title compound, m.p. 79°–80° C.

f) 3-Fluoro-5-methyl-4-[3-(3-methylisoxazol-5yl) propyloxy]phenylcyanide.

3-Fluoro-5-iodo-4-[3-(3-methylisoxazol-5yl)propyloxy] phenylcyanide (3.86 g, 1 mmol), 1.7 ml (12 mmol) of tetramethyltin, 300 mg (0.43 mmol) of bis (triphenylphosphine)palladium chloride, and 50 ml of N-methyl-2-pyrrolidinone were combined with stirring under nitrogen, and the mixture was heated at 120° C. for 2 h and cooled. The mixture was poured directly onto a large plug of silica gel moistened with methylene chloride and eluted with methyene chloride. The organic solution was washed with water and brine, and the organic layer was dried over magnesium sulfate, filtered, and concentrated to provide 3.8 g of an orange oil. The product was crystallized from water, triturated and recrystallized from methanol to afford 2.3 g ( 84%) of the title compound as a yellow solid, m.p.42°–43° C.

g) 3-Fluoro-5-methyl-4-[3-(3-methylisoxazol-5yl) propyloxy]-N-hydroxy-benzenecarboximidamide.

3-Fluoro-5-methyl-4-[3-(3-methylisoxazol-5yl) propyloxy]phenylcyanide ( 16f, 1.05 g, 3.83 mmol), 1.32 g (19 mmol) of hydroxylamine hydrochloride, and 2.63 g (19 mmol) of potassium carbonate were combined in 50 ml of absolute ethanol with stirring , and the mixture was stirred at room temperature for 16 h. The mixture was filtered and the filtrate concentrated in vacuo to provide 1.31 g of the title compound as a white solid. The product was triturated in water, filtered, and dried to provide 1.13 g (96%) of the title compound as a white solid, m.p. 135°–137° C.

h) 5-{3-[2-Fluoro-6-methyl-4-(5-trifluoromethyl-1,2,4-oxadiazol-3-yl)phenoxy]propyl}-3-methylisoxazole.

[$R_1$=$CH_3$, Y=$(CH_2)_3$, $R_2$ and $R_3$=2-fluoro-6-methyl, $R_4$=trifluoromethyl, $R_5$=hydrogen].

3-Fluoro-5-methyl-4-[3-(3-methylisoxazol-5yl) propyloxy]-N-hydroxy-benzene-carboximidamide(16 g; 500 mg, 1.63 mmol) was suspended in 2 ml of pyridine at room temperature with stirring under nitrogen. To the above solution was added dropwise 0.35 ml (2.5 mmol) of trifluoroacetic anhydride (exothermic reaction) and the resulting mixture was refluxed for 2 h. The mixture was partitioned between water and ether, the organic layer was washed with 1N HCl solution, water, and brine, and dried over magnesium sulfate. The organic solution was concentrated in vacuo and the residue was filtered through a plug of silica gel eluting with methylene chloride to provide 300 mg (48%) of the title compound, as a white solid, m.p. 45°–46° C.

EXAMPLE 61 a) 2-Chloro-4,6-diiodophenol.

Sodium iodide (5.4 g, 15 mmol) in 100 ml of DMF was heated to 40°–50° C. and the resulting solution was cooled to room temperature. To the above solution 8.93 g (30 mmol) of chloramine-T was added. After 15 min, an additional 5 mmol of chloramine-T was added and the mixture was allowed to react at room temperature for 1 h. The reaction mixture was concentrated in vacuo, the residue was suspended in 300 ml of water, filtered and the filtrate was acidified with conc. HCl solution to pH 2–3. The solid product and aqueous layer was extracted with ethyl acetate (3×), the combined organic layer was dried ($MgSO_4$) and concentrated in vacuo. The dark brown residue was disolved in methylene chloride, washed with sodium thiosulfate solution (2×), dried, and concentrated in vacuo to provide a white solid. The solid product was purified by silica gel column chromatography (20% ethyl acetate in hexane) to provide 5.45 g (96%) of the title compound as a white solid.

b) 2,4-Diiodo-6-chloro-4-[3-(3-Methylisoxazol-5yl] propyloxy]benzene.

3-(3-Methylisoxazol-5yl)propyl chloride (3 g, 7.9 mmol), 0.5 g of potassium iodide, 1.8 g (11.7 mmol) of 2,4-diiodo-6-chlorophenol, and 2.7 g (19.8 mmol) of potassium carbonate were combined in 45 ml of NMP under nitrogen, and the mixture was heated at 60° C. with stirring for 3.5 h. The mixture was poured into water, acidified to pH 3–4 with 2N HCl solution, and extracted with ethyl acetate (3×). The combined organic layer was dried ($MgSO_4$), filtered, and concentrated to provide a yellow oil. The oil was dissolved in methylene chloride and purified by silica gel chromatography (15% ethyl acetate in hexane) to provide 2.85 g (72%) of the title compound as a white solid, m.p. 66°–68° C.

c) 2,4-Dicyano-6-chloro-4-[3-(3-Methylisoxazol-5yl) propyloxy]benzene.

2,4-Diiodo-6-chloro-4-[3-(3-Methylisoxazol-5yl) propyloxy]benzene (1.5 g, 2.97 mmol) and 622 mg of CuCN were combined in 6 ml of DMF under nitrogen, and the mixture was heated at 120° C. for 7 h (during which time an additional 100 mg of CuCN added). The mixture was poured into 100 ml of 2N HCl and 100 ml of ethyl acetate while stirring vigorously for 1 h and filtered. The solid residue was partitioned (2×) again in 100 ml of ethyl acetate/2N HCl (1:1). The aqueous layer was extracted with ethyl acetate (3×), and the combined organic layer was dried (MgSO$_4$), and concentrated. The solid residue gas suspended in ether, filtered, and dried in vacuo to provide 539 mg (60%) of the title compound.

d) 4-[3-(3-methylisoxazol-5yl)propyloxy]-2-cyano-6-chloro-N-hydroxybenzenecarboximidamide.

4-[3-(3-Methylisoxazol-5yl)propyloxy]-2,4-dicyano-6-chlorobenzene ( 17c, 300 mg, 0.99 mmol), 124 mg (1.79 mmol) of hydroxylamine hydrochloride, and 683 mg (4.95 mmol) of potassium carbonate were combined in 10 ml of ethanol with stirring, and the mixture was refluxed under nitrogen for 75 min. The mixture was filtered while hot, the residue was washed with hot ethanol and methylene chloride, and the filtrate concentrated in vacuo to provide 320.4 mg (97%) of the title compound.

e) 5-{3-[4-(5-Trifluoromethyl-1,2,4-oxadiazol-3-yl)2-cyano-6-chlorophenoxy]-propyl}-3-methylisoxazole.

[R$_1$=CH$_3$, Y=(CH$_2$)$_3$, R$_2$=CN, R$_3$=Cl, R$_4$=trifluoromethyl, R$_5$=hydrogen].

Trifluoroacetic anhydride (0.328 ml, 2.4 mmol) was added neat to a stirred solution of 4-[3-(3-methylisoxazol-5yl)propyloxy]-2-cyano-6-chloro-N-hydroxy-benzenecarboximidamide(320.4 mg, 0.95 mmol) in 3 ml of pyridine (exothermic reaction) and the mixture was heated to 60°–70° C. for 1 h. The mixture was concentrated in vacuo to remove pyridine, and the residue was partitioned between water and ethyl acetate. The aqueous layer was washed with ethyl acetate, and the combined organic layer was washed with water, dried (MgSO$_4$), and concentrated in vacuo. The solid residue was triturated in hexane and recrystallized from hexane/ether (9:1) to provide 189 mg (48%) of the title compound, m.p. 70°–71° C.

EXAMPLE 62 a) 4-Iodo-2-methylphenol.

To a solution of 10 g of o-cresol and 16.5 g (1.2 equiv) NaI in 250 ml of DMF was added 31 g (1.2 equiv) of chloramine-T hydrate. The dark green solution was stirred at rt for 1.5 h. The mixture, now a heterogeneous light brown, was poured into water, acidified, extracted with ethyl acetate, and the organic phase washed with water and bisulfite solution. The organic phase was dried over MgSO$_4$. Concentration, trituration with hexane, and flash chromatography (silica gel, hexane, hexane/ethyl acetate (5:1)) provided 13.6 g (63%) of the title compound as a white solid.

b) 4-Iodo-2-methylphenol.

To a solution of 15 g of o-cresol and 24.8 g of NaI in 400 ml of DMF was added 46.5 g of chloramine-T hydrate. The dark green solution was stirred at rt for 1.5 h. The mixture, now a heterogeneous light brown, was poured into water, acidified, extracted with ethyl acetate, and the organic phase washed with water and bisulfite solution. The orange organic phase was concentrated in vacuo and the product washed thoroughly with hexane to remove the product. The hexane wash was concentrated in vacuo and purified by flash chromatography (silica gel, hexane, hexane/ethyl acetate (4:1)) to provide 20.1 g (62%) of the title compound as a white solid.

c. 2,4-Diiodo-6-methyl-4-[3-(3-methylisoxazol-5yl) propyloxy]benzene, 3-(3-Methylisoxazol-5yl)propyl chloride (3.6 g, 10 mmol), 0.25 g of potassium iodide, 3.2 g (20 mmol) of 2,4-diiodo-6-methylphenol, and 4.4 g of potassium carbonate were combined in 20 mi of NMP under nitrogen, and the mixture was heated at 60° C. with stirring for 3.5 h. The mixture was poured into water, acidified to pH 3°–4 with 2N HCl solution, and extracted with ethyl acetate (3×). The combined organic layer was dried (MgSO$_4$), filtered, and concentrated to provide a yellow oil. The oil was dissolved in methylene chloride and purified by silica gel chromatography (12–15% ethyl acetate in hexane) followed by crystallization from ethanol and drying at 0.44 mm to provide 2.72 g of the title compound as a white solid, m.p. 71.5°–73° C.

d) 2,4-Dicyano-6-methyl-4-[3-(3-methylisoxazol-5yl) propyloxy]benzene.

2,4-Diiodo-6-methyl-4-[3-(3-methylisoxazol-5yl) propyloxy]benzene (270 mg, 0.56 mmol) and 130 mg of CuCN were combined in 0.7 ml of DMF under nitrogen, and the mixture was heated at 115° C. for 2 h. Water and methylene chloride were added to the mixture, heated briefly, and filtered (this process was repeated 3×). Ethyl acetate/water was added to the residue, heated briefly, and filtered (this process was repeated). The combined organic layer was dried over MgSO$_4$, concentrated, and the residue was purified by flash chromatography (silica gel, 25% ethyl acetate in hexane) followed by ethanol crystallization to provide 105 mg of the title compound as a white solid, m.p. 46°–48° C.

e) 4-[3-(3-methylisoxazol-5yl)propyloxy]-2-cyano-6-chloro-N-hydroxy-benzenecarboximidamide.

4-[3-(3-Methylisoxazol-5yl)propyloxy]-2,4-dicyano-6-methylbenzene ( 18d, 281 mg, 1 mmol), 175 mg (2.5 mmol) of hydroxylamine hydrochloride, and 700 mg (5 mmol) of potassium carbonate were combined in 4 ml of ethanol with stirring, and the mixture was refluxed (85°–95° C.) under nitrogen for 4 h. The mixture was diluted with methylene chloride, filtered, triturated with methylene chloride/ethanol and filtered. The filtrate was concentrated in vacuo and the residue was dried to provide 330 mg of the title compound as a yellow gum.

f) 5-{3-[4-(5-Trifluoromethyl-1,2,4-oxadiazol-3-yl)2-zyano-6-chlorophenoxy]-propyl}-3-methylisoxazole.

[R$_1$=CH$_3$, Y=(CH$_2$)$_3$, R$_2$=CN, R$_3$=Cl, R$_4$=cyclohexyl, R$_5$=hydrogen].

To a stirred solution of 4-[3-(3-methylisoxazol-5yl) propyloxy]-2-cyano-6-chloro-N-hydroxy-benzenecarboximidamide(330 mg, 1 mmol) in 2.5 ml of pyridine was added trifluoroacetic anhydride (0.328 ml) was added dropwise over an 1 min period, and the mixture was heated at 60° C. for 1 h. The mixture was concentrated in vacuo to remove pyridine, and the residue was partitioned between ether and 1N HCl solution. The aqueous layer was extracted with ether (3×), and the combined organic layer was washed with water and saturated sodium bicarbonate solution, and dried (MgSO$_4$). The solvent was concentrated in vacuo, the solid residue was purified by flash chromatography (silica gel, 20–25% ethyl acetate/hexane;) followed by recrystallization from ethanol to provide 182 mg (46%) of the title compound as a white solid, m.p. 63°–64° C. From an earlier fraction (flash chromatography), 6 mg of 5-{3-[2, 4-bis(5-trifluoromethyl-1,2,4-oxadiazol-3-yl)-6-chlorophenoxy]-propyl}-3-methyl-isoxazole was obtained as a by-product.

EXAMPLE 63 a) 2-Methyl-4-cyano-6-methylphenol.

2-Chloro-4-bromo-6-chlorophenol (1 g, 4.5 mmol) and 600 mg of CuCN were combined in 5 ml of DMF under nitrogen, and the mixture was heated at 120° C. for 5 h. The mixture was partitioned between 2N HCl solution and ethyl acetate, the aqueous layer was extracted with ethyl acetate (3×), and the combined organic layer was dried (MgSO$_4$) and concentrated to provide a brown oil. The oil residue was dissolved in minimal methylene chloride and passed through silica gel column eluting with 10% ethyl acetate in hexane to provide 210 mg (28%) of the title compound as a white solid, m.p. 41°–42° C.

b) 2-chloro-4-cyano-6-methyl-4-[3-(3-methylisoxazol-5yl)propyloxy]benzene.

3-(3-Methylisoxazol-5yl)propyl chloride (143 mg, 0.9 mmol), 0.1 g of potassium iodide, 0.1 g (0.6 mmol) of 2-chloro-4-cyano-6-methylphenol, and 0.207 g of potassium carbonate were combined in 2 ml of NMP under nitrogen, and the mixture was heated at 60° C. with stirring overnight. The mixture was partitioned between water/ethyl acetate, the aqueous layer was extracted with ethyl acetate (3×) and the combined organic layer was dried over MgSO$_4$. The solvent was concentrated in vacuo, the yellow oil residue was dissolved in methylene chloride and passed through silica gel column eluting with 10–20% ethyl acetate in hexane to provide 126 mg (72%) of the title compound as a white solid, m.p. 100°–101° C.

c) 4-[3-{3-methylisoxazol-5-yl)propyloxy]-2-chloro-6-methyl-N-hydroxy-benzenecarboximidamide.

2-Chloro-4-cyano-6-methyl-4-[3-(3-methylisoxazol-5-yl) propyloxy]benzene (19b, 4.2 g, 14 mmol), 1.8 g (26 mmol) of hydroxylamine hydrochloride, and 9.66 g (70 mmol) of potassium carbonate were combined in 100 ml of ethanol with stirring under nitrogen, and the mixture was refluxed for 6.5 h. The mixture was filtered while hot, the residue was washed with hot ethanol. The filtrate was concentrated in vacuo to remove ethanol. The solid residue was dissolved in methylene chloride, filtered, and concentrated in vacuo. The solid product was triturated with ether and filtered to provide 4.06 g (90%) of the title compound as a white solid.

d) 5-{3-[4-(5-Trifluoromethyl-1,2,4-oxadiazol-3-yl)2-chloro-6-methylphenoxy]propyl}-3-methylisoxazole.

[$R_1$=Ch$_3$, Y=(CH$_2$)$_3$, $R_2$=Cl, $R_3$=methyl, $R_4$=trifluoromethyl, $R_5$=hydrogen].

4-[3-(3-Methylisoxazol-5-yl)propyloxy]-2-chloro-6-methyl-N-hydroxy-benzenecarboximidamide (400 mg, 1.2 mmol) was dissolved at room temperature under nitrogen in 3 ml of pyridine. To the above solution was added trifluoroacetic anhydride (0.423 ml, 3 mmol)) was added dropwise, and the mixture was stirred at room temperature for 2 h. The residue was partitioned between water/ether, the aqueous layer was extracted with ethyl acetate (3×). The combined organic layer was dried (MgSO$_4$), filtered and concentrated in vacuo to provide a yellow oil. The oil, in a minimum volume of methylene chloride, was purified by flash chromatography (silica gel, 10% ethyl acetate/hexane) to provide 165 mg (34%) of the title compound as a white solid, m.p. 55°–56.5° C.

EXAMPLE 64

Using the product of Example 18 and acetic anhydride there was prepared 5-{3-[2,6-Dimethyl-4-(5-acetamido-1,2,4-oxadiazol-3-yl)phenoxy]-propyl}-3-methylisoxazole, ($R_1$=methyl, $R_2$, $R_3$=2,6-dimethyl, $R_4$=acedamido, $R_5$=hydrogen, 4=1,3propylene), m.p. 137°–138° C.

EXAMPLE 65

Using the method of Example 1a–e but substituting 3-methyl 4-hydroxybenzonitrile for 3,5-dimethyl-4-hydroxybenzonitrile in 1c a compound of formula I ($R_1R_2$=methyl 1, $R_3$=hydrogen, $R_4$=trifluoromethyl, $R_5$=hydrogen, Y=1,3 propylene); 5-{3-[2-methyl-4-(5-trifluoromethyl-1,2,4-oxadiazol-3-yl)phenoxy]-propyl}-3-methylisoxazole, m.p. 69°–70° C. was obtained.

EXAMPLE 66

Using the product of Example 1d, and reacting it with α,α difluoropropionic andydride, one obtains a compound of formula I ($R_1$=methyl $R_2$, $R_3$=2,6-dimethyl, $R_4$=1,1 difluoroethyl, $R_5$=hydrogen, Y=1,3 propylene); 5-{3-[2,6-Dimethyl-4-(5-(1,1-difluoroethyl)-1,2,4-oxadiazol-3-yl)phenoxy]-propyl}-3-methylisoxazole m.p. 64°–65° C.

Following a procedure similar to that of Example 1d but substituting for the product from Example 1c an equivalent amount of the above compounds of formula IX there can be obtained respectively the following compounds of formula V:

4-[3-(3-methylisoxazol-5-yl)propyloxy]-3-nitro-N-hydroxybenzenecarboximidamide 3,5-dimethoxy-4-[3-(3-methylisoxazol-5-yl)propyloxy]-N-hydroxybenzenecarboximidamide 4-[3-(3-methylisoxazol-5-yl)propyloxy]-3-trifluoro-methyl-N-hydroxybenzenecarboximidamide.

EXAMPLE 67

Using a method substantially the same as the method of example 1a to 1e, but replacing 3,5 dimethyl-4-hydroxybenzonitrile in 1c with and equivalent molar amount of 3-methoxy-5-methyl-4-hydroxybenzonitrile, a compound of formula 1 ($R_1$=methyl, $R_2$=3-methoxy, $R_3$=5-methyl, $R_4$=trifluromethyl, $R_5$=hydrogen, Y=1,3 propylene) 5-{3-[2-methoxy-6-methyl-4-(5-trifluoromethyl-1,2,4-oxadiazole-3-yl)phenoxy]propyl}-3-methylisoxazole was obtained, m.p. 35.5°–37° C.

EXAMPLE 68

Using a method substantially the same as the method of example 1a to 1e, but replacing 3,5 dimethyl-4-hydroxybenzonitrile in 1c with and equivalent molar amount of 3-methoxy-5-methyl-4-hydroxybenzonitrile, and replacing trifloroacetic anhydride with difluoroacetic anhydride in the step described in example 1e a compound of formula 1 ($R_1$=methyl, $R_2$=3-methoxy, $R_3$=5-methyl, $R_4$=difluoromethyl, $R_5$=hydrogen, Y=1,3 propylene) 5-{3-[2-methoxy-6-methyl-4-(5-difluoromethyl-1,2,4-oxadiazole-3-yl)phenoxy]propyl)-3-methylisoxazole was obtained, m.p. 71°–72° C.

The ethylnyl compound of formula XIII, from example 20a was acetylated using trifluoroacetyl chloride, and then was reacted with a twofold excess of hydroxylamine hydrochloride according to the method of example 20 b. A compound of formula I was obtained substantially by the method of 20c ($R_1$=trifluoromethyl, $R_2$, $R_3$=3,5-dimethyl, $R_4$=trifluoromethyl, $R_5$=hydrogen, Y=1,3 propylene), 5-{3-[2,6-dimethyl-4-(5-trifluoromethyl-1,2,4-oxadiazole-3-yl)phenoxy]propyl}-3-trifluoromethylisoxazole m.p. 60°–61° C.

Following a procedure similar to that of Example 1e but substituting for the product of Example 1d an equivalent amount of the above compounds of formula V there can be obtained respectively the following compounds of formula I:

3-methyl-5-{3-[2-nitro-4-(5-trifluoromethyl-1,2,4-oxadiazol-3-yl)phenoxy]propyl}isoxazole [I; $R_1=Ch_3$, $Y=(CH_2)_3$, $R_2=2-NO_2$, $R_3=H$, $R_4=CF_3$, $R_5=$hydrogen]

5-{3-[2,6-dimethoxy-4-(5-trifluoromethyl-1,2,4-oxadiazol-3-yl)phenoxy]propyl}-3-methylisoxazole [I; $R_1=CH_3$, $Y=(CH_2)_3$, $R_2$ and $R_3=2,6-(OCH_3)_2$, $R_4=CF_3$, $R_5=$hydrogen]

3-methyl-5-(3-[2-trifluoromethyl-4-(5-trifluoromethyl-1,2,4-oxadiazol-3-yl)phenoxy]propyl}isoxazole [I; $R_1=Ch_3$, $Y=(CH_2)_3$, $R_2=2-CF_3$, $R_3=H$, $R_4=CF_3$, $R_5=$hydrogen].

Following the procedures of Example 20a, b and c and using equivalent amounts of reactants in each case but substituting in Example 20a 11-chloro-1-undecyne for 5-chloro-1-pentyne there can be obtained successively the following:

3,5-dimethyl-4-(9-ethinylnonyloxy)benzonitrile;

3,5-dimethyl-4-(9-ethinylnonyloxy)-N-hydroxy-benzenecarboximidamide; and

3-[3,5-dimethyl-4-(9-ethinylnonyloxy)phenyl]-5-trifluoromethyl-1,2,4-oxadiazole.

Following Procedure 1 and using equivalent amounts of acetaldehyde oxime and 3-[3,5-dimethyl-4-(9-ethinylnonyloxy)phenyl]-5-trifluoromethyl-1,2,4-oxadiazole, there can be obtained 5-{9-[2,6-dimethyl-4-(5-trifluoro-methyl-1,2,4-oxadiazol-3-yl)phenoxy]nonyl}-3-methylisoxazole [I; $R_1=CH_3$, $Y=(CH_2)_9$, $R_2$ and $R_3=2,6-(CH_3)_2$, $R_4=CF_3$, $R_5=$hydrogen].

Following Procedure 1 and using equivalent amounts of n-hexyl aldehyde oxime and the product of Example 20c, there can be obtained 5-{3-[2,6-dimethyl-4-(5-trifluoromethyl)phenoxy]propyl}-3-(n-pentyl)isoxazole [I; $R_1=(CH_2)_4CH_3$, $Y=(CH_2)_3$, $R_1$ and $R_2=2,6-(CH_3)_2$, $R_4=CF_3$, $R_5=$hydrogen].

Following the procedure of Example 37 but substituting an equivalent amount of n-pentyl bromide for the ethyl iodide, there can be obtained 5-{3-[4-(5-cyclopropyl-1,2,4-oxadiazol-3-yl)phenoxy]propyl}-3-pentyloxyisoxazole [I; $R_1=O(CH_2)_4CH_3$, $Y=(CH_2)_3$, $R_1$ and $R_2=2,6-(CH_3)_2$, $R_4=$cyclopropyl, $R_5=$hydrogen].

Following the procedure of Example 37 but substituting equivalent amounts of the product of Example 40 and n-pentyl bromide for the product of Example 36b and ethyl iodide respectively, there can be obtained 5-{3-[2,6-dimethyl-4-(5-(n-pentyloxymethyl)-1,2,4-oxadiazol-3-yl)-phenoxy]propyl}-3-methylisoxazole [I; $R_1=CH_3$, $Y=(CH_2)_3$, $R_2$ and $R_3=2,6-(CH_3)_2$, $R_4=CH_2O(CH_2)_4CH_3$, $R_5=$hydrogen].

Following the procedure of Example 1e but substituting an equivalent amount of cyclohexanecarbonyl chloride for the trifluoroacetic anhydride, there can be obtained 5-{3-[4-(5-cyclohexyl-1,2,4-oxadiazol-3-yl)-2,6-dimethylphenoxy]propyl}-3-methylisoxazole [I; $R_1=CH_3$, $Y=(CH_2)_3$, $R_1$ and $R_2=2,6-(CH3)_2$, $R_4=$cyclohexyl, $R_5=$hydrogen].

Biological evaluation of representative compounds of formula I has shown that they possess antiviral activity. They are useful in inhibiting virus replication in vitro and are primarily active against picornaviruses, including enteroviruses, echovirus and coxsackie virus, especially rhinoviruses. The in vitro testing of the representative compounds of the invention against picornaviruses showed that viral replication was inhibited at minimum inhibitory concentrations (MIC) ranging from 0.002 to 9.608 micrograms per milliliter. The test procedure used was as follows:

The MIC values were determined by an automated tissue culture infectious dose 50% (TCID-50) assay. HeLa cells in monoloyers in 96-well cluster plates were infected with a dilution of virus which had been shown empirically to produce 80% to 100% cytopathic effect (CPE) in 3 days in the absence of drug. The compound to be tested was serially diluted through 10, 2-fold cycles and added to the infected cells. After a 3 day incubation at 33° C. and 2.5% carbon dioxide, the cells were fixed with a 5% solution of glutaraldehyde followed by staining with a 0.25% solution of crystal violet in water. The plates were then rinsed, dried, and the amount of stain remaining in the well (a measure of intact cells) was quantitated with an optical density reader. The MIC was determined to be the concentration of compound which protected 50% of the cells from virus-induced CPE relative to an untreated virus control.

In the above test procedures, representative compounds of formula I were tested against some the serotypes from either a panel of fifteen human rhinovirus (HRV) serotypes, (noted in the table as panel T) namely, HRV-2, -14, -1A, -1B, -6, -21, -22, -15, -25, -30, -50, -67, -89, -86 and -41 or against some of the serotypes from a panel of 10 human rhinovirus serotypes namely HRV-3, -4, -5, -9, -16, -18, -38, -66, -75 and -61, (noted in the table as panel B) and the MIC value, expressed in micrograms per milliliter (mg/ml), for each rhinovirus serotype was determined for each virus, example 1e is given as an example of the data. Then $MIC_{50}$ and $MIC_{80}$ values, which are the minimum concentrations of the compound required to inhibit 50% and 80%, respectively, of the tested serotypes were determined. The compounds tested were found to exhibit antiviral activity against one or more of these serotypes.

The MIC values (μg/ml) obtained for the compound of Example 1e in the above-described antiviral test procedure were as follows:

TABLE I

| HRV Serotype ($MIC_{50}$) | HRV Serotype ($MIC_{50}$) | HRV Serotype ($MIC_{50}$) |
|---|---|---|
| – 2 (0.027) | –21 (0.015) | –50 (0.154) |
| –14 (0.022) | –22 (0.011) | –67 (0.070) |
| –1A (0.119) | –15 (0.147) | –89 (0.015) |
| –1B (0.054) | –25 (0.036) | –86 (0.029) |
| –6 not tested | –30 (0.047) | –41 (0.338) |

| $MIC_{50}$ | $MIC_{80}$ | Panel | N |
|---|---|---|---|
| 0.0415 | 0.119 | T | 15 |

The following Table gives the test results for representative compounds of the invention. The panel of viruses used in the test appears before the the $MIC_{80}$ and $MIC_{50}$ figure and the number of serotypes which the compound is tested against (N) is indicated after the $MIC_{80}$ and $MIC_{50}$ figure.

TABLE II

| EX. | WIN | PANEL | $MIC_{50}$ | $MIC_{80}$ | N |
|---|---|---|---|---|---|
| 1e | 63843 | T | 0.0415 | 0.119 | 15 |
| 4 | 63923 | T | 3.145 | 0.057 | 15 |
| 5 | 64173 | T | 0.153 | 0.037 | 15 |
| 6 | 64306 | T | 0.073 | 0.046 | 15 |
| 7 | 64174 | T | 99 | 99 | 14 |
| 8 | 64239 | T | 99 | 99 | 12 |

TABLE II-continued

| EX. | WIN | PANEL | MIC$_{50}$ | MIC$_{80}$ | N |
|---|---|---|---|---|---|
| 9 | 64228 | T | 0.279 | 0.141 | 14 |
| 10 | 65719 | T | 0.279 | 0.141 | 14 |
| 11 | 67483 | T | 1.9845 | 0.2485 | 12 |
| 12 | 64243 | T | 2.941 | 0.662 | 14 |
| 13 | 65996 | T | 0.266 | 0.145 | 14 |
| 14 | 66407 | T | 0.054 | 0.022 | 15 |
| 15 | 64600 | T | 99 | 99 | 14 |
| 16 | 64477 | T | 0.135 | 0.036 | 15 |
| 17 | 64527 | T | 0.116 | 0.055 | 15 |
| 18 | 64601 | T | 0.325 | 0.128 | 15 |
| 19 | 64608 | T | 0.285 | 0.085 | 14 |
| 21 | 64171 | T | 1.5645 | 0.0575 | 8 |
| 22 | 64210 | T | 0.729 | 0.087 | 15 |
| 23 | 65795 | T | 0.625 | 0.204 | 15 |
| 25 | 66457 | T | 0.312 | 0.085 | 15 |
| 26 | 66809 | T | 0.183 | 0.038 | 15 |
| 27 | 68849 | T | 0.142 | 0.087 | 15 |
| 28c | 64027 | T | 0.278 | 0.119 | 9 |
| 29d | 65650 | T | 0.172 | 0.715 | 14 |
| 30c | 65622 | T | 0.694 | 0.225 | 15 |
| 31c | 65803 | T | 99 | 0.533 | 14 |
| 32c | 66492 | T | 99 | 2.86 | 14 |
| 33 | 67440 | T | 0.102 | 0.045 | 14 |
| 34d | 65983 | T | 0.07 | 0.042 | 14 |
| 39c | 66995 | T | 0.187 | 0.035 | 15 |
| 36d | 67330 | T | 1.322 | 0.371 | 15 |
| 37 | 67372 | T | 0.352 | 0.91 | 15 |
| 38 | 64312 | T | 99 | 0.839 | 15 |
| 39 | 67366 | T | 99 | 1.848 | 15 |
| 41 | 66811 | T | 99 | 99 | 13 |
| 42 | 66810 | T | 99 | 99 | 13 |
| 43 | 67891 | T | 99 | 99 | 9 |
| 44 | 67753 | T | 0.198 | 0.385 | 14 |
| 44 | 67706 | T | 99 | 0.608 | 11 |
| 451 | 64046 | T | 0.558 | 0.153 | 13 |
| 46c | 64066 | T | 0.197 | 0.1 | 15 |
| 47 | 63924 | T | 5.145 | 0.057 | 15 |
| 48 | 67487 | T | 0.464 | 0.213 | 15 |
| 49d | 68656 | T | 99 | 99 | 9 |
| 49g | 68193 | B | 99 | 49.859 | 10 |
| 50a | 68746 | B | 49.5505 | 0.065 | 8 |
| 50b | 68835 | B | 49.578 | 0.092 | 8 |
| 50d | 68801 | B | 0.153 | 0.052 | 9 |
| 51g | 68377 | B | 99 | 0.2625 | 10 |
| 51h | 68625 | B | 0.792 | 0.135 | 10 |
| 52b | 68012 | T | 0.247 | 0.0295 | 14 |
| 52c | 68019 | T | 0.404 | 0.044 | 11 |
| 53 | 67983 | T | 0.194 | 0.072 | 15 |
| 54a | 68915 | B | 49.5925 | 0.016 | 8 |
| 54e | 64751 | T | 99 | 0.1045 | 14 |
| 56d | 64188 | T | 1.465 | 0.634 | 14 |
| 56e | 65805 | T | 99 | 5.304 | 11 |
| 57 | 68350 | B | 99 | 99 | 9 |
| 58a | 64239 | T | 99 | 99 | 12 |
| 58d | 65819 | T | 99 | 99 | 14 |
| 58e | 66458 | T | 99 | 99 | 14 |
| 60e | 68307 | B | 99 | 0.4145 | 10 |
| 60h | 68357 | B | 0.328 | 0.0315 | 10 |
| 61e | 67736 | T | 0.706 | 0.3355 | 14 |
| 62f | 67340 | T | 0.213 | 0.09 | 15 |
| 63d | 68743 | B | 0.304 | 0.13 | 7 |

Using the method described above, Example 1e was tested against other viruses.

The Minimum Inhibitory Concentration (MIC) for the 15 most commonly isolated nonpolio enteroviruses (Strikas, R. A., Anderson, L. J., and Parker, R. A., 1986; Temporal and Geographic Patterns of Isolates of Nonpolio Enterovirus in the United States, 1970–1983. J. Infect. Diseases, 153:346–351) listed below: Echovirus 3, Echovirus 4, Echovirus 5, Echovirus 6, Echovirus 7, Echovirus 9, Echovirus 11, Echovirus 24, Echovirus 30, Coxsackievirus B1, Coxsackievirus B2, Coxsackievirus B3, Coxsackievirus B4, Coxsackievirus B5, Coxsackievirus A9, was determined (using the method described above) for Example 1 e, giving an overall MIC$_{80}$ of 0.05 µM. MIC$_{50}$ for coxsaciviruses A9, A21 and B3 were 0.005 µM, 0.04 µM and 0.002 µM respectively.

In Vivo Studies

Efficacy data was generated in mouse models of enterovirus infections. Results in a severe disseminated enterovirus infection model in mice (coxsackievirus B3 infection) indicate that Example 1e has shown efficacy in this stringent model.

In a three-part study, Example 1e was administered orally to mice to study its ability to prevent death or paralysis caused by various non-polio enteroviruses. In each part of this study, the mice were infected with an amount of virus shown to result in 80% paralysis and/or death in untreated animals. The animals were then administered Example 1e at various doses prepared in 0.5% xanthan gum with 1% Tween 80. The results of this study are summarized in Tables 3–5.

One part of this study determined the compound's efficacy against coxsackievirus A9 in 150 suckling ICR pups infected subcutaneously within 24 hours of birth. The drug was administered daily for five days beginning 2.5 days postinfection. The results of this part of the study are presented in Table 3. Based on the analysis of the results summarized in Table 3, the 50% protective dose (PD$_{50}$) was determined to be 88 mg/kg per day against coxsackievirus A9.

In another study of the oral efficacy of Example 1e against a coxsackievirus A9 infection in suckling mice, in which the compound was administered once 2.5 days postinfection, the 50% protective dose was determined to be 93 mg/kg per day.

TABLE III

Summary of Antienterovirus Activity of Example 1e
Administered Orally to Mice:
Coxsackievirus A9 [2]

| Dose (mg/kg per day) | % Nonparalyzed at Day 13 |
|---|---|
| 0 | 17 |
| 0.2 | 7 |
| 2.0 | 10 |
| 20 | 10 |
| 200 | 87 |

Another part of the study determined the efficacy of Example 1e against coxsackievirus A21 in 200 weanling ICR mice. The drug was administered on Day 1 two hours prior to infection and two hours after infection. On Day 2 through Day 5, the drug was administered twice a day. The results of this part of the study are presented in Table IV. Based on the analysis of the results summarized in Table IV, the PD$_{50}$ was determined to be 26 mg/kg per day against coxsackievirus A21 in weanling mice.

TABLE IV

Summary of Antienterovirus Activity of Example 1e
Administered Orally to Mice:
Coxsackievirus A21 [2]

| Dose (mg/kg per day) | % Alive at Day 17 |
|---|---|
| 0 | 15 |
| 9.4 | 13 |
| 18.8 | 40 |
| 37.5 | 75 |
| 75 | 100 |

The third part of the study determined the efficacy of Example 1e against coxsackievirus B3 in adult male BALB/c mice. The drug was administered on Day 1 two hours prior to infection and two hours after infection. On Day 2 through Day 5, the drug was administered twice a day. The results of this part of the study are presented in Table V. Based on the analysis of the results summarized in Table V, the 50% protective dose ($PD_{50}$) was determined to be 12 mg/kg per day against coxsackievirus B3 in adult male mice.

TABLE V

Summary of Antienterovirus Activity of Example 1e
Administered Orally to Mice:
Coxsackievirus B3 [2]

| Dose (mg/kg per day) | % Alive at Day 17 |
|---|---|
| 0 | 13 |
| 2 | 8 |
| 20 | 67 |
| 200 | 92 |

Example 1e was orally effective in protecting mice infected with coxsackievirus A9, A21 and B3. Results from a study to determine the efficacy of Example 1e against coxsackievirus A9 in suckling mice indicate that the 50% protective dose ($PD_{50}$) was approximately 88 mg/kg per day. The $PD_{50}$ of Example 1e against coxsackievirus A21 in weanling mice was determined to be approximately 26 mg/kg per day, and the $PD_{50}$ of Example 1e against coxsackievirus B3 in adult male mice was determined to be approximately 12 mg/kg per day.

The compounds of formula I can be formulated into compositions, including sustained release compositions together with one or more non-toxic physiologically acceptable carriers, adjuvants or vehicles which are collectively referred to herein as carriers, in any conventional form, using conventional formulation techniques for preparing compositions for treatment of infection or for propylactic use, using formulations well known to the skilled pharmaceutical chemist, for parenteral injection or oral or nasal administration, in solid or liquid form, for rectal or topical administration, or the like.

The compositions can be administered to humans and animals either orally, rectally, parenterally (intravenous, intramuscularly or subcutaneously), intracisternally, intravaginally, intraperitoneally, locally (powders, ointments or drops), or as an aerosal, for example as a nasal or a buccal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, polyalkylene glycols and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents that delay absorption, for example, aluminum monostearate and gelatin.

Solid dosage forms for oral administration include capsules, tablets, pills, powders, lozenges and granules which may be dissolved slowly in the mouth, in order to bathe the mouth and associated passages with a solution of the active ingredient. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glylcerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as, for example, quaternary ammonium compounds, (g) wetting agents, as for example, cetyl alcohol and glycerol monostearate, (h) adsorbents, as, for example, kaolin and bentonite, and (i) lubricants, as, for example, talc, calcium stearate, magnesium stearate, solid polyethylene glycols, sodium lauryl sulfate or mixtures thereof. In the case of capsules, tablets and pills, the dosage forms may also comprise buffering agents.

Certain solid dosage forms may be delivered through the inhaling of a powder manually or through a device such as a SPIN-HALER used to deliver disodium cromoglycate, INTAL. When using the latter device, the powder can be encapsulated. When employing a liquid composition, the drug can be delivered through a nebulizer, an aerosol vehicle, or through any device which can divide the composition into discrete portions, for example, a medicine dropper or an atomizer.

Solid compositions of a similar type may also formulated for use in soft and hard gelatin capsules, using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. Also solid formulations may be prepared as a base for liquid formulations. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, particularly cottonseed oil, ground-nut oil, corn germ oil, olive oil, castor oil and sesame oil, glycerol, tetrahydrofurfuryl alcohol, polyethyleneglycols and fatty acid esters of sorbitan or mixtures of these substances, and the like. Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administration are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and, therefore, melt in the rectum or vaginal cavity and release the active component.

Compositions for administration as aerosols are prepared by dissolving a compound of Formula I in water or a suitable solvent, for example an alcohol ether, or other inert solvent, and mixing with a volatile propellant and placing in a pressurized container having a metering valve to release the material in usefule droplet size.

The liquefied propellant employed typically one which has a boiling point below ambient temperature at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl chlorides. Further suitable liquefied propellants are the fluorinated and fluorochlorinated lower alkanes such as are sold under the trademarks "Freon" and "Genetron". Mixtures of the abovementioned propellants may suitably be employed.

The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are capsules adapted for insufflation, dropperfuls, aerosols with metered discharges, segregated multiples of any of the foregoing, and other forms as herein described.

Compounds of the invention are useful for the prophylaxis and treatment of infections of suspected picornaviral etiologies such as aseptic meningitis, upper respiratory tract infection, enterovirus infections, coxsackievirus, enteroviruses and the like. An effective but non-toxic quantity of the compound is employed in treatment. The dosage of the compound used in treatment depends on the route of administration, e.g., intra nasal, intra bronchial, and the potency of the particular compound.

Dosage forms for topical administration include ointments, powders, sprays and inhalants. The active component is admixed under sterile conditions with a physiologically acceptable carrier and any preservatives, buffers or propellants as may be required. Opthalmic formulations, eye ointments, powders and solutions are also contemplated.

Actual dosage levels of the active ingredient in the compositions may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors and is readily determined by those skilled in the art.

It will be understood that the specific dose level for any particular patient will depend upon a variety of factors including the body weight, general health, sex, diet, time and route of administration, rates of absorption and excretion, combination with other drugs and the severity of the disease being treated and is readily determined by the skilled clinician.

Because compounds within the scope of the above invention are able to suppress the growth of viruses when added to a medium in which the virus is growing, it is specifically contemplated that compounds of the invention can therefore be used in aqueous solution, for example with a surfactant, to decontaminate surfaces on which polio, Coxsackie, rhinovirus and other viruses are present, such surfaces including, but not limited to, hospital glassware, hospital working surfaces and similar areas in the preparation of food.

Hand contact of nasal mucus may be the most important mode of rhinovirus transmission. Sterilization of the hands of people coming into contact with persons infected with rhinovirus would be a method for preventing further spread of the disease. If a compound of the invention were incorporated into a hand washing or hand care procedure they would inhibit production of rhinovirus and decrease the likelihood of the transmission of the disease.

When administered prior to injection, that is, prophylactically, it is preferred that the administration be within about 0 to 48 hours prior to infection of the host animal with the pathogenic virus. When administered therapeutically to inhibit an infection it is preferred that the administration be within about a day or two after infection with the pathogenic virus.

The dosage unit administered will be dependent upon the virus for which treatment or prophylaxis is desired, the type of animal involved, its age, health, weight, extent of infection, kind of concurrent treatment, if any, frequency of treatment and the nature of the effect desired.

What is claimed is:
1. A compound of the formula

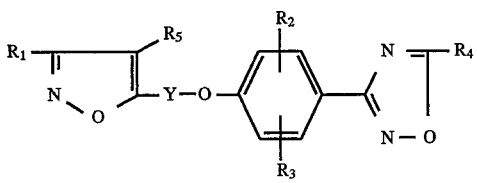

wherein:

$R_1$ is alkyl, alkoxy, hydroxy, cycloalkyl, hydroxyalkyl, alkoxyalkyl, hydroxyalkoxy, alkylthioalkyl, alkylsulfinylalkyl, alkylsulfonylalkyl, aminoalkyl, alkylaminoalkyl, dialkylaminoalkyl, alkoxycarbonyl, carboxy or cyanomethyl;

Y is alkylene of 3 to 9 carbon atoms, $R_2$ and $R_3$ independently are hydrogen, alkyl, alkoxy, halo, cyano, trifluoromethyl or nitro;

$R_4$ is alkoxy, hydroxy, halomethyl, dihalomethyl, trihalomethyl, dihaloethyl, cycloalkyl, heterocyclyl, alkoxycarbonyl, hydroxyalkyl, alkoxyalkyl, alkanecarbonyloxyalkyl, cyano, halo, thioalkyl, alkylthioalkyl, alkylthio, thio, 2,2,2-trifluoroethyl, (4-methylphenyl)sulfonyloxymethyl, N=Q or CON=Q, where N=Q is amino, alkylamino or dialkylamino;

$R_5$ is halo or hydrogen, or alkyl.

2. A compound according to claim 1 of the formula

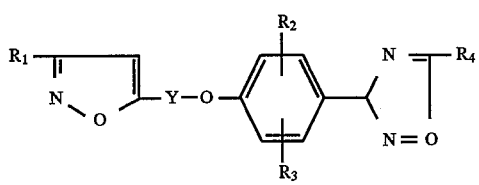

wherein:

$R_1$ is alkyl, alkoxy, hydroxy, cycloalkyl, hydroxyalkyl, alkoxyalkyl, hydroxyalkoxy;

Y is alkylene of 3 to 9 carbon atoms;

$R_2$ and $R_3$ are independently hydrogen, alkyl, alkoxy, halo, trifluoromethyl or nitro;

$R_4$ is alkoxy, hydroxy, halomethyl, dihalomethyl, trihalomethyl, cycloalkyl, alkoxycarbonyl, hydroxyalkyl, alkoxyalkyl, alkanecarbonyloxyalkyl, cyano, (4-methylphenyl)sulfonyloxymethyl, N=Q or CON=Q, wherein N=Q is amino, alkylamino or dialkylamino.

3. A compound according to claim 2 wherein:

$R_1$ is $C_{1-5}$-alkyl, $C_{1-5}$-alkoxy, hydroxy, cyclopropyl, hydroxy-$C_{1-5}$-alkyl, $C_{1-5}$-alkoxy-$C_{1-5}$-alkyl or hydroxy-$C_{1-5}$-alkoxy, methylthiomethyl, methylsulfonylmethyl, methylsulfinylmethyl;

$R_2$ and $R_3$ independently are hydrogen, $C_{1-3}$-alkyl or halo; and $R_4$ is $C_{1-3}$-alkoxy, hydroxy, halomethyl, dihalomethyl, trihalomethyl, cyclopropyl, $C_{1-3}$-alkoxycarbonyl, hydroxy-$C_{1-3}$-alkyl, $C_{1-3}$-alkoxy-$C_{1-3}$-alkyl, ($C_{1-3}$-alkyl, ($C_{1-3}$-alkane)carboxyloxy-$C_{1-3}$-alkyl, 1,1-difluoroethyl, cyano, 2,2,2-trifluoroethyl, 4-(methylphenyl)sulfonyl-oxymethyl, N=Q or CON=Q, where N=Q is amino, $C_{1-3}$-alkylamino or di-($C_{1-3}$-alkyl)amino.

4. A compound according to claim 3 wherein Y is alkylene of 3 to 5 carbon atoms.

5. A compound according to claim 2 of the formula

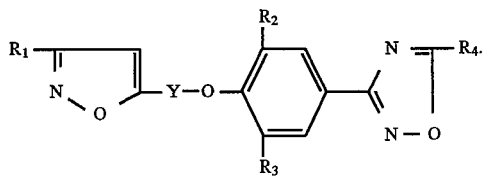

6. A compound according to claim 5 wherein:

$R_1$ is $C_{1-5}$-alkyl, $C_{1-5}$-alkoxy, hydroxy, cyclopropyl, hydroxy-$C_{1-5}$-alkyl, $C_{1-5}$-alkoxy-$C_{1-5}$-alkyl or hydroxy-$C_{1-5}$-alkoxy, methylthiomethyl, methylsulfinylmethyl, methylsulfonylmethyl;

$R_2$ and $R_3$ independently are hydrogen, $C_{1-5}$-alkyl or halo; and $R_4$ is $C_{1-3}$-alkoxy, hydroxy, halomethyl, dihalomethyl, trihalomethyl, cyclopropyl, $C_{1-3}$-alkoxycarbonyl, hydroxy-$C_{1-3}$-alkyl, $C_{1-3}$-alkoxy-$C_{1-3}$-alkyl, ($C_{1-3}$-alkane)carbonyloxy-$C_{1-3}$-alkyl, cyano, 1,1-difluoroethyl, 2,2,2-trifluoroethyl, 4-(methylphenyl)sulfonyl-oxymethyl, N=Q or CON=Q, where N=Q is amino, $C_{1-3}$-alkylamino or di-($C_{1-3}$-alkyl)amino.

7. A compound according to claim 6 wherein Y is alkylene of 3 to 5 carbon atoms.

8. A compound according to claim 7 wherein $R_4$ is $C_{1-3}$-alkoxy, fluoromethyl, dihalomethyl, trihalomethyl, cyclopropyl or $C_{1-3}$-alkoxy-$C_{1-3}$-alkyl.

9. A compound according to claim 8 wherein Y is alkylene of 3 to 5 carbon atoms.

10. A compound according to claim 9 selected from the group consisting of:

5-{3-[4-(5-cyclopropyl-1,2,4-oxadiazol-3-yl)-2,6-dimethylphenoxy]propyl}-3-methylisoxazole;

5-{3-[2,6-dimethyl-4-(5-methoxymethyl-1,2,4-oxadiazol-3-yl)phenoxy]propyl}-3-methylisoxazole;

5-{3-[2,6-dimethyl-4-(5-fluoromethyl-1,2,4-oxadiazol-3-yl)phenoxy]propyl}-3-methylisoxazole;

5-{3-[2,6-dimethyl-4-(5-trichloromethyl-1,2,4-oxadiazol-3-yl)phenoxy]propyl}-3-methylisoxazole;

5-{3-[4-(5-dichloromethyl-1,2,4-oxadiazol-3-yl)-2,6-dimethylphenoxy]propyl}-3-methylisoxazole;

5-{3-[4-(5-difluoromethyl-1,2,4-oxadiazol-3-yl)-2,6-dimethylphenoxy]propyl}-3-methylisoxazole;

5-{3-[2,6-dimethyl-4-(5-methoxy-1,2,4-oxadiazol-3-yl)phenoxy]propyl}-3-methylisoxazole;

5-{3-[2,6-dimethyl-4-(5-ethoxy-1,2,4-oxadiazol-3-yl)phenoxy]propyl}-3-methylisoxazole;

5-{3-[4-(5-cyclopropyl-1,2,4-oxadiazol-3-yl)-2,6-dimethylphenoxy]propyl}-3-ethylisoxazole;

5-{3-[5-(cyclopropyl-1,2,4-oxadiazol-3-yl)-2,6-dimethylphenoxy]propyl}-3-(methoxymethyl)isoxazole;

5-{3-[5-(cyclopropyl-1,2,4-oxadiazol-3-yl)-2,6-dimethylphenoxy]propyl}-3-cyclopropyl-isoxazole;

5-(3-[4-(5-cyclopropyl-1,2,4-oxadiazol-3-yl)-2,6-dimethylphenoxy]propyl}-3-(hydroxymethyl)isoxazole;

5-{3-[4-(5-cyclopropyl-1,2,4-oxadiazol-3-yl)-2,6-dimethylphenoxy]propyl}-3-hydroxyisoxazole;

5-{3-[4-(5-cyclopropyl-1,2,4-oxadiazol-3-yl)-2,6-dimethylphenoxy]propyl}-3-ethoxyisoxazole; and 5-{3-[4-(5-cyclopropyl-1,2,4-oxadiazol-3-yl)-2,6-dimethylphenoxy]propyl}-3-(2-hydroxyethoxy)isoxazole.

11. A composition for combatting picornaviruses which comprises an antivirally effective amount of a compound according to claim 2 in admixture with a suitable pharmaceutical carrier or diluent.

12. A composition according to claim 11 for combatting rhinoviruses.

13. A composition for combatting picornaviruses which comprises an antivirally effective amount of a compound according to claim 5 in admixture with a suitable pharmaceutical carrier or diluent.

14. A composition according to claim 13 for combatting rhinoviruses.

15. A method for combatting picornaviruses which comprises contacting the locus of said viruses with a compound according to claim 1.

16. A method for combatting picornaviruses which comprises contacting the locus of said viruses with a compound according to claim 2.

17. A method for combatting picornaviruses which comprises contacting the locus of said viruses with a compound according to claim 5.

18. A method for combatting a picornaviral infection in a mammalian host which comprises administering to said host an antivirally effective amount of a composition according to claim 13.

19. A method for combatting a rhinovirus infection in a mammalian host which comprises administering to said host an antivirally effective amount of a composition according to claim 12.

20. A method for combatting a rhinovirus infection in a mammalian host which comprises administering to said host an antivirally effective amount of a composition according to claim 14.

21. A compound of the formula

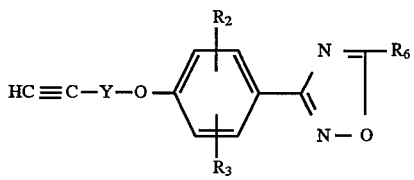

wherein:

Y is alkylene of 3 to 9 carbon atoms;

$R_2$ and $R_3$ independently are hydrogen, alkyl, alkoxy, halo, trifluoromethyl or nitro; and $R_6$ is alkoxy, fluoromethyl, difluoromethyl, trihalomethyl, cycloalkyl or alkoxyalkyl.

22. A compound according to claim 21 selected from 3-[3,5-dimethyl-4-(3-ethinylpropoxy)phenyl]-5-trifluoromethyl-1,2,4-oxadiazole and 5-cyclopropyl-3-[3,5-dimethyl-4-(3-ethinylpropoxy)phenyl]-1,2,4-oxadiazole.

23. A compound of the formula

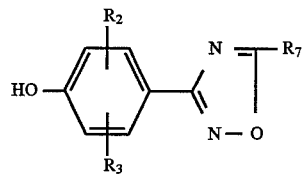

wherein:

$R_2$ and $R_3$ independently are hydrogen, alkyl, alkoxy, halo, trifluoromethyl or nitro; and $R_7$ is alkoxy, fluoromethyl, difluoromethyl, trifluoromethyl, cycloalkyl, alkoxyalkyl or cyano.

24. A compound according to claim 23 selected from 3-(3,5-dimethyl-4-hydroxyphenyl)-5-trifluoromethyl-1,2,4-oxadiazole, 3-(3,5-dichloro-4-hydroxyphenyl)-5-trifluoromethyl-1,2,4-oxadiazole and 3-(4-hydroxyphenyl)-5-tri-fluoromethyl-1,2,4-oxadiazole.

25. A compound of the formula

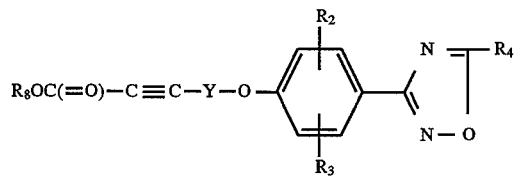

wherein:

Y is alkylene of 3 to 9 carbon atoms;

$R_2$ and $R_3$ independently are hydrogen, alkyl, alkoxy, halo, trifluoromethyl or nitro;

$R_4$ is cycloalkyl or alkoxyalkyl; and $R_8$ is alkyl.

26. 5-Cyclopropyl-3-[4-(5-ethoxycarbonyl-4-pentynyloxy)-3,5-dimethylphenyl]-1,2,4-oxadiazole according to claim 25.

27. A compound according to claim 1 wherein $R_5$ is hydrogen and $R_2$ and $R_3$ are in 2,6 positions and Y is propylene.

28. A compound according to claim 27 wherein $R_1$ is alkylthioalkyl, alkylsulfinylalkyl, alkylsulfonylalkyl, dialkylaminoalkyl, alkylaminoalkyl, aminoalkyl, carboxy, or cyanomethyl.

29. A compound according to claim 28 wherein $R_1$ is chosen from the group consisting of; methyl, ethylthiomethyl, ethylsulfinylmethyl, ethylsulfonylmethyl, methylthiomethyl, methylsulfinylmethyl, methylsulfonylmethyl, dimethylaminomethyl, cyanomethyl and carboxy.

30. A composition for combatting picornaviruses which comprises an antivirally effective amount of a compound according to claim 27 in admixture with a suitable pharmaceutical carrier or diluent.

31. A composition for combatting picornaviruses which comprises an antivirally effective amount of a compound according to claim 28 in admixture with a suitable pharmaceutical carrier or diluent.

32. A composition for combatting picornaviruses which comprises an antivirally effective amount of a compound according to claim 29 in admixture with a suitable pharmaceutical carrier or diluent.

33. A method for combatting a picornaviral infection in a mammalian host which comprises administering to said host an antivirally effective amount of a composition according to claim 30.

34. A method for combatting a picornaviral infection in a mammalian host which comprises administering to said host an antivirally effective amount of a composition according to claim 31.

35. A method for combatting a picornaviral infection in a mammalian host which comprises administering to said host an antivirally effective amount of a composition according to claim 32.

* * * * *